United States Patent
Jiang et al.

(10) Patent No.: US 9,598,544 B2
(45) Date of Patent: Mar. 21, 2017

(54) PARTICLES COATED WITH ZWITTERIONIC POLYMERS COMPRISING SULFOBETAINE OR CARBOXYBETAINE

(71) Applicant: University of Washington, Seattle, WA (US)

(72) Inventors: Shaoyi Jiang, Redmond, WA (US); Shengfu Chen, Hangzhou (CN); Yung Chang, Luzhu Township (TW); Zheng Zhang, Cambridge, MA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 24 days.

(21) Appl. No.: 14/184,540

(22) Filed: Feb. 19, 2014

(65) Prior Publication Data

US 2014/0235803 A1    Aug. 21, 2014

Related U.S. Application Data

(63) Continuation of application No. 12/941,938, filed on Nov. 8, 2010, now abandoned, which is a
(Continued)

(51) Int. Cl.
*C07C 317/08* (2006.01)
*C07C 317/28* (2006.01)
(Continued)

(52) U.S. Cl.
CPC ........... *C08J 3/075* (2013.01); *A61K 49/18* (2013.01); *C07C 317/08* (2013.01);
(Continued)

(58) Field of Classification Search
CPC ... C07C 317/08; C07C 317/28; C07C 317/44; C07C 317/50; A61K 47/20; A61K 49/18
(Continued)

(56) References Cited

U.S. PATENT DOCUMENTS 3,671,305 A    6/1972   Brown et al.
3,671,502 A    6/1972   Samour
(Continued)

FOREIGN PATENT DOCUMENTS

CN    1369313 A    9/2002
DE    152867 Z    12/1981
(Continued)

OTHER PUBLICATIONS

West et al., The biocompatibility of crosslinkable copolymer coatings containing sulfobetains and phosphobetaines, Biomaterials, 2004, 25(7-8):1195-1204).*
(Continued)

*Primary Examiner* — Holly Le
(74) *Attorney, Agent, or Firm* — Christensen O'Connor Johnson Kindness PLLC

(57) ABSTRACT

Nanoparticles zwitterionic polymers grafted thereto or grafted therefrom, and methods for making and using the nanoparticles. Zwitterionic nanogels, and methods for making and using the nanogels.

19 Claims, 37 Drawing Sheets
(25 of 37 Drawing Sheet(s) Filed in Color)

Related U.S. Application Data continuation-in-part of application No. 12/020,998, filed on Jan. 28, 2008, now Pat. No. 7,879,444, which is a continuation of application No. PCT/US2006/028988, filed on Jul. 25, 2006.

(60) Provisional application No. 61/259,081, filed on Nov. 6, 2009, provisional application No. 60/711,613, filed on Aug. 25, 2005.

(51) Int. Cl.

| | | |
|---|---|---|
| C07C 317/44 | (2006.01) | |
| C07C 317/50 | (2006.01) | |
| A61K 49/18 | (2006.01) | |
| C08J 3/075 | (2006.01) | |
| C09D 5/16 | (2006.01) | |
| C09D 7/12 | (2006.01) | |
| C08F 120/36 | (2006.01) | |
| C08F 292/00 | (2006.01) | |
| B82Y 30/00 | (2011.01) | |
| C08K 3/16 | (2006.01) | |
| C08K 3/34 | (2006.01) | |
| C08K 9/08 | (2006.01) | |
| C08F 220/36 | (2006.01) | |

(52) U.S. Cl.
CPC .......... *C07C 317/28* (2013.01); *C07C 317/44* (2013.01); *C07C 317/50* (2013.01); *C08F 120/36* (2013.01); *C08F 292/00* (2013.01); *C09D 5/1637* (2013.01); *C09D 7/1225* (2013.01); *C09D 7/1266* (2013.01); *C09D 7/1275* (2013.01); *B82Y 30/00* (2013.01); *C08F 2220/365* (2013.01); *C08F 2438/01* (2013.01); *C08K 3/16* (2013.01); *C08K 3/34* (2013.01); *C08K 9/08* (2013.01)

(58) Field of Classification Search
USPC ......... 428/407; 424/497, 501; 514/709, 727, 514/740
See application file for complete search history.

(56) References Cited

U.S. PATENT DOCUMENTS

| | | | |
|---|---|---|---|
| 4,138,446 A | 2/1979 | Kawakami | |
| 4,205,152 A | 5/1980 | Mizuguchi et al. | |
| 5,026,490 A | 6/1991 | Peiffer et al. | |
| 5,204,060 A | 4/1993 | Allenmark | |
| 5,256,751 A | 10/1993 | Vanderlaan | |
| 5,311,223 A | 5/1994 | Vanderlaan | |
| 5,356,459 A | 10/1994 | Bikson et al. | |
| 5,391,669 A | 2/1995 | Sulc et al. | |
| 5,686,066 A | 11/1997 | Harada et al. | |
| 5,919,523 A | 7/1999 | Sundberg | |
| 6,225,431 B1 | 5/2001 | Bowers et al. | |
| 6,284,854 B1 | 9/2001 | Bowers et al. | |
| 6,361,768 B1 | 3/2002 | Galleguillos | |
| 6,486,333 B1 | 11/2002 | Murayama | |
| 6,897,263 B2 | 5/2005 | Hell | |
| 7,291,427 B2 | 11/2007 | Kawamura | |
| 7,306,625 B1 | 12/2007 | Stratford | |
| 7,335,248 B2 | 2/2008 | Abou-Nemeh | |
| 7,507,530 B2 | 3/2009 | Huang et al. | |
| 7,632,389 B2 | 12/2009 | Wen et al. | |
| 7,737,224 B2 | 6/2010 | Willis | |
| 7,879,444 B2* | 2/2011 | Jiang .................... | B82Y 30/00 428/403 |
| 2003/0124368 A1 | 7/2003 | Lynn et al. | |
| 2003/0199653 A1 | 10/2003 | McCormick et al. | |
| 2004/0067503 A1 | 4/2004 | Tan et al. | |
| 2004/0256232 A1 | 12/2004 | Jiang et al. | |
| 2005/0008497 A1 | 1/2005 | Ishihara | |
| 2005/0058689 A1 | 3/2005 | McDaniel | |
| 2008/0181861 A1* | 7/2008 | Jiang et al. ................. | 424/78.09 |
| 2010/0152708 A1* | 6/2010 | Li et al. ........................ | 604/523 |
| 2011/0105712 A1* | 5/2011 | Jiang et al. ..................... | 528/26 |
| 2011/0305909 A1* | 12/2011 | Weaver et al. ............ | 428/423.1 |

FOREIGN PATENT DOCUMENTS

| | | |
|---|---|---|
| DE | 10 2006 004 111 A1 | 8/2007 |
| EP | 0 354 984 A2 | 2/1990 |
| EP | 0 419 654 A1 | 4/1991 |
| EP | 0 479 245 A2 | 4/1992 |
| GB | 1419097 | 12/1975 |
| JP | 63-234007 A | 9/1988 |
| JP | 02-170898 A2 | 7/1990 |
| JP | 07-300513 A | 11/1995 |
| JP | 2000-026249 A2 | 1/2000 |
| JP | 2000-086536 A2 | 3/2000 |
| JP | 2000-098310 A2 | 4/2000 |
| JP | 2000-111847 A2 | 4/2000 |
| JP | 2000-119130 A2 | 4/2000 |
| JP | 2000-169526 A2 | 6/2000 |
| JP | 2000-178123 A2 | 6/2000 |
| JP | 2000-212376 A2 | 8/2000 |
| JP | 2000-279512 A2 | 10/2000 |
| JP | 2000-290155 A2 | 10/2000 |
| JP | 2000-327570 A2 | 11/2000 |
| JP | 2000-344645 A2 | 12/2000 |
| JP | 2000-344658 A2 | 12/2000 |
| JP | 2001-106749 A2 | 4/2001 |
| JP | 2001-261740 A2 | 9/2001 |
| JP | 2001-525464 A | 12/2001 |
| JP | 2002-098676 A2 | 4/2002 |
| JP | 2002-322320 A2 | 11/2002 |
| JP | 2002-360690 A2 | 12/2002 |
| JP | 2004-331637 A2 | 11/2004 |
| JP | 2005-006704 A2 | 1/2005 |
| JP | 2007-130194 A | 5/2007 |
| PL | 156073 B1 | 2/1992 |
| RU | 1780673 A1 | 12/1992 |
| SU | 859371 A1 | 8/1981 |
| WO | 99/29818 A1 | 6/1999 |
| WO | 00/01424 A1 | 1/2000 |
| WO | 00/32184 A1 | 6/2000 |
| WO | 00/39176 A1 | 7/2000 |
| WO | 01/07097 A2 | 2/2001 |
| WO | 01/97776 A1 | 12/2001 |
| WO | 03/070289 A1 | 8/2003 |
| WO | 2004/058837 A2 | 7/2004 |
| WO | 2004/074298 A1 | 9/2004 |
| WO | 2004/088319 A1 | 10/2004 |
| WO | 2004/100666 A1 | 11/2004 |
| WO | 2005/029095 A1 | 3/2005 |
| WO | 2007/024393 A2 | 3/2007 |
| WO | 2008/019381 A1 | 2/2008 |
| WO | 2008/083390 A2 | 7/2008 |
| WO | 2009/067562 A1 | 5/2009 |

OTHER PUBLICATIONS

Chang et al, Highly protein-resistant coatings from well-defined diblock copolymers containing sulfobetaines, Langmuir 2006, 22, 2222-2226.*

Canadian Office Action mailed Jul. 19, 2013, issued in corresponding Canadian Application No. 2,619,361, filed Jul. 25, 2006, 3 pages.

Chang, Y., et al., "Highly Protein-Resistant Coatings From Well-Defined Diblock Copolymers Containing Sulfobetaines," Langmuir 22(5):2222-2226, Feb. 2006.

Chen, S., et al., "Controlling Antibody Orientation on Charged Self-Assembled Monolayers," Langmuir 19(7):2859-2864, Apr. 2003.

Chen, S., et al., "Strong Resistance of Oligo(phosphorylcholine) Self-Assembled Monolayers to Protein Adsorption," Langmuir 22(6):2418-2421, Mar. 2006.

Chen, S., et al., "Strong Resistance of Phosphorylcholine Self-Assembled Monolayers to Protein Adsorption: Insights Into

(56) References Cited

OTHER PUBLICATIONS

Nonfouling Properties of Zwitterionic Materials," Journal of the American Chemical Society 127(41):14473-14478, Oct. 2005.

Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.

Feng., W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.

Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.

Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.

Li, L., et al., "Protein Adsorption on Alkanethiolate Self-Assembled Monolayers: Nanoscale Surface Structural and Chemical Effects," Langmuir 19(7):2974-2982, Apr. 2003.

Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.

Lowe, A.B., et al., "Well-Defined Sulfobetaine-Based Statistical Copolymers as Potential Antibioadherent Coatings," Journal of Biomedical Materials Research 52(1):88-94, Oct. 2000.

West, S.L., et al., "The Biocompatibility of Crosslinkable Copolymer Coatings Containing Sulfobetaines and Phosphobetaines," Biomaterials 25(7-8):1195-1204, Mar.-Apr. 2004.

Wu, R.-L., et al., "Swelling Behaviors of a New Zwitterionic N-carboxymethyl-N,N-dimethyl-N-allylammonium/acrylic Acid Hydrogel," Journal of Polymer Research 13(1):33-37, Feb. 2006.

Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

Yuan, J., et al., "Improvement of Blood Compatibility on Cellulose Membrane Surface by Grafting Betaines," Colloids and Surfaces B: Biointerfaces 30(1-2):147-155, Jul. 2003.

Yuan, J., et al., "Platelet Adhesion Onto Segmented Polyurethane Surfaces Modified by Carboxybetaine," Journal of Biomaterial Science, Polymer Edition 14(12):1339-1349, Dec. 2003.

Yuan, Y., et al., "Grafting Sulfobetaine Monomer Onto Silicone Surface to Improve Haemocompatability," Polymer International 53(1):121-126, Jan. 2004.

Yuan, Y., et al., "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.

Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.

Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.

Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.

Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.

Zhang, Z., et al., "Superlow Fouling Sulfobetaine and Carboxybetaine Polymers on Glass Slides," Langmuir 22(24):10072-10077, Nov. 2006.

Zhang, Z., "Surface Grafted Sulfobetaine Polymers Via Atom Transfer Radical Polymerization as Superlow Fouling Coatings," Journal of Physical Chemistry B 110(22)10799-10804, Jun. 2006.

Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.

Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.

Zhou, J., et al., "Platelet Adhesion and Protein Adsorption on Silicone Rubber Surface by Ozone-Induced Grafted Polymerization with Carboxybetaine Monomer," Colloids and Surfaces B: Biointerfaces 41(1):55-62, Mar. 2005.

Feldman, K., et al., "Probing Resistance to Protein Adsorption of Oligo(ethylene glycol)-Terminated Self-Assembled Monolayers by Scanning Force Microscopy," Journal of the American Chemical Society 121(43):10134-10141, Oct. 1999.

Ferretti, S., et al., "Self-Assembled Monolayers: A Versatile Tool for the Formulation of Bio-Surfaces," Trends in Analytical Chemistry 19(9):530-540, Sep. 2000.

Fu, Q., et al., "Force Titration of ω-Mercapto-n-undecylamine Self-Assembled Monolayers by Chemical Force Microscopy," Chemical Journal of Chinese Universities 21(11):1738-1741, Nov. 2000 (English abstract).

Gombotz, W.R., et al., "Immobilization of Poly(ethylene oxide) on Poly(ethylene terephthalate) Using a Plasma Polymerization Process," Journal of Applied Polymer Science 37(1):91-107, Jan. 1989.

Gopireddy, D., and S.M. Husson, "Room Temperature Growth of Surface-Confined Poly(acrylamide) From Self-Assembled Monolayers Using Atom Transfer Radical Polymerization," Macromolecules 35(10):4218-4221, Apr. 2002.

Grasel, T.G., et al., "Effects of Alkyl Grafting on Surface Properties and Blood Compatibility of Polyurethane Block Copolymers," Journal of Biomedical Materials Research 21(7):815-842, Jul. 1987.

Green, R.J., et al., "Investigation of the Hydration Kinetics of Novel Poly(ethylene oxide) Containing Polyurethanes," Langmuir 16(6):2744-2750, Feb. 2000.

Green, R.J., et al., "Surface Plasmon Resonance Analysis of Dynamic Biological Interactions With Biomaterials," Biomaterials 21(18):1823-1835, Sep. 2000.

Green, R.J., et al., "Surface Plasmon Resonance for Real Time in Situ Analysis of Protein Adsorption to Polymer Surfaces," Biomaterials 18(5):405-413, Mar. 1997.

Harder, P., et al., "Molecular Conformation in Oligo(ethylene glycol)-Terminated Self-Assembled Mono Layers on Gold and Silver Surfaces Determines Their Ability to Resist Protein Adsorption," Journal of Physical Chemistry B 102(2):426-436, Jan. 1998.

Harris, D.J., et al., "Conformation of Poly(ethylene oxide)-Hydroxybenzene Molecular Complexes Studied by Solid-State NMR," Macromolecules 33(9):3375-3381, Mar. 2000.

Harris, J.M., "Introduction to Biotechnical and Biomedical Applications of Poly(ethylene Glycol)," in "Poly(ethylene Glycol) Chemistry: Biotechnical and Biomedical Applications," Plenum Press: New York and London, 1992, Chap. 1, pp. 1-14.

Harris, L.J., et al., "Crystallographic Structure of an Intact IgG1 Monoclonal Antibody," Journal of Molecular Biology 275(5):861-872, Feb. 1998.

Harris, L.J., et al., "Refined Structure of an Intact IgG2a Monoclonal Antibody," Biochemistry 36(7):1581-1597, Feb. 1997.

Hauser, H., et al., "Preferred Conformation and Molecular Packing of Phosphatidylethanolamine and Phosphatidylcholine," Biochimica et Biophysica Acta 650(1):21-51, Jun. 1981.

Haynes, C.A., and W. Norde, "Structures and Stabilities of Adsorbed Proteins," Journal of Colloid and Interface Science 169(2):313-328, Feb. 1995.

Hayward, J.A., and D. Chapman, "Biomembrane Surfaces as Models for Polymer Design: The Potential for Haemocompatibility," Biomaterials 5(3):135-142, May 1984.

Herron, J.N., et al., "Orientation and Activity of Immobilized Antibodies," in M. Malmsten (ed.), "Biopolymers at Interfaces," Marcel Dekker, New York, 1998, Chap. 8, pp. 221-280.

Herrwerth, S., et al., "Factors That Determine the Protein Resistance of Oligoether Self-Assembled Monolayers—Internal Hydrophilicity, Terminal Hydrophilicity, and Lateral Packing Density," Journal of the American Chemical Society 125(31):9359-9366, Aug. 2003.

(56) References Cited

OTHER PUBLICATIONS

Hinterdorfer, P., et al., "Detection and Localization of Individual Antibody Antigen Recognition Events by Atomic Force Microscopy," Proceedings of the National Academy of Sciences USA (PNAS) 93(8):3477-3481, Apr. 1996.
Hoffman, A.S., and B.D. Ratner, "Nonfouling Surfaces," in B.D. Ratner et al. (eds.), "Biomaterials Science: An Introduction to Materials in Medicine," 2nd ed., Elsevier Academic Press, San Diego, 2004, Chap. 2.13, pp. 197-201.
Holmlin, R.E., et al., "Zwitterionic SAMs That Resist Nonspecific Adsorption of Protein From Aqueous Buffer," Langmuir 17(9):2841-2850, Apr. 2001.
Homola, J., "On the Sensitivity of Surface Plasmon Resonance Sensors With Spectral Interrogation," Sensors and Actuators B: Chemical 41(1-3):207-211, Jun. 1997.
Homola, J., et al., "Spectral Surface Plasmon Resonance Biosensor for Detection of Staphylococcal Enterotoxin B in Milk," International Journal of Food Microbiology 75(1-2):61-69, May 2002.
Homola, J., et al., "Surface Plasmon Resonance Sensors: Review," Sensors and Actuators B: Chemical 54(1-2):3-15, Jan. 1999.
Horbett, T.A., "The Role of Adsorbed Proteins in Animal Cell Adhesion," Colloids and Surfaces B: Biointerfaces 2(1-3):225-240, Mar. 1994.
Horsley, D., et al., "Human and Hen Lysozyme Adsorption: A Comparative Study Using Total Internal Reflection Fluorescence Spectroscopy and Molecular Graphics," in J.L. Brash and T.A. Horbett (eds.), "Proteins at Interfaces: Physicochemical and Biochemical Studies," American Chemical Society, Washington, DC, 1987, vol. 343, Chap. 19, pp. 290-305.
Huang, N.-P., et al., "Biotin-Derivatized Poly(L-lysine)-g-poly(ethylene glycol): A Novel Polymeric Interface for Bioaffinity Sensing," Langmuir 18(1):220-230, Dec. 2001.
Huang, W., et al., "Functionalization of Surfaces by Water-Accelerated Atom-Transfer Radical Polymerization of Hydroxyethyl Methacrylate and Subsequent Derivatization," Macromolecules 35(4):1175-1179, Jan. 2002.
Imoto, T., et al., "Vertebrate Lysozymes," in P.D. Boyer (ed.), "The Enzymes," 3rd ed., Academic Press, New York, 1972, vol. 7, pp. 665-868.
International Search Report and Written Opinion mailed Jun. 1, 2007, issued in International Application No. PCT/US2006/028988, filed Jul. 25, 2006, 9 pages.
Ishihara, K., et al., "Modification of Polysulfone With Phospholipid Polymer for Improvement of the Blood Compatibility. Part 1. Surface Characterization," Biomaterials 20(17):1545-1551, Sep. 1999.
Ishihara, K., et al., "Protein Adsorption From Human Plasma Is Reduced on Phospholipid Polymer," Journal of Biomedical Materials Research 25(11):1397-1407, Nov. 1991.
Ishihara, K., et al., "Why Do Phospholipid Polymers Reduce Protein Adsorption?" Journal of Biomedical Material Research 39(2):323-330, Feb. 1998.
Iyer, A.K., et al., "Exploiting the Enhanced Permeability and Retention Effect for Tumor Targeting," Drug Discovery Today 11(17-18):812-818, Sep. 2006.
Jal, P.K., "Chemical Modification of Silica Surface by Immobilization of Functional Groups for Extractive Concentration of Metal Ions," Talanta 62(5):1005-1028, Apr. 2004.
Japanese Office Action dated Jun. 6, 2012, for Application No. JP 2008-527925, filed Jul. 24, 2006, 5 pages.
Japanese Office Action dated Mar. 5, 2013, for Application No. JP 2008-527925, filed Jul. 24, 2006, 7 pages.
Jeon, S.I., and J.D. Andrade, "Protein-Surface Interactions in the Presence of Polyethylene Oxide: II. Effect of Protein Size," Journal of Colloid and Interface Science 142(1):159-166, Mar. 1991.
Jeon, S.I., et al., "Protein-Surface Interactions in the Presence of Polyethylene Oxide: I. Simplified Theory," Journal of Colloid and Interface Science 142(1):149-158, Mar. 1991.
Jia, G., et al., "Novel Zwitterionic-Polymer-Coated Silica Nanoparticles," Langmuir 25(5):3196-3199, Feb. 2009.

Jiang, X., et al., "Palladium as a Substrate for Self-Assembled Monolayers Used in Biotechnology," Analytical Chemistry 76(20):6116-6121, Oct. 2004.
Jones, D.M., and W.T.S. Huck, "Controlled Surface-Initiated Polymerizations in Aqueous Media," Advanced Materials 13(16):1256-1259, Aug. 2001.
Jones, D.M., et al., "Surface-Initiated Polymerizations in Aqueous Media: Effect of Initiator Density," Langmuir 18(4):1265-1269, Jan. 2002.
Kane, R.S., et al., "Kosmotropes Form the Basis of Protein-Resistant Surfaces," Langmuir 19(6):2388-2391, Jan. 2003.
Kidoaki, S., and T. Matsuda, "Adhesion Forces of the Blood Plasma Proteins on Self-Assembled Monolayer Surfaces of Alkanethiolates With Different Functional Groups Measured by an Atomic Force Microscope," Langmuir 15(22):7639-7646, Sep. 1999.
Kim, D., et al., "Antibiofouling Polymer-Coated Gold Nanoparticles as a Contrast Agent for In Vivo X-Ray Computed Tomography Imaging," Journal of the American Chemical Society 129(24):7661-7665, Jun. 2007.
Kim, D.J., et al., "Formation of Thermoresponsive Gold Nanoparticle/PNIPAAm Hybrids by Surface-Initiated, Atom Transfer Radical Polymerization in Aqueous Media," Macromolecular Chemistry and Physics 206(19):1941-1946, Oct. 2005.
Kim, D.K., et al., "Protective Coating of Superparamagnetic Iron Oxide Nanoparticles," Chemistry of Materials 15(8):1617-1627, Mar. 2003.
Kim, H.I., et al., "Viscous 'Interphase' Water Adjacent to Oligo(ethylene glycol)-Terminated Monolayers," Langmuir 19(22):9271-9275, Oct. 2003.
Norde, W., "Adsorption of Proteins From Solution at the Solid-Liquid Interface," Advances in Colloid and Interface Science 25(4):267-340, Sep. 1986.
Norde, W., and A.C.I. Anusiem, "Adsorption, Desorption and Re-Adsorption of Proteins on Solid Surfaces," Colloids and Surfaces 66(1):73-80, Sep. 1992.
Nordgren, C.E., et al., "Molecular Dynamics Simulations of a Hydrated Protein Vectorially Oriented on Polar and Nonpolar Soft Surfaces," Biophysical Journal 83(6):2906-2917, Dec. 2002.
Nuss, S., et al., "Gold Nanoparticles With Covalently Attached Polymer Chains," Angewandte Chemie International Edition 40(21):4016-4018, Nov. 2001.
Ohno, K., et al., "Synthesis of Monodisperse Silica Particles Coated With Well-Defined, High-Density Polymer Brushes by Surface-Initiated Atom Transfer Radical Polymerization," Macromolecules 38(6):2137-2142, Feb. 2005.
Oi, V.T., et al., "Correlation Between Segmental Flexibility and Effector Function of Antibodies," Nature 307(5947):136-140, Jan. 1984.
Ostuni, E., et al., "The Interaction of Proteins and Cells With Self-Assembled Monolayers of Alkanethiolates on Gold and Silver," Colloids and Surfaces B: Biointerfaces 15(1):3-30, Aug. 1999.
Ostuni, E., et al., "Self-Assembled Monolayers That Resist the Adsorption of Proteins and the Adhesion of Bacterial and Mammalian Cells," Langmuir 17(20):6336-6343, Aug. 2001.
Ostuni, E., et al., "A Survey of Structure—Property Relationships of Surfaces That Resist the Adsorption of Protein," Langmuir 17(18):5605-5620, Jul. 2001.
Pale-Grosdemange, C., et al., "Formation of Self-Assembled Monolayers by Chemisorption of Derivatives of Oligo(ethylene glycol) of Structure $HS(CH_2)_{11}(OCH_2CH_2)$ mOH on Gold," Journal of the American Chemical Society 113(1):12-20, Jan. 1991.
Perstin, A.J., and M. Grunze, "Computer Simulation of Water Near the Surface of Oligo(ethylene glycol)-Terminated Alkanethiol Self-Assembled Monolayers," Langmuir 16(23):8829-8841, Aug. 2000.
Pertsin, A.J., et al., "Grand Canonical Monte Carlo Simulations of the Hydration Interaction Between Oligo(ethylene glycol)-Terminated Alkanethiol Self-Assembled Monolayers," Journal of Physical Chemistry B 106(47):12274-12281, Oct. 2002.
Pertsin, A.J., et al., "Low-Energy Configurations of Methoxy Triethylene Glycol Terminated Alkanethiol Self-Assembled Monolayers and Their Relevance to Protein Adsorption," Journal of Physical Chemistry B 102(25):4918-4926, May 1998.

(56) References Cited

OTHER PUBLICATIONS

Philipse, A.P., and A. Vrij, "Preparation and Properties of Nonaqueous Model Dispersions of Chemically Modified, Charged Silica Spheres," Journal of Colloid and Interface Science 128(1):121-136, Mar. 1989.
Poirier, G.E., "Coverage-Dependent Phases and Phase Stability of Decanethiol on Au(111)," Langmuir 15(4):1167-1175, Jan. 1999.
Poirier, G.E., "Mechanism of Formation of Au Vacancy Islands in Alkanethiol Monolayers on Au(111)," Langmuir 13(7):2019-2026, Apr. 1997.
Polyak, B., et al., "High Field Gradient Targeting of Magnetic Nanoparticle-Loaded Endothelial Cells to the Surfaces of Steed Stents," Proceedings of the National Academy of Sciences USA (PNAS) 105(2):698-703, Jan. 2008.
Prime, K.L., and G.M. Whitesides, "Adsorption of Proteins Onto Surfaces Containing End-Attached Oligo(ethylene oxide): A Model System Using Self-Assembled Monolayers," Journal of the American Chemical Society 115(23):10714-10721, Nov. 1993.
Prime, K.L., and G.M. Whitesides, "Self-Assembled Organic Monolayers-Model Systems for Study Adsorption of Proteins at Surfaces," Science 252(5009):1164-1167, May 1991.
Rabinow, B.E., et al., "Biomaterials With Permanent Hydrophilic Surfaces and Low Protein Adsorption Properties," Journal of Biomaterials Science, Polymer Edition 6(1):91-109, 1995.
Radmacher, M., "Imaging Adhesion Forces and Elasticity of Lysozyme Adsorbed on Mica With the Atomic Force Microscope," Langmuir 10(10):3809-3814, Oct. 1994.
Rao, S.V., "Oriented Immobilization of Proteins," Microchimica Acta 128(3):127-143, Sep. 1998.
Rich, R.L., and D.G. Myszka, "Survey of the 1999 Surface Plasmon Resonance Biosensor Literature," Journal of Molecular Recognition 13(6):388-407, Nov.-Dec. 2000.
Rixman, M.A., et al., "Nanoscale Intermolecular Interactions Between Human Serum Albumin and Alkanethiol Self-Assembled Monolayers," Langmuir 19(15):6202-6218, Jun. 2003.
Roberts, G.G., "An Applied Science Perspective of Langmuir-Blodgett Films," Advances in Physics 34(4):475-512, 1985.
Ross, E.E., et al., "Planar Supported Lipid Bilayer Polymers Formed by Vesicle Fusion. 2. Adsorption of Bovine Serum Albumin," Langmuir 19(5):1766-1774, Jan. 2003.
Salmeron, M., et al., "Nanometer Scale Mechanical Properties of Au(111) Thin Films," Langmuir 8(11):2832-2842, Nov. 1992.
Sato, T., et al., "Magnetic Properties of Ultrafine Ferrite Particles," Journal of Magnetism and Magnetic Materials 65(2-3):252-256, Mar. 1987.
Sawaguchi, T., et al., "Ordered Structures of Self-Assembled Monolayers of 3-Mercaptopropionic Acid on Au(111): In Situ Scanning Tunneling Microscopy Study," Physical Chemistry Chemical Physics 3(16):3399-3404, Jul. 2001.
Schreiber, F., "Structure and Growth of Self-Assembling Monolayers," Progress in Surface Science 65(5-8):151-256, Nov.-Dec. 2000.
Scouten, W.H., et al., "Enzyme or Protein Immobilization Techniques for Applications in Biosensor Design," Trends in Biotechnology (TIBTECH) 13(5):178-185, May 1995.
Seo, S.-B., et al., "Novel Multifunctional PHDCA/PEI Nano-Drug Carriers for Simultaneous Magnetically Targeted Cancer Therapy and Diagnosis via Magnetic Resonance Imaging," Nanotechnology 18(47):475105, 8 pages, Oct. 2007.
Sethuraman, A., et al., "Effect of Surface Wettability on the Adhesion of Proteins," Langmuir 20(18):7779-7788, Aug. 2004.
Sever, M.J., and J.J. Wilker, "Synthesis of Peptides Containing DOPA (3,4-Dihydroxyphenylalanine)," Tetrahedron 57(29):6139-6146, Jul. 2001.
Shen, M., et al., "Inhibition of Monocyte Adhesion and Fibrinogen Adsorption on Glow Discharge Plasma Deposited Tetraethylene Glycol Dimethyl Ether," Journal of Biomaterials Science, Polymer Edition 12(9):961-978, 2001.
Shen, M., et al., "PEO-Like Plasma Polymerized Tetraglyme Surface Interactions With Leukocytes and Proteins: In Vitro and In Vivo Studies," Journal of Biomaterials Science, Polymer Edition 13(4):367-390, 2002.
Sheng, Q., et al., "Molecular Dynamic Simulation of Immobilized Artificial Membranes," Journal of Physical Chemistry 99(27):11018-11027, Jul. 1995.
Sheth, S.R., and D.E. Leckband, "Measurements of Attractive Forces Between Proteins and End-Grafted Poly(ethylene glycol) Chains," Proceedings of the National Academy of Sciences USA (PNAS) 94(16):8399-8404, Aug. 1997.
Shevade, A.V., et al., "Adsorption of Water—Methanol Mixtures in Carbon and Aluminosilicate Pores: A Molecular Simulation Study," Molecular Physics 97(10):1139-1148, 1999.
Silin, V.V., et al., "SPR Studies of the Nonspecific Adsorption Kinetics of Human IgG and BSA on Gold Surfaces Modified by Self-Assembled Monolayers (SAMs)," Journal of Colloid and Interface Science 185(1):94-103, Jan. 1997.
Smith, G.D., et al., "A Force Field for Simulations of 1,2-Dimethoxyethane and Poly(oxyethylene) Based Upon Ab Initio Electronic Structure Calculations on Model Molecules," Journal of Physical Chemistry 97(49):12752-12759, Dec. 1993.
Smith, G.D., et al., "A Revised Quantum Chemistry-Based Potential for Poly(ethylene oxide) and Its Oligomers in Aqueous Solution," Journal of Computational Chemistry 23(15):1480-1488, Nov. 2002.
Smith, L.J., et al., "Comparison of MD Simulations and NMR Experiments for Hen Lysozyme. Analysis of Local Fluctuations, Cooperative Motions, and Global Changes," Biochemistry 34(34):10918-10931, Aug. 1995.
Sondag-Huethorst, J.A.M., et al., "Formation of Holes in Alkanethiol Monolayers on Gold," Journal of Physical Chemistry 98(27):6826-6834, Jul. 1994.
Sorensen, R.A., et al., "Prediction of Polymer Crystal Structures and Properties: Polyethylene and Poly(oxymethylene)," Macromolecules 21(1):200-208, Jan. 1988.
Steinbach, P.J., and B.R. Brooks, "New Spherical-Cutoff Methods for Long-Range Forces in Macromolecular Simulation," Journal of Computational Chemistry 15(7):667-683, Jul. 1994.
Stöber, W., et al., "Controlled Growth of Monodisperse Silica Spheres in the Micron Size Range," Journal of Colloid and Interface Science 26(1):62-69, Jan. 1968.
Storhoff, J.J., et al., "One-Pot Colorimetric Differentiation of Polynucleotides With Single Base Imperfections Using Gold Nanoparticle Probes," Journal of the American Chemical Society 120(9):1959-1964, Feb. 1998.
Storri, S., et al., "Surface Modifications for the Development of Piezoimmunosensors," Biosensors and Bioelectronics 13(3-4):347-357, Mar. 1998.
Su, T.J., et al., "Adsorption of Lysozyme Onto the Silicon Oxide Surface Chemically Grafted With a Monolayer of Pentadecyl-1-ol," Langmuir 16(11):4999-5007, Apr. 2000.
Ahluwalia, A., et al., "A Comparative Study of Protein Immobilization Techniques for Optical Immunosensors," Biosensors and Bioelectronics 7(3):207-214, 1992.
Archambault, J.G., and J.L. Brash, "Protein Repellent Polyurethane-Urea Surfaces by Chemical Grafting of Hydroxyl-Terminated Poly(ethylene oxide): Effects of Protein Size and Charge," Colloids and Surfaces B: Biointerfaces 33(2):111-120, Jan. 2004.
Bain, C.D., and G.M. Whitesides, "Attenuation Lengths of Photoelectrons in Hydrocarbon Films," Journal of Physical Chemistry 93(4):1670-1673, Feb. 1989.
Bain, C.D., and G.M. Whitesides, "Formation of Monolayers by the Coadsorption of Thiols on Gold: Variation in the Length of the Alkyl Chain," Journal of the American Chemical Society 111(18):7164-7175, Aug. 1989.
Bain, C.D., et al., "Formation of Monolayers by the Coadsorption of Thiols on Gold: Variation in the Head Group, Tail Group, and Solvent," Journal of the American Chemical Society 111(18):7155-7164, Aug. 1989.
Bandyopadhyay, S., et al., "Molecular Dynamics Study of the Poly(oxyethylene) Surfactant $C_{12}E_2$ and Water," Langmuir 16(3):942-946, Nov. 1999.

(56) References Cited

OTHER PUBLICATIONS

Barbé, C., et al., "Silica Particles: A Novel Drug-Delivery System," Advanced Materials 16(21):1959-1966, Nov. 2004.

Beck, D.A.C., et al., "Cutoff Size Need Not Strongly Influence Molecular Dynamics Results for Solvated Polypeptides," Biochemistry 44(2):609-616, Jan. 2005.

Benninghoven, A., et al., "Surface Analysis by Secondary Ion Mass Spectrometry (SIMS)," Surface Science 299/300:246-260, Jan. 1994.

Bergen, J.M., et al., "Gold Nanoparticles as a Versatile Platform for Optimizing Physicochemical Parameters for Targeted Drug Delivery," Macromolecular Bioscience 6(7):506-516, Jul. 2006.

Bergkvist, M., et al., "A Method for Studying Protein Orientation With Atomic Force Microscopy Using Relative Protein Volumes," Journal of Physical Chemistry B 105(10):2062-2069, Feb. 2001.

Bergkvist, M., et al., "TM-AFM Threshold Analysis of Macromolecular Orientation: A Study of the Orientation of IgG and IgE on Mica Surfaces," Journal of Colloid and Interface Science 206(2):475-481, Oct. 1998.

Bourgeat-Lami, E., "Organic-Inorganic Nanostructured Colloids," Journal of Nanoscience and Nanotechnology 2(1):1-24, Feb. 2002.

Brash, J.L., and T.A. Horbett, "Proteins at Interfaces: An Overview," in T.A. Horbett and J.L. Brash (eds.), "Proteins at Interfaces II, Fundamentals and Applications," ACS Symposium Series, American Chemical Society: Washington, DC, May 1995, vol. 602, pp. 1-23.

Brooks, B.R., et al., "CHARMM: A Program for Macromolecular Energy, Minimization, and Dynamics Calculations," Journal of Computational Chemistry 4(2)187-217, Summer 1983.

Buckle, P.E., et al., "The Resonant Mirror: A Novel Optical Sensor for Direct Sensing of Biomolecular Interactions Part II: Applications," Biosensors and Bioelectronics 8(7-8):355-363, 1993.

Buijs, J., et al., "Adsorption of Monoclonal IgGs and Their F(ab')$_2$ Fragments Onto Polymeric Surfaces," Colloids and Surfaces B: Biointerfaces 5(1-2):11-23, Sep. 1995.

Buijs, J., et al., "The Effect of Adsorption on the Antigen Binding by IgG and its F(ab')$_2$ Fragments," Colloids and Surfaces B: Biointerfaces 8(4-5):239-249, Apr. 1997.

Bumm, L.A., et al., "Directed Self-Assembly to Create Molecular Terraces With Molecularly Sharp Boundaries in Organic Monolayers," Journal of the American Chemical Society 121(35):8017-8021, Aug. 1999.

Burkhardt, M., et al., "Cytoplasmic Overexpression of ALCAM Is Prognostic of Disease Progression in Breast Cancer," Journal of Clinical Pathology 59(4):403-409, Apr. 2006.

Cacace, M.G., et al., "The Hofmeister Series: Salt and Solvent Effects on Interfacial Phenomena," Quarterly Reviews of Biophysics 30(3):241-277, Aug. 1997.

Castner, D.G., et al., "X-Ray Photoelectron Spectroscopy Sulfur 2p Study of Organic Thiol and Disulfide Binding Interactions With Gold Surfaces," Langmuir 12(21):5083-5086, Oct. 1996.

Chaki, N.K., and K. Vijayamohanan, "Self-Assembled Monolayers as a Tunable Platform for Biosensor Applications," Biosensors and Bioelectronics 17(1-2):1-12, Jan. 2002.

Chapman, R.G., et al., "Polymeric Thin Films That Resist the Adsorption of Proteins and the Adhesion of Bacteria," Langmuir 17(4):1225-1233, Feb. 2001.

Chen, S., and S.Y. Jiang, "A New Avenue to Nonfouling Materials," Advanced Materials 20(2):335-338, Jan. 2008.

Chen, S., et al., "Controlled Chemical and Structural Properties of Mixed Self-Assembled Monolayers by Coadsorption of Symmetric and Asymmetric Disulfides on Au(111)," Journal of Physical Chemistry B 105(15):2975-2980, Mar. 2001.

Chen, S., et al., "Controlled Chemical and Structural Properties of Mixed Self-Assembled Monolayers of Alkanethiols on Au(111)," Langmuir 16(24):9287-9293, Nov. 2000.

Cheng, G., et al., "A Switchable Biocompatible Polymer Surface With Self-Sterilizing and Nonfouling Capabilities," Angewandte Chemie International Edition 47(46):8831-8834, Nov. 2008.

Cheng, G., et al., "Zwitterionic Carboxybetaine Polymer Surfaces and Their Resistance to Long-Term Biofilm Formation," Biomaterials 30(28):5234-5240, Oct. 2009.

Chi, Q., et al., "Ordered Assembly and Controlled Electron Transfer of the Blue Copper Protein Azurin at Gold (111) Single-Crystal Substrates," Journal of Physical Chemistry B 105(20):4669-4679, May 2001.

Chittur, K.K., "FTIR/ATR for Protein Adsorption to Biomaterial Surfaces," Biomaterials 19(4-5):357-369, Mar. 1998.

Chung, Y.C., et al., "Self-Assembled Biomimetic Monolayers Using Phospholipid-Containing Disulfides," Biomaterials 26(15):2313-2324, May 2005.

Corot, C., et al., "Recent Advances in Iron Oxide Nanocrystal Technology for Medical Imaging," Advanced Drug Delivery Reviews 58(14):1471-1504, Dec. 2006.

Dadarlat, V.M., and C.B. Post, "Insights Into Protein Compressibility From Molecular Dynamics Simulations," Journal of Physical Chemistry B 105(3):715-724, Dec. 2000.

Dalsin, J.L., et al., "Protein Resistance of Titanium Oxide Surfaces Modified by Biologically Inspired mPEG Dopa," Langmuir 21(2):640-646, Jan. 2005.

Dávalos-Pantoja, L., et al., "Colloidal Stability of IgG- and IgY-Coated Latex Microspheres," Colloids and Surfaces B: Biointerfaces 20(2):165-175, Feb. 2001.

Dobson, J., "Magnetic Nanoparticles for Drug Delivery," Drug Development Research 67(1):55-60, Jan. 2006.

Dubois, L.H., and R.G. Nuzzo, "Synthesis, Structure, and Properties of Model Organic Surfaces," Annual Review of Physical Chemistry 43:437-463, Oct. 1992.

Duguet, E., et al., "Magnetic Nanoparticles and Their Applications in Medicine," Nanomedicine 1(2):157-168, Aug. 2006.

Dupont-Gillain, Ch. C., et al., "Use of AFM to Probe the Adsorption Strength and Time-Dependent Changes of Albumin on Self-Assembled Monolayers," Journal of Biomedical Materials Research Part A 67A(2):548-558, Nov. 2003.

Durrani, A.A., et al., "Biomembranes as Models for Polymer Surfaces: II. The Syntheses of Reactive Species for Covalent Coupling of Phosphorylcholine to Polymer Surfaces," Biomaterials 7(2):121-125, Mar. 1986.

Edinger, K., et al., "Formation of Self-Assembled Monolayers of n-Alkanethiols on Gold: A Scanning Tunneling Microscopy Study on the Modification of Substrate Morphology," Langmuir 9(1):4-8, Jan. 1993.

Edmiston, P.L., and S.S. Saavedra, "Molecular Orientation Distributions in Protein Films. 4. A Multilayer Composed of Yeast Cytochrome c Bound Through an Intermediate Streptavidin Layer to a Planar Supported Phospholipid Bilayer," Journal of the American Chemical Society 120(8):1665-1671, Mar. 1998.

Edmiston, P.L., et al., "Molecular Orientation Distributions in Protein Films. 1. Cytochrome c Adsorbed to Substrates of Variable Surface Chemistry," Journal of the American Chemical Society 119(3):560-570, Jan. 1997.

Efremova, N.V., et al., "Protein-Induced Changes in Poly(ethylene glycol) Brushes: Molecular Weight and Temperature Dependence," Langmuir 17(24):7628-7636, Nov. 2001.

Fabianowski, W., et al., "Spontaneous Assembly of Phosphatidylcholine Monolayers via Chemisorption Onto Gold," Langmuir 5(1):35-41, Jan. 1989.

Faca, V.M., et al., "A Mouse to Human Search for Plasma Proteome Changes Associated With Pancreatic Tumor Development," PLoS Medicine 5(6):e123, pp. 953-967, Jun. 2008.

Fan, X., et al., "Isolation of Carbon Nanohorn Assemblies and Their Potential for Intracellular Delivery," Nanotechnology 18(19):195103, 6 pages, May 2007.

Fang, C., and M. Zhang, "Multifunctional Magnetic Nanoparticles for Medical Imaging Applications," Journal of Materials Chemistry 19(35):6258-6266, Jan. 2009.

Fang, C., et al., "Functionalized Nanoparticles With Long-Term Stability in Biological Media," Small 5(14):1637-1641, Jul. 2009.

Sun, C., et al., "Magnetic Nanoparticles in MR Imaging and Drug Delivery," Advanced Drug Delivery Reviews 60(11):1252-1265, Aug. 2008.

(56) References Cited

OTHER PUBLICATIONS

Sun, F., et al., "Adsorption of Ultrathin Films of Sulfur-Containing Siloxane Oligomers on Gold Surfaces and Their In Situ Modification," Macromolecules 27(11):3053-3062, May 1994.

Szleifer, I., "Protein Adsorption on Surfaces With Grafted Polymers: A Theoretical Approach," Biophysical Journal 72(2 Pt. 1):595-612, Feb. 1997.

Takami, T., et al., "Recognition of Individual Tail Groups in Self-Assembled Monolayers," Langmuir 11(10):3876-3881, Oct. 1995.

Takano, H., et al., "Chemical and Biochemical Analysis Using Scanning Force Microscopy," Chemical Reviews 99(10):2845-2890, Oct. 1999.

Tasaki, K., "Conformation and Dynamics of Poly(oxyethylene) in Benzene Solution: Solvent Effect From Molecular Dynamics Simulation," Macromolecules 29(27):8922-8933, Dec. 1996.

Tasaki, K., "Poly(oxyethylene)-Water Interactions: A Molecular Dynamics Study," Journal of the American Chemical Society 118(35):8459-8469, Sep. 1996.

Tegoulia, V.A., et al., "Surface Properties, Fibrinogen Adsorption, and Cellular Interactions of a Novel Phosphorylcholine-Containing Self-Assembled Monolayer on Gold," Langmuir 17(14):4396-4404, Jun. 2001.

Terán Arce, F., et al., "Complex Structural Dynamics at Adsorbed Alkanethiol Layers at Au(111) Single-Crystal Domains," Langmuir 14(25):7203-7212, Nov. 1998.

Thierry, B., et al., "Electrostatic Self-Assembly of PEG Copolymers Onto Porous Silica Nanoparticles," Langmuir 24(15):8143-8150, Aug. 2008.

Tidwell, C.D., et al., "Endothelial Cell Growth and Protein Adsorption on Terminally Functionalized, Self-Assembled Monolayers of Alkanethiolates on Gold," Langmuir 13(13):3404-3413, Jun. 1997.

Tobias, D.J., et al., "Molecular Dynamics Simulations of a Protein on Hydrophobic and Hydrophilic Surfaces," Biophysical Journal 71(6):2933-2941, Dec. 1996.

Tsai, W.-B., et al., "Platelet Adhesion to Polystyrene-Based Surfaces Preadsorbed With Plasmas Selectively Depleted in Fibrinogen, Fibronectin, Vitronectin, or von Willebrand's Factor," Journal of Biomedical Materials Research 60(3):348-359, Jun. 2002.

Tsonchev, S., et al., "All-Atom Numerical Studies of Zwitterionic Peptide Amphiphiles," Journal of Physical Chemistry B 108(39)15278-15284, Sep. 2004.

Tsukagoshi, T., et al., "Protein Adsorption on Polymer-Modified Silica Particle Surface," Colloid and Surfaces B: Biointerfaces 54(1):101-107, Jan. 2007.

Ueda, T., et al., "Preparation of 2-Methacryloyloxyethyl Phosphorylcholine Copolymers With Alkyl Methacrylates and Their Blood Compatibility," Polymer Journal 24(11):1259-1269, Nov. 1992.

Umeda, T., et al., "Polymeric Phospholipid Analogues, 14: The Convenient Preparation of a Vinyl Monomer Containing a Phospholipid Analogue," Die Makromolekulare Chemie, Rapid Communications (Macromolecular Rapid Communications) 3(7):457-459, Jul. 1982.

Vaisocherova, H., et al., "Ultralow Fouling and Functionalizable Surface Chemistry Based on a Zwitterionic Polymer Enabling Sensitive and Specific Protein Detection in Undiluted Blood Plasma," Analytical Chemistry 80(20):7894-7901, Oct. 2008.

Vanderah, D.J., et al., "Control of Protein Adsorption: Molecular Level Structural and Spatial Variables," Journal of the American Chemical Society 126(42):13639-13641, Oct. 2004.

Vanderah, D.J., et al., "Self-Assembled Monolayers of Methyl 1-Thiahexa(ethylene oxide) for the Inhibition of Protein Adsorption," Langmuir 18(12):4674-4680, May 2002.

Vermette, P., and L. Meagher, "Interactions of Phospholipid- and Poly(ethylene glycol)-Modified Surfaces With Biological Systems: Relation to Physico-Chemical Properties and Mechanisms," Colloids and Surfaces B: Biointerfaces 28(2-3):153-198, Apr. 2003.

Vert, M., and D. Domurado, "Poly(ethylene Glycol): Protein-Repulsive or Albumin-Compatible?" Journal of Biomaterials Science, Polymer Edition 11(12):1307-1317, 2000.

Wang, D.-A., et al., "Synthesis and Characterization of a Novel Degradable Phosphate-Containing Hydrogel," Biomaterials 24(22):3969-3980, Oct. 2003.

Wang, H., et al., "Probing the Orientation of Surface-Immobilized Immunoglobulin G by Time-of-Flight Secondary Ion Mass Spectrometry," Langmuir 20(5):1877-1887, Jan. 2004.

Wang, L., et al., "Watching Silica Nanoparticles Glow in the Biological World," Analytical Chemistry 78(3):646-654, Feb. 2006.

Wang, M.S., et al., "Evaluating Protein Attraction and Adhesion to Biomaterials With the Atomic Force Microscope," Langmuir 20(18):7753-7759, Jul. 2004.

Widrig, C.A., et al., "Scanning Tunneling Microscopy of Ethanethiolate and n-Octadecanethiolate Monolayers Spontaneously Adsorbed at Gold Surfaces," Journal of the American Chemical Society 113(8):2805-2810, Apr. 1991.

Xie, J., et al., "Controlled PEGylation of Monodisperse $Fe_3O_4$ Nanoparticles for Reduced Non-Specific Uptake by Macrophage Cells," Advanced Materials 19(20):3163-3166, Oct. 2007.

Xu, H., et al., "Room-Temperature Preparation and Characterization of Poly(ethylene glycol)-Coated Silica Nanoparticles for Biomedical Applications," Journal of Biomedical Materials Research Part A 66(4):870-879, Sep. 2003.

Yamada, R., et al., "Effect of Temperature on Structure of the Self-Assembled Monolayer of Decanethiol on Au(111) Surface," Langmuir 16(13):5523-5525, Jun. 2000.

Yamada, R., et al., "Solvent Effect on the Structure of the Self-Assembled Monolayer of Alkanethiol," Chemistry Letters 28(7):667-668, 1999.

Yang, W., et al., "Film Thickness Dependence of Protein Adsorption From Blood Serum and Plasma Onto Poly(sulfobetaine)-Grafted Surfaces," Langmuir 24(17):9211-9214, Sep. 2008.

Yang, W., et al., "Functionalizable and Ultra Stable Nanoparticles Coated With Zwitterionic Poly(carboxybetaine) in Undiluted Blood Serum," Biomaterials 30(29):5617-5621, Oct. 2009.

Yang, Z., et al., "Long-Circulating Near-Infrared Fluorescence Core-Cross-Linked Polymeric Micelles: Synthesis, Characterization, and Dual Nuclear/Optical Imaging," Biomacromolecules 8(11):3422-3428, Nov. 2007.

Yavuz, C.T., et al., "Low-Field Magnetic Separation of Monodisperse $Fe_3O_4$ Nanocrystals," Science 314(5801):964-967, Nov. 2006.

Yoon, K.R., et al., "Surface Initiated-Atom Transfer Radical Polymerization of a Sugar Methacrylate on Gold Nanoparticles," Surface and Interface Analysis 40(8):1139-1143, Aug. 2008.

Zhang, Q., et al., "Transport Diffusion of Liquid Water and Methanol Through Membranes," Journal of Chemical Physics 117(2):808-818, Jul. 2002.

Zhang, Z., et al., "Dual-Functional Biomimetic Materials: Nonfouling Poly(carboxybetaine) With Active Functional Groups for Protein Immobilization," Biomacromolecules 7(12):3311-3315, Dec. 2006.

Zhou, J., et al., "Monte Carlo Simulations of Antibody Adsorption and Orientation on Charged Surfaces," Journal of Chemical Physics 121(2):1050-1057, Jul. 2004.

Zhou, J., et al., "Orientation of Adsorbed Antibodies on Charged Surfaces by Computer Simulation Based on a United-Residue Model," Langmuir 19(8):3472-3478, Mar. 2003.

Kim, J.-B., et al., "Surface-Initiated Atom Transfer Radical Polymerization on Gold at Ambient Temperature," Journal of the American Chemical Society 122(31):7616-7617, Jul. 2000.

Kim, J.-B., et al., "Synthesis of Triblock Copolymer Brushes by Surface-Initiated Atom Transfer Radical Polymerization," Macromolecules 35(14):5410-5416, Jun. 2002.

Kitano, H., et al., "Structure of Water Incorporated in Sulfobetaine Polymer Films as Studied by ATR-FTIR," Macromolecular BioScience 5(4):314-321, Apr. 2005.

Ladd, J., et al., "Zwitterionic Polymers Exhibiting High Resistance to Nonspecific Protein Adsorption From Human Serum and Plasma," Biomacromolecules 9(5):1357-1361, May 2008.

(56) References Cited

OTHER PUBLICATIONS

Langer, R., "xDrugs on Target," Science 293(5527):58-59, Jul. 2001.

Larsericsdotter, H., et al., "Thermodynamic Analysis of Proteins Adsorbed on Silica Particles: Electrostatic Effects, " Journal of Colloid and Interface Science 237(1):98-103, May 2001.

Leckband, D., et al., "Grafted Poly(ethylene oxide) Brushes as Nonfouling Surface Coatings," Journal of Biomaterials Science, Polymer Edition 10(10):1125-1147, 1999.

Lee, B.S., et al., "Functionalization of Poly(oligo(ethylene glycol)methacrylate) Films on Gold and Si/SiO$_2$ for Immobilization of Proteins and Cells: SPR and QCM Studies," Biomacromolecules 8(12):3922-3929, Dec. 2007.

Lee, H.-Y., et al., "Synthesis and Characterization of PVP-Coated Large Core Iron Oxide Nanoparticles as an MRI Contrast Agent," Nanotechnology 19(16):165101, Apr. 2008, 6 pages.

Lestelius, M., et al., "In Vitro Plasma Protein Adsorption on ω-Functionalized Alkanethiolate Self-Assembled Monolayers," Langmuir 13(22):5900-5908, Oct. 1997.

Lewis, A.L., "Phosphorylcholine-Based Polymers and Their Use in the Prevention of Biofouling," Colloids and Surfaces B: Biointerfaces 18(3-4):261-275, Oct. 2000.

Li, D., et al., "Fabrication of pH-Responsive Nanocomposites of Gold Nanoparticles/Poly(4-vinylpyridine)," Chemistry of Materials 19(3):412-417, Jan. 2007.

Li, G., et al., "Ultra Low Fouling Zwitterionic Polymers With a Biomimetic Adhesive Group," Biomaterials 29(35):4592-4597, Dec. 2008.

Li, L., et al., "In Situ Single-Molecule Detection of Antibody-Antigen Binding by Tapping-Mode Atomic Force Microscopy," Analytical Chemistry 74(23):6017-6022, Dec. 2002.

Li, L., et al., "Protein Interactions With Oligo(ethylene glycol) (OEG) Self-Assembled Monolayers: OEG Stability, Surface Packing Density and Protein Adsorption," Journal of Biomaterials Science, Polymer Edition 18(11):1415-1427, Nov. 2007.

Li, X., et al., "Thermodynamic Studies on the Adsorption of Fibronectin Adhesion-Promoting Peptide on Nanothin Films of Poly(2-vinylpyridine) by SPR," Biomacromolecules 5(3):869-876, Apr. 2004.

Liedberg, B., et al., "Principles of Biosensing With an Extended Coupling Matrix and Surface Plasmon Resonance," Sensors and Actuators B: Chemical 11(1-3):63-72, Mar. 1993.

Lin, J.-C., and W.-H. Chuang, "Synthesis, Surface Characterization, and Platelet Reactivity Evaluation for the Self-Assembled Monolayer of Alkanethiol With Sulfonic Acid Functionality," Journal of Biomedical Materials Research 51(3):413-423, Sep. 2000.

Liu, G.-Y., and M.B. Salmeron, "Reversible Displacement of Chemisorbed n-Alkanethiol Molecules on Au(111) Surface: An Atomic Force Microscopy Study," Langmuir 10(2):367-370, Feb. 1994.

Liu, G.-Y., et al., "Nanofabrication of Self-Assembled Monolayers Using Scanning Probe Lithography," Accounts of Chemical Research 33(7):457-466, Jul. 2000.

Lowe, A.B., and C.L. McCormick, "Synthesis and Solution Properties of Zwitterionic Polymers," Chemical Reviews 102(11):4177-4189, Nov. 2002.

Lu, B. et al., "Tutorial Review. Oriented Immobilization of Antibodies and Its Applications in Immunoassays and Immunosensors," Analyst 121(3):29R-32R, Mar. 1996.

Lu, C.-W., et al., "Bifunctional Magnetic Silica Nanoparticles for Highly Efficient Human Stem Cell Labeling," Nano Letters 7(1):149-154, Jan. 2007.

Lu, D.R., et al., "Calculation of Solvation Interaction Energies for Protein Adsorption on Polymer Surfaces," Journal of Biomaterials Science, Polymer Edition 3(2):127-147, 1992.

Lu, J.R., et al., "The Denaturation of Lysozyme Layers Adsorbed at the Hydrophobic Solid/Liquid Surface Studied by Neutron Reflection," Journal of Colloid and Interface Science 206(1):212-223, Oct. 1998.

Luk, Y.-Y., et al., "Self-Assembled Monolayers of Alkanethiolates Presenting Mannitol Groups Are Inert to Protein Adsorption and Cell Attachment," Langmuir 16(24):9604-9608, Oct. 2000.

Lyman, D.J., et al., "The Effects of Chemical Structure and Surface Properties of Synthetic Polymers on the Coagulation of Blood. IV. The Relation Between Polymer Morphology and Protein Adsorption," Transactions—American Society for Artificial Internal Organs 21(1):49-54, Apr. 1975.

Lynch, I., and K.A. Dawson, "Protein-Nanoparticle Interactions," Nanotoday 3(1-2):40-47, Feb.-Apr. 2008.

Ma, H., et al., "'Non-Fouling' Oligo(ethylene glycol)-Functionalized Polymer Brushes Synthesized by Surface-Initiated Atom Transfer Radical Polymerization," Advanced Materials 16(4):338-341, Feb. 2004.

MacKerell, A.D., et al., "All-Atom Empirical Potential for Molecular Modeling and Dynamics Studies of Proteins," Journal of Physical Chemistry B 102(18):3586-3616, Apr. 1998.

Malmsten, M., "Protein Adsorption at Phospholipid Surfaces," Journal of Colloid and Interface Science 172(1):106-115, Jun. 1995.

Matsuura, K., et al., "Carboxybetaine Polymer-Protected Gold Nanoparticles: High Dispersion Stability and Resistance Against Non-Specific Adsorption of Proteins," Macromolecular Chemistry and Physics 208(8):862-873, Apr. 2007.

Matyjaszewski, K., et al., "Utilizing Halide Exchange to Improve Control of Atom Transfer Radical Polymerization," Macromolecules 31(20):6836-6840, Sep. 1998.

McCarthy, J.R., and R. Weissleder, "Multifunctional Magnetic Nanoparticles for Targeted Imaging and Therapy," Advanced Drug Delivery Reviews 60(11):1241-1251, Aug. 2008.

McCarthy, J.R., et al., "Targeted Delivery of Multifunctional Magnetic Nanoparticles," Nanomedicine 2(2):153-167, Apr. 2007.

McGuire, J., et al., "The Influence of Net Charge and Charge Location on the Adsorption and Dodecyltrimethylammonium Bromide-Mediated Elutability of Bacteriophage T4 Lysozyme at Silica Surfaces," Journal of Colloid and Interface Science 170(1):193-202, Mar. 1995.

McPherson, T., et al., "Prevention of Protein Adsorption by Tethered Poly(ethylene oxide) Layers: Experiments and Single-Chain Mean-Field Analysis," Langmuir 14(1):176-186, Jan. 1998.

Melendez, J., et al., "A Commercial Solution for Surface Plasmon Sensing," Sensors and Actuators B: Chemical 35(1-3):212-216, Sep. 1996.

Mirkin, C.A., et al., "A DNA-Based Method for Rationally Assembling Nanoparticles Into Macroscopic Materials," Nature 382(6592):607-609, Aug. 1996.

Mirsky, V.M., et al., "Capacitive Monitoring of Protein Immobilization and Antigen-Antibody Reactions on Monomolecular Alkylthiol Films on Gold Electrodes," Biosensors and Bioelectronics 12(9-10):977-989, Nov. 1997.

Miyamoto, D., et al., "Completely Dispersible PEGylated Gold Nanoparticles Under Physiological Conditions: Modification of Gold Nanoparticles With Precisely Controlled PEG-b-polyamine," Langmuir 24(9):5010-5017, May 2008.

Morimoto, K., et al., "Nano-Scale Surface Modification of a Segmented Polyurethane With a Phospholipid Polymer," Biomaterials 25(23):5353-5361, Oct. 2004.

Morimoto, K., et al., "Physical Properties and Blood Compatibility of Surface-Modified Segmented Polyurethane by Semi-Interpenetrating Polymer Networks With a Phospholipid Polymer," Biomaterials 23(24):4881-4887, Dec. 2002.

Mrksich, M., and G.M. Whitesides, "Using Self-Assembled Monolayers to Understand the Interactions of Man-Made Surfaces With Proteins and Cells," Annual Review of Biophysics and Biomolecular Structure 25:55-78, Jan. 1996.

Murphy, E.F., et al., "The Reduced Adsorption of Proteins at the Phosphoryl Choline Incorporated Polymer-Water Interface," Langmuir 15(4):1313-1322, Jan. 1999.

Myszka, D.G., "Improving Biosensor Analysis," Journal of Molecular Recognition 12(5):297-284, Sep.-Oct. 1999.

Nakaya, T., and Y.J. Li, "Phospholipid Polymers," Progress in Polymer Science 24(1):143-181, Apr. 1999.

Nakaya, T., et al., "Poly(phosphatidylcholine) Analogs," Macromolecules 22(7):3180-3181, Jul. 1989.

(56) References Cited

OTHER PUBLICATIONS

Neyertz, S., et al., "Molecular Dynamics Simulation of Crystalline Poly(ethylene oxide)," Journal of Chemical Physics 101(11):10064-10073, Dec. 1994.

Norberg, J., and L. Nilsson, "Advances in Biomolecular Simulations: Methodology and Recent Applications," Quarterly Reviews of Biophysics 36(3):257-306, Aug. 2003.

* cited by examiner

PARTICLES COATED WITH ZWITTERIONIC POLYMERS COMPRISING SULFOBETAINE OR CARBOXYBETAINE

CROSS-REFERENCES TO RELATED APPLICATIONS

This application is a continuation of U.S. patent application Ser. No. 12/941,938, filed Nov. 8, 2010, which claims the benefit of U.S. Provisional Application No. 61/259,081, filed Nov. 6, 2009; and U.S. patent application Ser. No. 12/941,938, filed Nov. 8, 2010, is a continuation-in-part of U.S. patent application Ser. No. 12/020,998, filed Jan. 28, 2008, now U.S. Pat. No. 7,879,444, which is a continuation of PCT/US2006/028988, filed Jul. 25, 2006, which claims the benefit of U.S. Provisional Application No. 60/711,613, filed Aug. 25, 2005. Each application is expressly incorporated herein by reference in its entirety.

STATEMENT OF GOVERNMENT LICENSE RIGHTS

This invention was made with Government support under Contract No. N000140910137 awarded by the Office of Naval Research and Contract No. DMR-0705907 awarded by the National Science Foundation. The Government has certain rights in the invention.

BACKGROUND OF THE INVENTION

Nanoparticle-based biotechnology is quickly heading to the forefront of drug delivery, diagnosis and other areas. One of the largest obstacles to these applications is nonspecific protein adsorption, which can result in cellular uptake, nanoparticle aggregation, immune system response and other disastrous problems for in vivo applications. This lack of a versatile effective nonfouling material is thus a crucial issue for many nanoparticle-based biomedical applications. Poly(ethylene glycol) (PEG) and oligo(ethylene glycol) (OEG) are the most commonly studied nonfouling materials. However, PEG or OEG can auto-oxidize rapidly in the presence of oxygen and transition metal ions. Another class of nonfouling materials is based on phosphorylcholine (PC), but these are harder to synthesize. In addition to fouling resistance, many biomedical applications require a functionalizable surface. This is necessary to immobilize a bio-recognition element for targeting specific disease areas or selectively interacting with cells or biomolecules. There are few reports about directly functionalizing PEG surfaces. However, these involve complex reactions.

Although performance of low fouling materials and coatings has been demonstrated for relative expansive macroscopic surfaces, surface chemistries are still challenging for nanoparticles used in diagnostics and therapeutics, particularly in complex media such as blood.

Therefore, a need exists for low fouling materials and coatings for application to nanoparticles, particularly in complex media. The present invention seeks to fulfill this need and provides further related advantages.

SUMMARY OF THE INVENTION

In one aspect, the invention provides zwitterionic particles in which the particle surface has zwitterionic polymers grafted from the surface or zwitterionic polymers grafted to the surface. Methods for making and using the zwitterionic particles are also provided.

In one embodiment, the invention provides a particle comprising a core and a surface having a plurality of zwitterionic polymers grafted thereto or grafted therefrom. In one embodiment, the particle has nanoscale dimensions. In one embodiment, the core comprises a metal, a metal oxide, a ceramic, a synthetic polymer, a natural polymer, silicon dioxide, a crystal, a semiconductor material, a hydrogel, a liposome, a micelle, or a carbon-based material. In one embodiment, the core comprises gold, silver, iron, or platinum, cadmium sulfide, cadmium selenide, or combinations thereof. In one embodiment, the core comprises titanium oxide, iron oxide, zinc oxide, aluminum oxide, copper oxide, or tantalum oxide, or combinations thereof. In one embodiment, the core comprises a carbon fiber, a carbon nanotube, a carbon nanosheet, a carbon nanobelt, a carbon nanorod, a carbon nanowire, and a carbon nanodish. In one embodiment, the core comprises polyurethane, polyethylene, polystyrene, poly(methyl methacrylate), or silicone. In one embodiment, the core comprises calcium fluoride or quartz. In one embodiment, the core is a quantum dot.

In one embodiment, the zwitterionic polymer has the formula:

$$PB\text{-}(L_1\text{-}N^+(R_a)(R_b)\text{-}L_2\text{-}A(\!=\!\!O)OM)_n(X^-)_n$$

wherein PB is a polymer backbone having n pendant groups $L_1\text{-}N^+(R_a)(R_b)\text{-}L_2\text{-}A(\!=\!\!O)OM)$;

$N^+$ is a cationic center;

$R_a$ and $R_b$ are independently optional as necessary to provide a cationic center and independently selected from alkyl and aryl;

$A(\!=\!\!O)OM$ is the anionic center, wherein A is C, S, SO, P, or PO, and wherein M is a counterion;

$L_1$ is a linker that covalently couples the cationic center to the polymer backbone;

$L_2$ is a linker that covalently couples the cationic center to the anionic center;

$X^-$ is the counter ion associated with the cationic center; and n is an integer from 1 to about 10,000.

In one embodiment, the zwitterionic polymer has the formula:

$$PB\text{-}[L_1\text{-}N^+(R_a)(R_b)(R_c)]_n[L_2\text{-}A(\!=\!\!O)OM]_p(X^-)_n$$

wherein PB is a polymer backbone having n pendant groups $L_1\text{-}N^+(R_a)(R_b)(R_c)$ and p pendant groups $L_2\text{-}A(\!=\!\!O)OM$;

$N^+$ is a cationic center;

$R_a$, $R_b$, and $R_c$ are independently optional as necessary to provide a cationic center and independently selected from alkyl and aryl;

$A(\!=\!\!O)\text{—}OM$ is the anionic center, wherein A is C, S, SO, P, or PO, and wherein M is a counterion;

$L_1$ is a linker that covalently couples the cationic center to the polymer backbone;

$L_2$ is a linker that covalently couples the anionic center to the polymer backbone;

$X^-$ is the counter ion associated with the cationic center;

n is an integer from 1 to about 10,000; and p is an integer from 1 to about 10,000.

In certain embodiments, the particle further comprises one or more targeting agents.

In another aspect, the invention provides zwitterionic nanogels. Methods for making and using the zwitterionic nanogels are also provided.

In one embodiment, the invention provides a nanogel, comprising a zwitterionic polymer having the formula:

$$PB\text{-}(L_1\text{-}N^+(R_a)(R_b)\text{-}L_2\text{-}A(\!=\!\!O)OM)_n(X^-)_n$$

wherein PB is a polymer backbone having n pendant groups $L_1-N^+(R_a)(R_b)-L_2-A(=O)OM)$ and comprises crosslinks for those nanogels that are crosslinked;

$N^+$ is a cationic center;

$R_a$ and $R_b$ are independently optional as necessary to provide a cationic center and independently selected from alkyl and aryl;

$A(=O)OM$ is the anionic center, wherein A is C, S, SO, P, or PO, and wherein M is a counterion;

$L_1$ is a linker that covalently couples the cationic center to the polymer backbone;

$L_2$ is a linker that covalently couples the cationic center to the anionic center;

$X^-$ is the counter ion associated with the cationic center; and n is an integer from 1 to about 10,000.

In another embodiment, the invention provides a nanogel, comprising a zwitterionic polymer having the formula:

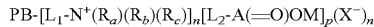

$$PB-[L_1-N^+(R_a)(R_b)(R_c)]_n[L_2-A(=O)OM]_p(X^-)_n$$

wherein PB is a polymer backbone having n pendant groups $L_1-N^+(R_a)(R_b)(R_c)$ and p pendant groups $L_2-A(=O)-OM$ and comprises crosslinks for those nanogels that are crosslinked;

$N^+$ is a cationic center;

$R_a$, $R_b$, and $R_c$, are independently optional as necessary to provide a cationic center and independently selected from alkyl and aryl;

$A(=O)OM$ is the anionic center, wherein A is C, S, SO, P, or PO, and wherein M is a counterion;

$L_1$ is a linker that covalently couples the cationic center to the polymer backbone;

$L_2$ is a linker that covalently couples the anionic center to the polymer backbone;

$X^-$ is the counter ion associated with the cationic center;

n is an integer from 1 to about 10,000; and p is an integer from 1 to about 10,000.

In certain embodiments, the nanogels further comprises one or more therapeutic agents and/or one or more diagnostic agents.

In another aspect, the invention provides methods for delivering a diagnostic agent and/or a therapeutic agent to a subject. In the method, a nanogel of the invention comprising one or more therapeutic agents and/or one or more diagnostic agents is administered to the subject.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1A:
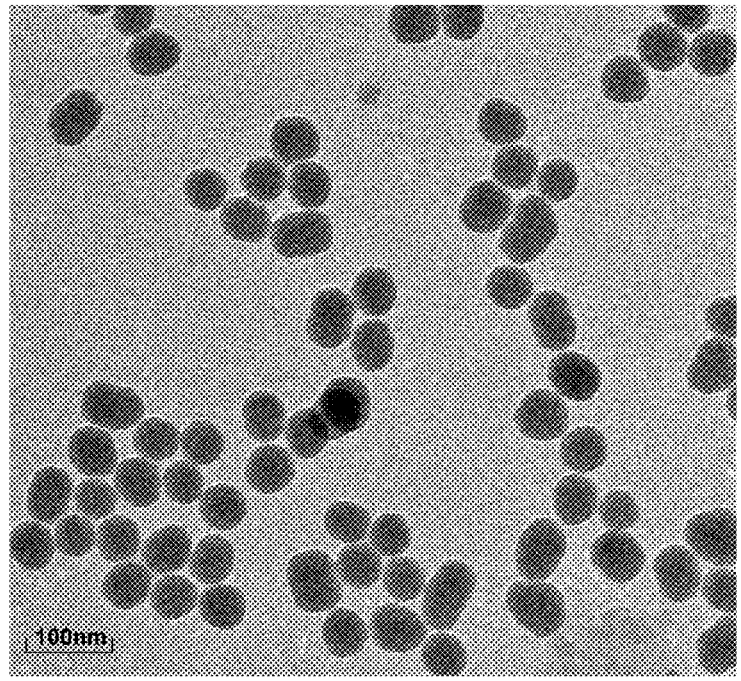
FIGS. 1A and 1B are tunneling electron microscopy (TEM) images of silica nanoparticles before coating (1A) and representative zwitterionic polymer coated silica particles of the invention, polyCBAA-SiP1 (1B).

The invention provides particles having low fouling properties, methods for making the particles, and methods for using the particles.

In one aspect, the invention provides zwitterionic particles in which the particle surface has zwitterionic polymers grafted from the surface or zwitterionic polymers grafted to the surface. Methods for making and using the zwitterionic particles are also provided.

In another aspect, the invention provides zwitterionic nanogels. Methods for making and using the zwitterionic nanogels are also provided.

Zwitterionic Particles

In one aspect, the present invention provides particles having zwitterionic polymers on their surfaces that impart low fouling properties to the particles. In one embodiment, the zwitterionic polymers on the surface of the particles are grafted from the particle surface by polymerization processes. In another embodiment, the zwitterionic polymers on the surface of the particles are grafted to the particle surface by associating a suitably functionalized zwitterionic polymer with the particle surface. In another embodiment, the zwitterionic polymers or hydrogels are coated onto particle surfaces.

Particles

The nature of the particle, which is advantageously treated by the methods of the invention to provide the particle having a surface to which the zwitterionic polymers are associated, can be widely varied in size as well as composition. In one embodiment, the particle is a nanoparticle, which is a particle having nanometer scale dimensions.

Representative particle surfaces that can be advantageously treated with the polymers include metal and metal oxide surfaces, ceramic surfaces, synthetic and natural polymeric surfaces, glass surfaces, fiber glass surface, silicon/silica surfaces, and carbon-based material surfaces. Suitable particle surfaces include semiconductor particle surfaces (e.g., quantum dots, cadmium sulfide and cadmium selenide), hydrogel surfaces, liposome surfaces, and micelle surfaces. Representative natural polymeric surfaces include collagen, fibrins, and other carbohydrate surfaces. Representative particle carbon-based surfaces include carbon fiber surfaces, carbon nanotube surfaces, bulky ball surfaces, carbon nanosheet surfaces, carbon nanotube surfaces, carbon nanowire surfaces, carbon nanorod surfaces, and carbon nanodish surfaces.

Representative metals particle surfaces to which the polymers can be attached include gold, silver, iron, and platinum surfaces. Representative metal oxide particle surfaces to which the polymers can be attached include titanium oxide, iron oxide, zinc oxide, aluminum oxide, copper oxide, and tantalum oxide surfaces. Representative silicon oxide particle surfaces to which the polymers can be attached include glass surfaces, and silica wafers. Representative organic particle surfaces to which the polymers can be attached include organic surfaces such as organic polymer surfaces including polyurethane, polyethylene, polystyrene, poly(methyl methacrylate) and silicone. Particles having surfaces comprising mixtures of the above can also be advantageously treated with the zwitterionic polymers of the invention.

The polymers of the invention can be advantageously adhered to fiber particle surfaces. Representative fibers and fibrous materials to which the polymers can be adhered include nylon, polyvinyl nitrile, and polyester.

The polymers of the invention can also be advantageously adhered to crystalline particle surfaces. Representative crystalline surfaces include calcium fluoride and quartz surfaces.

Particles Having Zwitterionic Polymers Grafted Therefrom

In one aspect, the invention provides particle surfaces having zwitterionic polymers grafted therefrom and methods for grafting the polymers from surfaces (i.e., polymers grafted from a surface). As used herein, the term, "grafted therefrom" or "grafted from" refers to polymers that are prepared by polymerizing monomers from polymerization initiators associated with the particle surface. In certain embodiments, the polymers are grafted from surfaces to which a polymerization initiator has been adhered through an adhesive group.

In one embodiment, representative zwitterionic polymers grafted from a particle surface have formula (I):

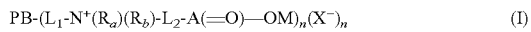

wherein PB is the polymer backbone having n pendant groups $L_1\text{-}N^+(R_a)(R_b)\text{-}L_2\text{-}A(=O)\text{--}OM$); $N^+$ is the cationic center; $R_a$ and $R_b$ are independently optional as necessary to provide a cationic center and independently selected from alkyl and aryl; $A(=O)\text{--}OM$ is the anionic center, where M is a counterion and A is C, S, SO, P, or PO; $L_1$ is a linker that covalently couples the cationic center to the polymer backbone; $L_2$ is a linker that covalently couples the cationic center to the anionic center; $X^-$ is the counter ion associated with the cationic center; and n is an integer from 1 to about 10,000.

In another embodiment, representative zwitterionic polymers grafted from a particle surface have formula (II):

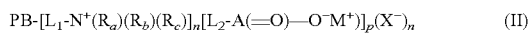

wherein PB, $L_1$, $R_a$, $R_b$, $L_2$, $A(=O)O^-$, $M^+$, $X^-$, and n are as described above, and $R_c$, is as for $R_a$ and $R_b$, and p is an integer from 1 to about 10,000.

In the above formulas, PB is the polymer backbone. Representative polymer backbones include vinyl backbones (i.e., $\text{--}C(R')(R'')\text{--}C(R''')(R'''')\text{--}$, where R', R'', R''', and R'''' are independently selected from hydrogen, alkyl, and aryl) derived from vinyl monomers (e.g., acrylate, methacrylate, acrylamide, methacrylamide, styrene). In one embodiment, the polymer backbone comprises $\text{--}[CH_2\text{--}C(R_d)]_n\text{--}$, wherein $R_d$ is selected from the group consisting of hydrogen, fluorine, trifluoromethyl, and C1-C6 alkyl, and n is from 1 to about 10,000.

For the polymers, the degree of polymerization (DP or n), number average molecular weight ($M_n$), and the ratio of weight average and number average molecular weights ($M_w/M_n$), also known as polydispersity index, can vary. In one embodiment, the polymers have a degree of polymerization (n) from 1 to about 10,000. In one embodiment, n is from about 10 to about 5,000. In another embodiment, n is from about 100 to about 3,500. In one embodiment, the polymers have a number average molecular weight ($M_n$) of from about 200 to about 200,000. In one embodiment, $M_n$ is from about 2,000 to about 100,000. In another embodiment, $M_n$ is from about 20,000 to about 80,000. In one embodiment, the polymers of have a ratio of weight average and number average molecular weight ($M_w/M_n$) of from about 1.0 to about 2.0. In one embodiment, $M_w/M_n$ is from about 1.1 to about 1.5. In another embodiment, $M_w/M_n$ is from about 1.2 to about 2.0.

In the above formulas, $N^+$ is the cationic center. In certain embodiments, the cationic center is a quaternary ammonium (e.g., N bonded to $L_1$; $R_a$, $R_b$, and $L_2$). In addition to ammonium, other useful cationic centers include imidazolium, triazaolium, pyridinium, morpholinium, oxazolidinium, pyrazinium, pyridazinium, pyrimidinium, piperazinium, and pyrrolidinium. In these embodiments, $R_a$ and $R_b$ are absent because the four valencies of the positively-charged nitrogen are taken up by the ring structure of the cationic center and bonds to $L_1$ and $L_2$. In another embodiment, the cationic center is a phosphonium center.

When present, $R_a$, $R_b$, and/or R, are independently selected from hydrogen, alkyl, and aryl groups. Representative alkyl groups include C1-C5 straight chain and branched alkyl groups. In certain embodiments, the alkyl group is further substituted with one of more substituents including, for example, an aryl group (e.g., $\text{--}CH_2C_6H_5$, benzyl). In one embodiment, $R_a$ and $R_b$ are methyl. Representative aryl groups include C6-C12 aryl groups including, for example, phenyl.

In the above formulas, $L_1$ is a linker that covalently couples the cationic center to the polymer backbone. In certain embodiments, $L_1$ includes a functional group (e.g., ester or amide) that couples the remainder of $L_1$ to the polymer backbone. In addition to the functional group, $L_1$ can include an C1-C10 alkylene chain. Representative $L_1$ groups include $\text{--}CO(=O)\text{--}(CH_2)_n\text{--}$ and $\text{--}C(=O)NH\text{--}(CH_2)_n\text{--}$, where n is 1-10 (e.g., 2 or 3). In one embodiment, n is 2. In one embodiment, n is 3.

In the above formulas, $L_2$ is a linker that covalently couples the cationic center to the anionic center. $L_2$ can be a C1-C25 alkylene chain. Representative $L_2$ groups include $\text{--}(CH_2)_n\text{--}$, where n is 1-5. In one embodiment, n is 2. In one embodiment, n is 3.

In the above formulas, $A(=O)\text{--}OM$ is the anionic center, where A is C, S, SO, P, or PO. The anionic center is an acid. M is counterion ion. Representative counterions include metals ions (e.g., lithium sodium, potassium, calcium, magnesium), nitrogen-containing ions (e.g., ammonium, imidazolium, triazolium, pyridinium), and organic ions.

In the above formulas, $X^-$ is the counter ion associated with the cationic center. The counter ion can be the counter ion that results from the synthesis of the polymers (e.g., $Cl^-$, $Br^-$, $I^-$). The counter ion that is initially produced from the synthesis of the cationic center can also be exchanged with other suitable counter ions to provide polymers having controllable hydrolysis properties and other biological properties. Representative counter ions include halides; carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N(SO_2CF_3)_2$); and derivatives thereof. Other counter ions also can be chosen from sulfate, nitrate, perchlorate ($ClO_4$), tetrafluoroborate ($BF_4$), hexafluorophosphate ($PF_6$), trifluoromethylsulfonate ($SO_3CF_3$), bis(trifluoromethylsulfonyl)amide, lactate, salicylate, and derivatives thereof.

In another aspect, the invention provides a method for making a particle surface having zwitterionic polymers grafted therefrom. In the method, a radical initiator terminated monolayer is formed on a particle surface. The radical initiator comprises one or more groups effective to adhere the initiator to the surface. A zwitterionic monomer is then polymerized on the radical initiator terminated monolayer to provide a surface having zwitterionic polymers grafted therefrom.

In one embodiment, zwitterionic polymers are grafted from self-assembly monolayers (SAMs) terminated with initiators through atom transfer radical polymerization (ATRP) by polymerization of suitable zwitterionic monomers. In the process, the particle surface is coated with the SAMs terminated with radical initiator followed by zwitterionic monomer polymerization onto the SAMs to form a zwitterionic polymer coating on the particle surface. The atom transfer radical polymerization is initiated by the radical initiator at the terminus of the SAMs.

The radical terminated SAMs can be formed by a one-step or a two-step method. In a one-step method, an initiator SAM is formed by attaching radical initiator-terminated molecules to the particle surface through interaction with the radical initiator's attaching group. In a two-step method, a functional group-terminated SAM is formed by attaching functional group-terminated molecule to the surface through covalent or noncovalent bonding. The functional group-terminated SAM is subsequently converted to the initiator-terminated SAM by chemical reaction.

Suitable polymerization methods include atom transfer radical polymerization (ATRP), reversible addition fragmentation chain transfer (RAFT) polymerization, and free radical polymerization. Any conventional radical initiators for polymerization may be used to practice the invention. The representative initiators for normal thermal or photochemical free radical polymerization include benzoyl peroxide, 2,2'-azo-bis(2-methylproionitrile) and benzoin methyl ether. Representative initiators for ATRP include alkyl halides, such as bromoisobutyryl bromide (BIBB). Representative initiators for RAFT polymerization (i.e., free radical initiators with chain reversible agency (CTA)) include thiocarbonylthio compounds.

As noted above, in the grafted from method, the radical initiator terminated monolayer formed on a particle surface comprises a radical initiator that includes one or more groups effective to adhere the initiator to the surface.

In one embodiment, the radical initiator comprises one or more dihydroxyphenyl groups effective to adhere the initiator to the particle surface. A zwitterionic monomer is then polymerized on the radical initiator terminated monolayer to provide a surface having zwitterionic polymers grafted therefrom.

As noted above, in the grafted from method, the radical initiator terminated monolayer formed on a particle surface comprises a radical initiator that includes one or more dihydroxyphenyl groups effective to adhere the initiator to the surface. In one embodiment, representative radical initiators of the invention have formula (III):

$$(DHP)_m\text{-}L_4\text{-}NH\text{—}C(\!=\!O)\text{—}C(CH_3)_2\text{—}Br \tag{III}$$

wherein $L_4$ is a linker moiety that covalently couples the m dihydroxyphenyl (DHP) groups to the amide nitrogen (m is an integer from 1 to 20, for example, 1, 2, 3, or 4). Linker moiety $L_4$ can include up to about 20 atoms.

In one embodiment, zwitterionic monomers useful in the invention have formula (IV):

$$CH_2\!=\!C(R_d)\text{-}L_1\text{-}N^+(R_a)(R_b)\text{-}L_2\text{-}A(\!=\!O)\text{—}OM\ X^- \tag{IV}$$

wherein $L_1$, $N^+$, $R_a$, $R_b$, $A(\!=\!O)OM$, and $L_2$, and $X^-$ are as described above for the zwitterionic polymers, and $R_d$ is selected from the group consisting of hydrogen, fluorine, trifluoromethyl, and C1-C6 alkyl.

Methods for making carboxybetaine and sulfobetaine polymers and their uses described in WO 2007/024393, expressly incorporated herein by reference in its entirety.

The preparation and characterization of representative zwitterionic polymer coated particles, silica nanoparticles, having the polymer grafted from the particle surface is described in Example 1.

The preparation and characterization of representative zwitterionic polymer coated particles, gold nanoparticles, are described in Example 2.

Particle Surfaces Having Zwitterionic Polymers Grafted Thereto

In another aspect, the invention provides particle surfaces having zwitterionic polymers grafted thereto and methods for grafting the polymers to particle surfaces (i.e., polymers grafted to the surface). As used herein, the term "grafted thereto" or "grafted to" refers to polymers that are first prepared and then associated with a particle surface, which is in contrast to polymers grafted from a particle surface.

Zwitterionic polymers suitable for grafting to particle surfaces include one or more adhesive groups. In one embodiment, the adhesive group is a dihydroxyphenyl group.

Representative zwitterionic polymers useful for grafting to particle surfaces have formula (V):

$$(DHP)_m\text{-}L_3\text{-}PB\text{-}(L_1\text{-}N^+(R_a)(R_b)\text{-}L_2\text{-}A(\!=\!O)\text{—}OM)_n$$
$$(X^-)_n \tag{V}$$

wherein DHP, $L_3$, PB, $L_1$, $N^+$, $R_a$, $R_b$, $A(\!=\!O)OM$, m, n, and $X^-$ are as described above.

In one embodiment, the dihydroxyphenyl group is a 3,4-dihydroxyphenyl group (i.e., a catechol group). In certain embodiments, the polymer includes a 3,4-dihydroxyphenyl group derived from 3,4-dihydroxyphenyl alanine (i.e., DOPA). In one embodiment, m is 1 and, in another embodiment, m is 2. In formula (I), $L_3$ is a linker moiety that covalently couples the m dihydroxyphenyl groups to the polymer backbone. The linker moiety is a group of atoms that is effective to covalently couple the m dihydroxyphenyl groups to the polymer backbone.

In another aspect, the invention provides methods for treating particle surfaces with the polymers (i.e., polymers grafted to a surface). In the methods, a particle surface is treated with a polymer by applying the polymer to the surface or contacting the surface with the polymer. In one embodiment, applying the polymer to the surface comprises contacting a surface with a solution comprising the polymer. In one embodiment, applying the polymer to the surface comprises flowing a solution comprising the polymer over the surface.

Conditions for effectively adhering the polymers depend on the nature of the polymer and the particle surface to which the polymer is to be adhered. In certain embodiments, effective adhesion of the polymer to the surface involves presenting the polymer's adhesive group to the surface. Presenting the adhesive group to the surface can involve using a polymer solution or composition that allows the polymer to assume a conformation that reveals or exposes the adhesive group for binding to the surface (e.g., extends the polymer away from the adhesive group).

Compositions for adhering a polymer to a surface include the polymer and a solvent. Suitable solvents include aqueous solvents, organic solvents, and combinations thereof. Representative aqueous solvents include aqueous buffers such as MOPS, Tris, and PBS buffers. Representative organic solvents include acetone, acetonitrile, methanol, ethanol, isopropanol, n-propanol, dimethylformamide, dimethylsulfoxide, tetrahydrofuran, and trifluoroethanol. Representative combinations of aqueous and organic solvents include organic solvents that are miscible in water. Suitable water-miscible organic solvents include acetone, acetonitrile, methanol, ethanol, isopropanol, n-propanol, dimethylformamide, dimethylsulfoxide, tetrahydrofuran, and trifluoroethanol. Suitable compositions include water and water-miscible solvents combined in a ratio of from about 1:20 v/v to about 20:1 v/v. In one embodiment, the surface is contacted with a polymer in a MOPS buffer. In one embodiment, the surface is contacted with a polymer in a Tris buffer. In one embodiment, the surface is contacted with a polymer in aqueous tetrahydrofuran (e.g., THF:water, 1:2).

The pH of the polymer composition can affect the effectiveness of polymer adhesion to a surface. For carboxybetaine polymers, the pH is from about 2 to about 10. For sulfobetaine polymers, the pH is from about 1 to about 12.

The preparation and characterization of representative zwitterionic polymer coated particles, magnetic iron oxide nanoparticles, are described in Example 3.

Targeting Agents

Particles useful for therapeutic and diagnostic purposes can be advantageously treated with the polymers of the invention. In certain embodiments, the surface further comprises a plurality of target binding partners covalently coupled to a portion of the plurality of polymers adhered to the surface. In this embodiment, the target binding partner has affinity toward a target molecule. In these embodiments, the surfaces can be used in diagnostic assays.

The binding affinity of a target molecule toward to the surface results from the target binding partners immobilized on the surface. The target binding partner and the target molecule, each termed a binding pair member, form a binding pair. Each binding pair member is a molecule that specifically binds the other member. In one embodiment, the target binding partner has affinity to a target molecule with $K_d$ less than about $10^{-8}$.

A binding pair member can be any suitable molecule including, without limitation, proteins, peptides, proteins, poly- or oligo-saccharides, glycoproteins, lipids and lipoproteins, and nucleic acids, as well as synthetic organic or inorganic molecules having a defined bioactivity, such as an antibiotic, anti-inflammatory agent, or a cell adhesion mediator.

Examples of proteins that can be immobilized on the surfaces of the present invention include ligand-binding proteins, lectins, hormones, receptors, and enzymes. Representative proteins include antibodies (monoclonal, polyclonal, chimeric, single-chain or other recombinant forms), their protein/peptide antigens, protein-peptide hormones, streptavidin, avidin, protein A, proteins G, growth factors and their respective receptors, DNA-binding proteins, cell membrane receptors, endosomal membrane receptors, nuclear membrane receptors, neuron receptors, visual receptors, and muscle cell receptors. Representative oligonucleotides that can be immobilized on the surfaces of the present invention include DNA (genomic or cDNA), RNA, antisense, ribozymes, and external guide sequences for RNase P, and can range in size from short oligonucleotide primers up to entire genes.

Other target binding partners that bind specifically to a target compound include poly- or oligosaccharides on glycoproteins that bind to receptors, for example, the carbohydrate on the ligand for the inflammatory mediators P-selectin and E-selectin, and nucleic acid sequences that bind to complementary sequences, such as ribozymes, antisense, external guide sequences for RNase P, and aptamers.

In one embodiment, the target binding partner is an antibody, and the target molecule is an antigen against the antibody. In this embodiment, the surface of the invention specifically binds to the antigen and resists non-specific protein adsorption. In one embodiment, the target binding partner is a protein capable of promoting cell adhesion, and the target molecule is a cell. In this embodiment, the surface of the invention specifically binds to the cell and resists non-specific protein adsorption and non-specific cell adhesion.

The use of carboxybetaine polymer surfaces for immobilizing target binding partners is described in WO 2008/083390, expressly incorporated herein by reference in its entirety.

The following is a description of representative zwitterionic coated nanoparticles of the invention, their preparation, characterization, and advantageous uses.

Zwitterionic Polymer Coated Silica Particles

Surface Modification of Silica Nanoparticles.

There is a difference expected in the size before and after surface modification. The results determined by dynamic light scattering (DLS), including the particle size and polydispersity index (PDI), are listed in Table 1.

TABLE 1

Results of dynamic light scattering measurements of silica nanoparticles.

| Sample | $d^c$ (nm) | Polydispersity index$^d$ |
|---|---|---|
| Bare SiP$^a$ | 66 | 0.047 |
| Initiator-coated SiP$^a$ | 74.1 | 0.053 |
| PolyCBAA-SiP1$^b$ | 135.5 | 0.118 |
| PolyCBAA-SiP2$^b$ | 221.3 | 0.172 |

$^a$Measured in ethanol.
$^b$Measured in water.
$^c$Average hydrodynamic diameter.
$^d$Based on the cumulant method.

As can be seen from Table 1, there is an increase in size by 8 nm (from 66 nm to 74.1 nm) after silane modification. This indicates that the initiator was successfully anchored onto the surfaces of the nano silica particles. The sizes of the representative particles increase to around 135.5 (polyCBAA-SiP1) and 221.3 nm (polyCBAA-SiP2) after polyCBAA polymerization for 12 h and 24 h, respectively. This significant increase in the average hydrodynamic diameter of the nanoparticles from DLS measurements confirmed the presence of the polyCBAA shell on the nanoparticles. Furthermore, the size distribution is quite narrow (all PDI is lower than 0.2), indicating the high stability of the nanoparticles during the experimental process.

Figure 1B:
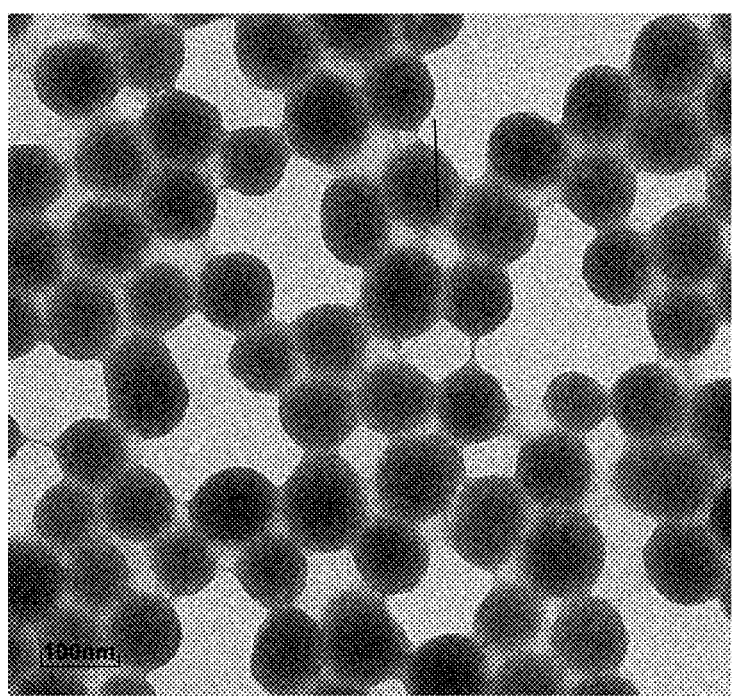

FIG. 1 displays the TEM images of polyCBAA-SiP1 (Table 1) and particles before polyCBAA coating. Compared with the pre-coated nanoparticles (a), the boundaries among the coated particles become unclear. This is due to the fused polymer shell under the measurement condition of TEM (voltage 200 KV). This further confirmed that polyCBAA polymers were incorporated on the surface of the nanoparticles. In addition, due to the hydration layer in solution, the sizes determined from TEM in FIG. 1 are slightly smaller than those determined from DLS in Table 1.

Stability in Protein Solution.

To evaluate the stability of nanoparticles in protein solutions, DLS is used to track the size change of the nanoparticles during their incubation in protein solutions. Lysozyme and bovine serum albumin, representative of positively and negatively charged proteins at neutral pH, were chosen for protein binding tests. Stability of the polyCBAA coated silica nanoparticles was tested in 10 mg/mL protein/PBS solution and incubated at room temperature. After nanoparticles are added, transparent protein solutions changed to light blue because of the light scattering of the nanoparticles.

Figure 2:
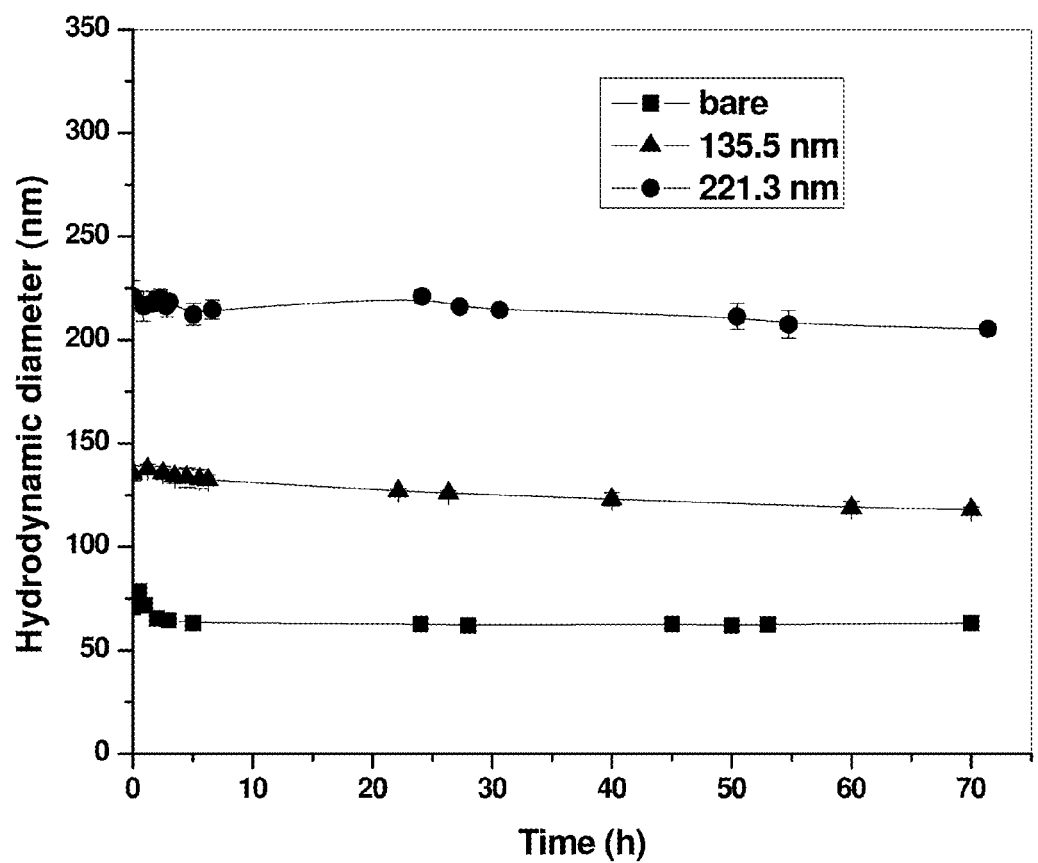
FIG. 2 compares hydrodynamic diameter change of uncoated (bare) silica nanoparticles to representative zwitterionic polymer coated silica particles of the invention, polyCBAA-SiP (135.5 and 221.3 nm) in BSA/PBS solution (10 mg/mL).
Figure 3:
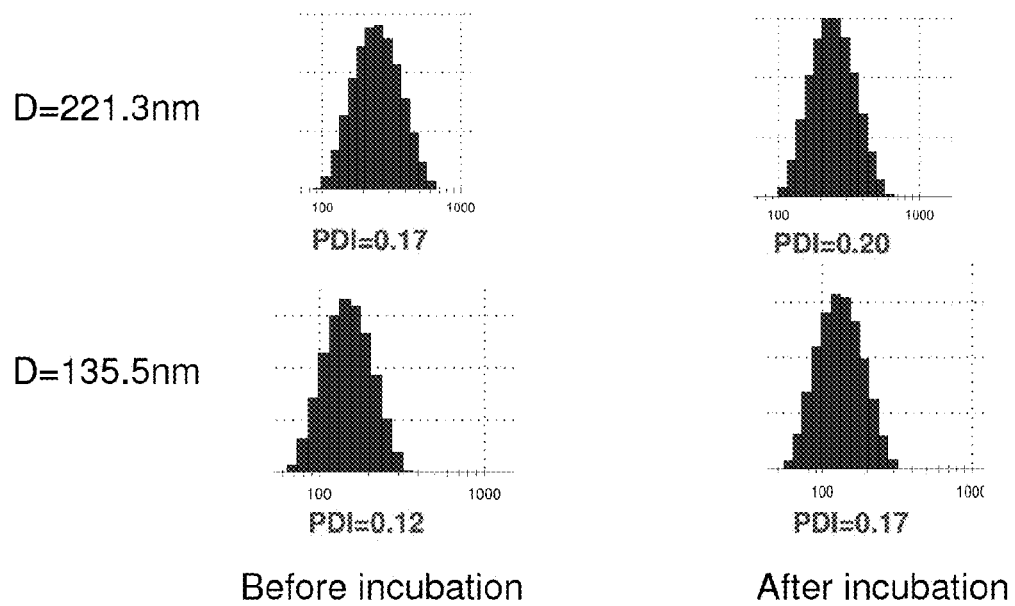
FIG. 3 compares the polydispersity indexes (PDI) of representative zwitterionic polymer coated silica particles of the invention, polyCBAA-SiP (135.5 and 221.3 nm) before and after incubation in BSA/PBS solution (10 mg/mL).

FIG. 2 shows the hydrodynamic diameters of the bare nanoparticles and nanoparticles coated with polyCBAA in 10 mg/ml BSA/PBS solution. All the particles show excellent stability without obvious size increase during a 72 hours incubation period. Moreover, the size distribution of the nanoparticles after incubation is similar to that before incubation (see FIG. 3). This indicates that polyCBAA indeed offers a robust coating around the silica nanoparticles, protecting them against aggregation in complex physiological conditions. It is well known that the bare silica nanoparticles carry negative charge on their surface at neutral pH. Thus, there are repulsive interactions between the silica surface and the negative BSA. This is why the bare silica nanoparticles are also stable for a long time in the BSA solution.

Figure 4:
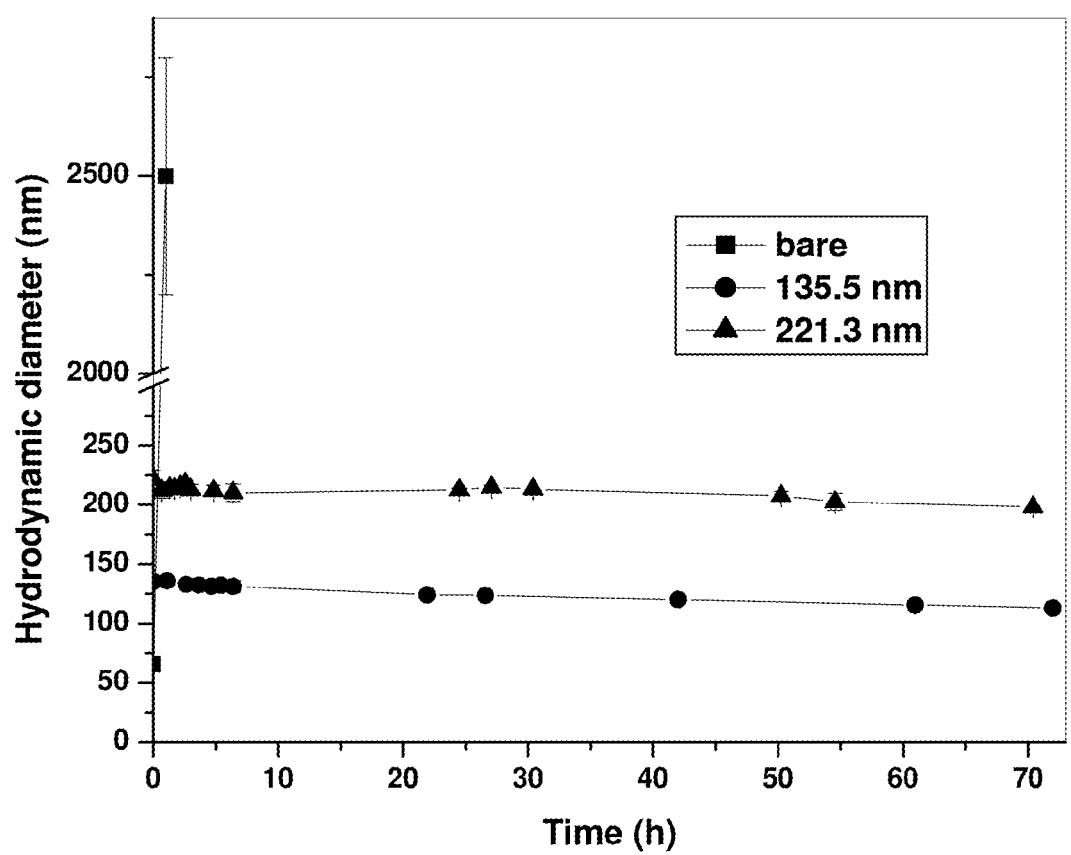
FIG. 4 compares hydrodynamic diameter change of uncoated (bare) silica nanoparticles to representative zwitterionic polymer coated silica particles of the invention, polyCBAA-SiP (135.5 and 221.3 nm) in Lyz/PBS solution (10 mg/mL).
Figure 5:
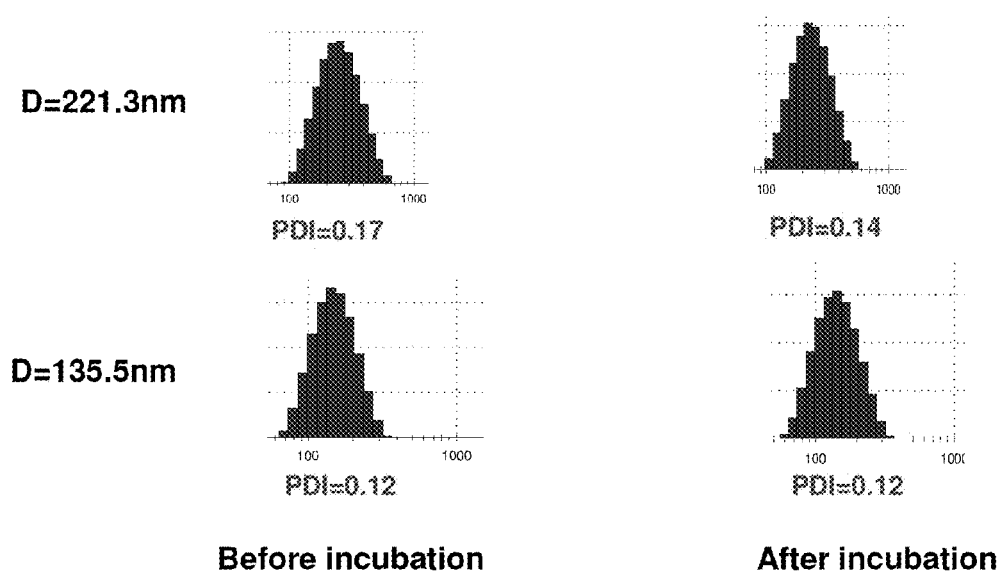
FIG. 5 compares the polydispersity indexes (PDI) of representative zwitterionic polymer coated silica particles of the invention, polyCBAA-SiP (135.5 and 221.3 nm) before and after incubation in Lyz/PBS solution (10 mg/mL).

The size change of the bare and coated nanoparticles in Lyz/PBS solution was shown in FIG. 4. As can be seen from FIG. 4, two representative polyCBAA coated nanoparticles show excellent stability during the 72 hour incubation. The similar size distribution before incubation and after incubation in FIG. 5 provides further evidence for the stability of the coated nanoparticles in the Lyz/PBS solution. Due to the negative surface and its attraction to positively charged Lyz, bare silica nanoparticles formed white precipitate when exposed to the Lyz/PBS solution. The excellent stability of polyCBAA coated nanoparticles in both negative and positive protein solution shows that polyCBAA layer is highly effective to protect silica nanoparticles from nonspecific protein binding.

Functionalization.

To test the functionalization of these particles, preliminary experiments were carried out. After activated in a fresh prepared solution of NHS (0.05M) and EDC (0.2 M) in MilliQ water (pH of the final NHS/EDC solution was about 5.5), the polyCBAA-SiP1 nanoparticles were re-dispersed in the solution of anti-ALCAM with a concentration at 50 μg/mL in 10 mM sodium borate buffer (pH~8.5). DLS results showed that the size of functionalized particles is 166 nm, as compared with bare polyCBAA-SiP1 of 135.5 nm. A 30 nm increase in diameter was observed after functionalization. This is equivalent to the size of two antibodies in diameter, indicating successful antibody immobilization. Therefore, the presence of the multifunctional polyCBAA shell makes these particles to be easily functionalized.

In summary, zwitterionic polyCBAA was used to prepare biocompatible and functionalizable silica nanoparticles via silane chemistry. The modified silica nanoparticles with two different thicknesses of polyCBAA are stable at least 72 hours in both negative and positive protein solutions, demonstrating the high efficiency of the polyCBAA layers to improve the biointerfacial properties of silica nanoparticles. Moreover, abundant functional groups in polyCBAA make these coated particles to be easily functionalized for future applications in targeted drug delivery vehicle and diagnostics.

Zwitterionic Polymer Coated Gold Particles

Structure of CBAA Monomer and pCBAA-GNPs.

Figure 6:
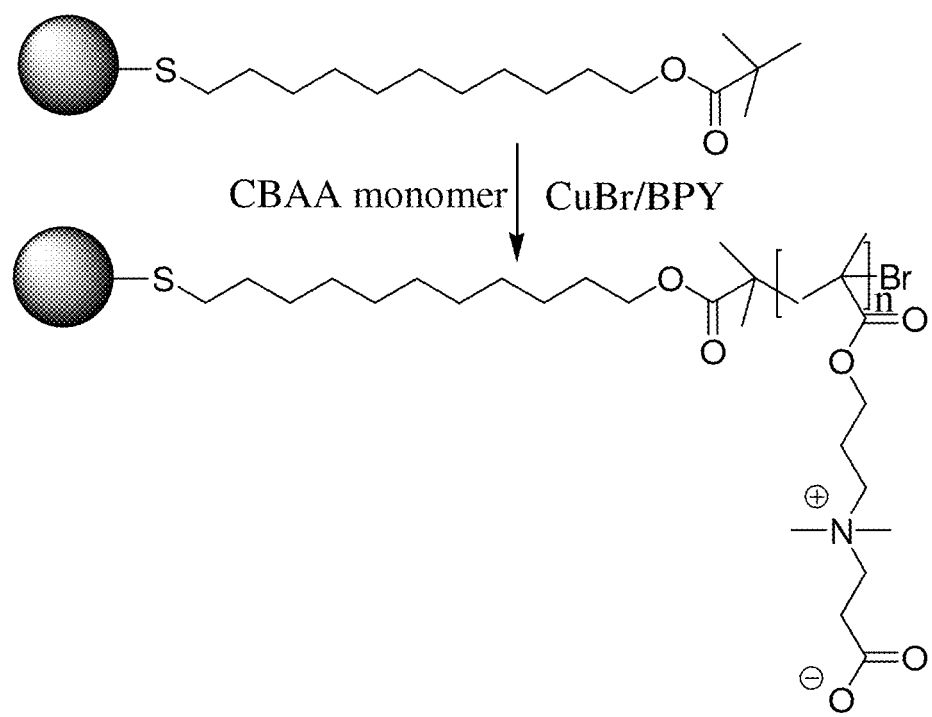
FIG. 6 is a schematic illustration of grafting a representative zwitterionic polymer of the invention, polyCBAA, onto a GNP surface covered with initiators via surface-initiated ATRP.
Figures 7A, 7B, 7C:
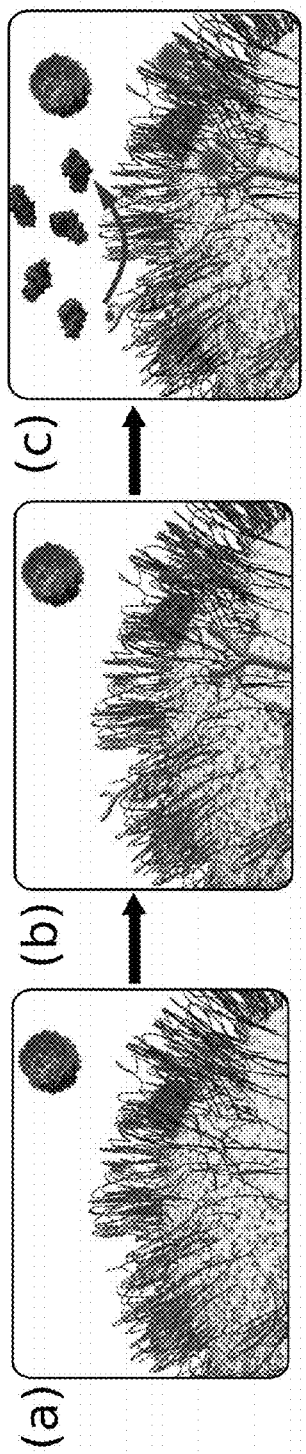
FIGS. 7A-7C are illustrations of representative zwitterionic polymer particles of the invention, polyCBAA-coated GNPs, presenting an abundance of functional groups for ligand immobilization in an ultra-low fouling background: PolyCBAA-coated GNPs (pCBAA-GNPs) (7A); PCBAA-GNPs immobilized with antibodies (7B); and PolyCBAA surfaces are highly resistant to nonspecific protein adsorption after antibody immobilization (7C).
Figure 8:
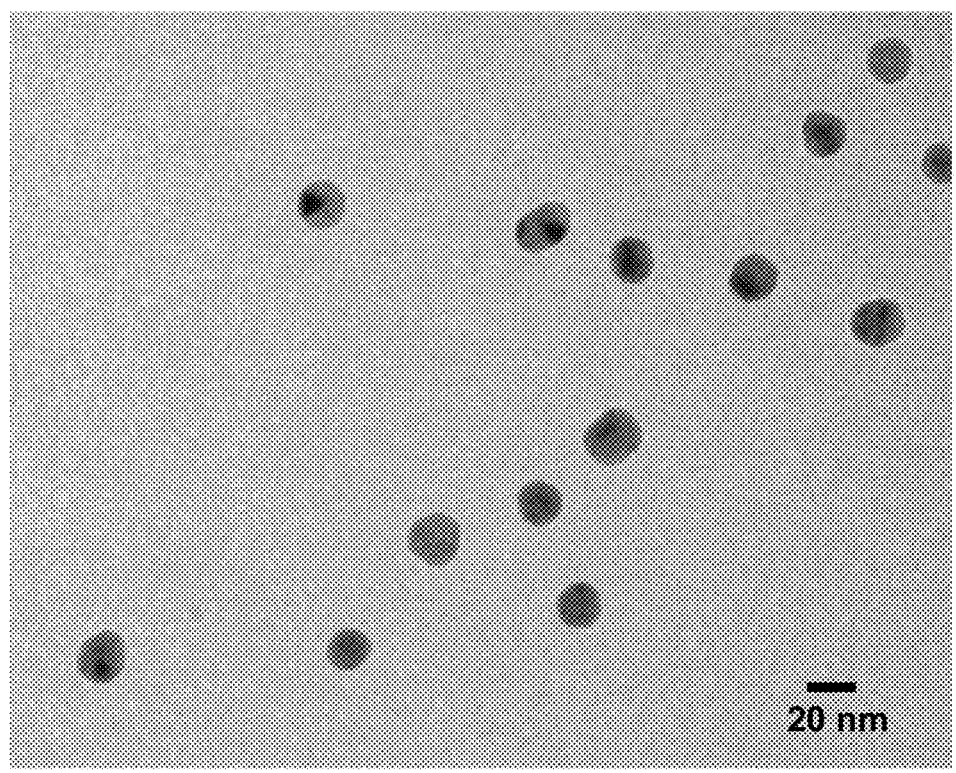
FIG. 8 is a TEM image of representative zwitterionic polymer particles of the invention, polyCBAA coated GNPs (pCBAA-GNPs).

The structure of CBAA monomer is shown in FIG. 6. PCBAA-GNPs, as illustrated in FIG. 7 were synthesized via ATRP method, transmission electron microscope (TEM) image of small pCBAA-GNPs (as shown in FIG. 8) showed the monodisperse nanoparticles without any aggregated structures. The average diameter of GNPs cores was 18.5 nm. The hydrodynamic diameter of pCBAA-GNPs conjugates measured by dynamic light scattering (DLS) showed an average diameter of 58.4 nm, indicating that the pCBAA coating thickness was around 20 nm.

Stability of Bare Polymer-Coated GNPs in Salt and Common Protein Solutions.

The stability of bare GNPs, PEG-GNPs, OEGMA-GNPs and pCBAA-GNPs with two different sizes were first evaluated in 1 mg·ml$^{-1}$ lysozyme (14 kD, pI=12) solution and 20% NaCl solution. UV-vis spectroscopy was applied to examine nonspecific protein adsorption onto the surface of these nanoparticles or salt effect on their stability. Aggregation of colloid particles and/or protein adsorption on their surface will result in a shift in the surface plasmon absorption. Results showed (see Table 2), after mixing with lysozyme or NaCl solution, the plasmon resonance peak of bare GNPs had a dramatically red shift. Only a slightly shift was observed for PEG-GNPs and OEGMA-GNPs, whereas the peak was the same for pCBAA-GNPs of two different sizes. This indicates that pCBAA-GNPs were intact. Dynamic light scattering (DLS) was also applied to test their stability. The hydrodynamic size of PEG-GNPs and OEGMA-GNPs in water were 53.4 nm and 74.3 nm, respectively. But, after the addition of lysozyme or NaCl solution, nanoparticles showed an increase of about 20 nm in size compared to those in water. In the case of pCBAA-GNPs, their diameters did not change, indicating the high in vitro stability of pCBAA-GNPs in high ionic strength or in the presence of proteins under physiological conditions.

TABLE 2

Plasmon resonance peak and hydrodynamic size of bare and polymer-coated GNPs after they are mixed with water, 20% NaCl and 1 mg · ml$^{-1}$ lysozyme solutions.

| | Plasmon resonance peak (nm) | | | Hydrodynamic size (nm) | | |
|---|---|---|---|---|---|---|
| | H$_2$O | 1 mg · ml$^{-1}$ lysozyme | 20% NaCl | H$_2$O | 1 mg · ml$^{-1}$ lysozyme | 20% NaCl |
| Bare GNPs | 523.2 ± 0.3 | 580.8 ± 0.2 | 697.4 ± 0.1 | 18.5 ± 1.4 | 160.2 ± 1.1 | 387.7 ± 0.5 |
| PEG-GNPs | 527.7 ± 0.1 | 530.0 ± 0.1 | 530.2 ± 0.2 | 53.4 ± 1.3 | 85.0 ± 0.4 | 77.3 ± 3.0 |
| OEGMA-GNPs | 534.1 ± 0.1 | 534.9 ± 0.4 | 538.3 ± 0.2 | 74.3 ± 1.4 | 93.1 ± 1.1 | 91.2 ± 3.6 |

TABLE 2-continued

Plasmon resonance peak and hydrodynamic size of bare and polymer-coated GNPs after they are mixed with water, 20% NaCl and 1 mg · ml$^{-1}$ lysozyme solutions.

| | Plasmon resonance peak (nm) | | | Hydrodynamic size (nm) | | |
|---|---|---|---|---|---|---|
| | $H_2O$ | 1 mg · ml$^{-1}$ lysozyme | 20% NaCl | $H_2O$ | 1 mg · ml$^{-1}$ lysozyme | 20% NaCl |
| Small pCBAA-GNPs | 532.2 ± 0.1 | 532.2 ± 0.1 | 532.2 ± 0.1 | 58.4 ± 1.7 | 58.9 ± 1.4 | 57.2 ± 0.4 |
| Large pCBAA-GNPs | 568.0 ± 0.1 | 568.0 ± 0.1 | 568.0 ± 0.1 | 105.9 ± 3.0 | 105.5 ± 0.4 | 105.8 ± 3.4 |

Stability of and Bare Polymer-Coated GNPs in 10% and 100% Serum Solution.

Figure 9A:
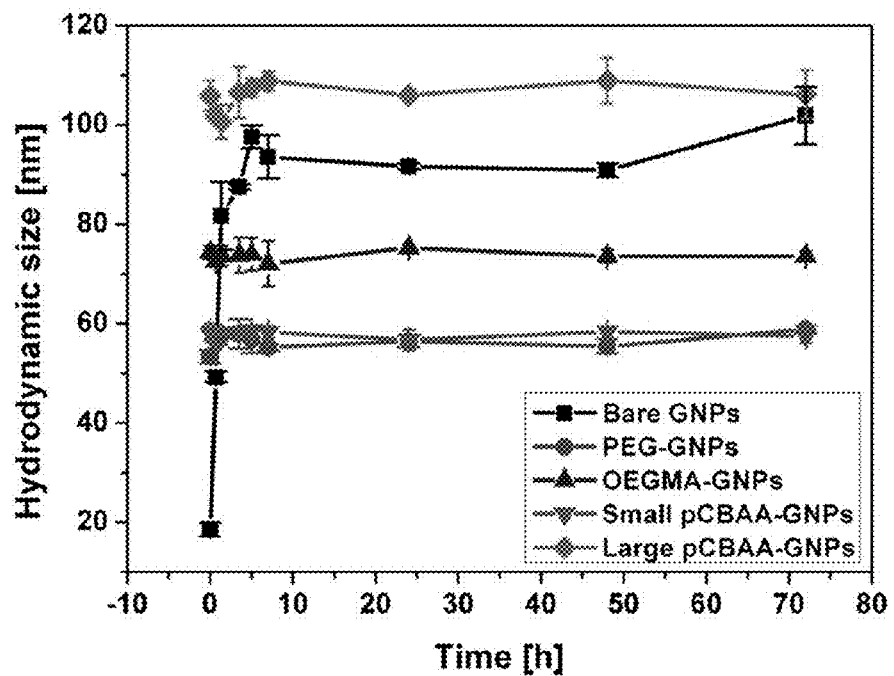
FIGS. 9A and 9B compare hydrodynamic size of GNPs coated with different polymers along with bare GNPs in complex media: bare GNPs and polymer-coated GNPs in 10% blood serum (PBS) (9A); and bare GNPs and polymer-coated GNPs in 100% blood serum (9B). These GNPs were separated from serum and re-suspended in buffer before detection.

The stability of bare GNPs and polymer-coated GNPs was further evaluated in PBS plus 10% human blood serum. FIG. 9A shows the hydrodynamic diameters of bare GNPs and GNPs coated with different polymers in PBS plus 10% human blood serum. Previous studies have shown that the addition of serum increases the stability of the unmodified particles due to nonspecific protein adsorption. Referring to FIG. 9A, after 1 h, the bare GNPs showed an increase of about 60 nm in size. This value increased to 80 nm after 72 h, which was attributed to the interactions of nanoparticles with proteins in the incubation serum medium. However, with polymers coatings, there is no agglomeration and all four samples showed good stability without obvious size increase during the test period of 72 h.

Figure 9B:
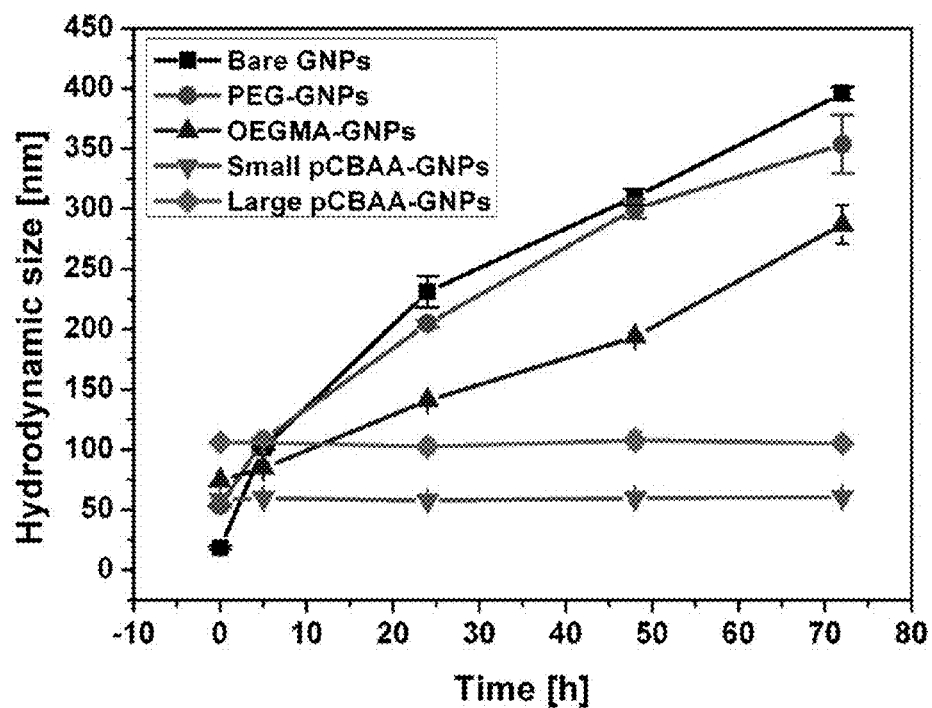

Protein adsorption onto GNPs coated with different polymers in undiluted (100%) human blood serum was further studied. 100% serum is far more challenging than 10% serum. Due to high protein concentrations, these nanoparticles were separated from human blood serum proteins by centrifugation and re-dispersed in PBS buffer. The average diameter of the nanoparticles was then evaluated by DLS. As shown in FIG. 9B, bare GNPs showed a size increase of about 80 nm in a very short period of time. At the end of 72 h, the diameter increased to about 380 nm, indicating significant protein adsorption and particulate aggregation. PEG-GNPs and OEGMA-GNPs were not stable in such extreme situation either. Their diameter increments were 300 nm and 210 nm, respectively, after an incubation period of 72 h. Precipitates could be observed in the above solutions. However, with the protection of polyCBAA coating, the interactions between proteins and nanoparticles did not cause any agglomeration and the particle sizes after their separation from human blood serum proteins was almost the same as those without serum (58.4 and 105.9 nm), again indicating their excellent stability.

Figure 10:
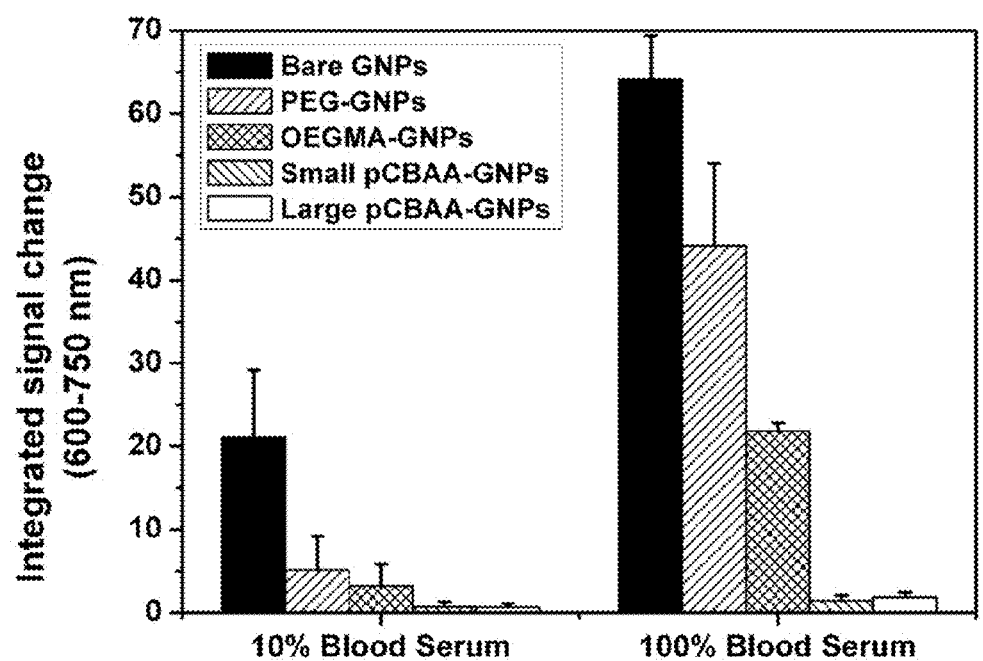
FIG. 10 compares the stability of gold nanoparticles in 10% and 100% serum from UV-vis spectroscopy. Serum induced-agglomeration was determined by measuring the red shift in the absorbance of nanoparticles after 72 h incubation. The absorbance was integrated from 600-750 nm.

The stability in 10% and 100% blood serum was also evaluated by UV-vis spectroscopy. Aggregation of gold nanoparticles results in a red-shifted absorbance profile. Therefore, aggregation was quantified by integrating particle absorbance from 600 nm to 750 nm (FIG. 10). After their incubation in 100% serum for 72 h, the integrated absorbance values of bare GNPs, PEG-GNPs and OEGMA-GNPs presented notable increases. The values in 100% serum are higher than that in 10% serum, which is consistent with the DLS data. Similar to DLS results in FIG. 9, pCBAA-GNPs were stable in 10% serum and 100% serum with integrated absorbance <2. Similar phenomena were observed previously on flat sensor surfaces. For example, despite the excellent nonfouling capabilities of short OEG self-assembled monolayers (SAMs) in single protein solutions and 10% human blood serum, they failed when exposed to complex media such as 100% human blood serum. Thus, 10% serum commonly used to evaluate the stability of nanoparticles is not sufficient and undiluted blood serum is recommended to screen nanoparticles before their in vivo experiments.

Functionalization of pCBAA-GNPs.

Figure 11:
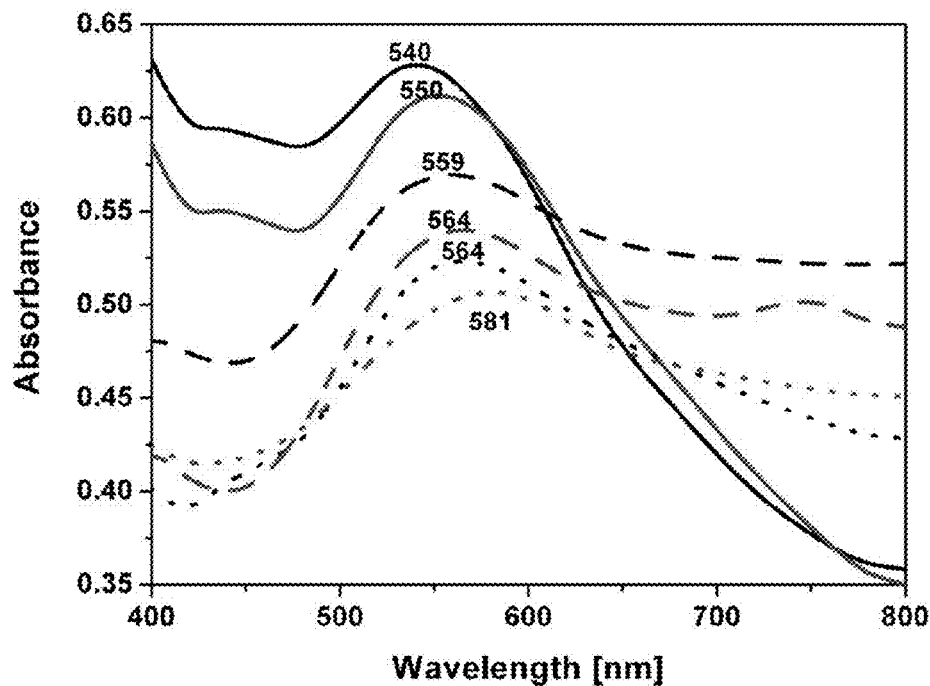
FIG. 11 compares UV-vis spectra of GNPs coated with different amounts of anti-ALCAM and their binding with different levels of ALCAM measured from 400 to 800 nm. Black and red lines represent pCBAA-GNPs functionalized with 2 and 25 µg·ml$^{-1}$ anti-ALCAM, respectively; solid, dash and dot lines represent pCBAA-GNPs functionalized with anti-ALCAM in the presence of 0, 10 and 25 µg·ml$^{-1}$ ALCAM, respectively.
Figure 12:
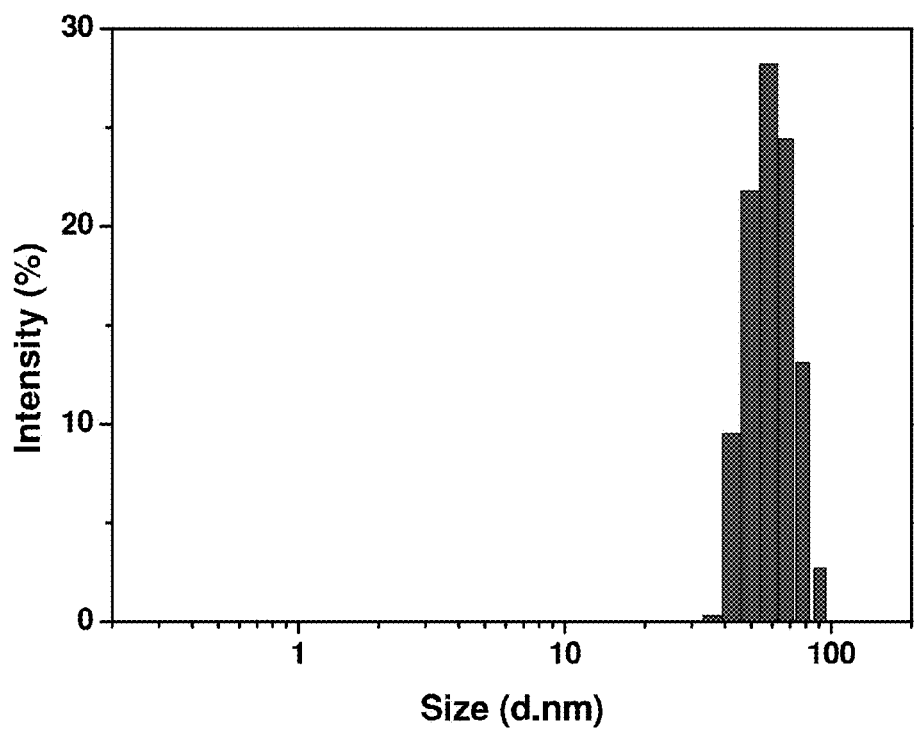
FIG. 12 illustrates the size distribution of representative zwitterionic polymer particles of the invention, polyCBAA coated GNPs (pCBAA-GNPs).

Besides the enhanced stability of GNPs in different environments, the polyCBAA coating also provided abundant functional groups for ligand immobilization. To demonstrate that antibody is immobilized onto GNPs and its immobilized density can be adjusted, antibody-coated pCBAA-GNPs with two immobilized antibody densities were probed by the targeted antigen. A candidate cancer biomarker (activated leukocyte cell adhesion molecule, ALCAM or CD 166) was applied as a model antibody. Polyclonal anti-ALCAM and ALCAM were employed because each polyclonal anti-ALCAM contains multiple ALCAM binding sites, by adding ALCAM, it is expected that anti-ALCAM-modified pCBAA-GNPs can aggregate, causing a red shift in the absorbance spectrum of the GNPs. As shown in FIG. 11, the degree of antigen-induced aggregation of nanoparticles increased with the concentration of antigen at a given antibody concentration, demonstrating that the ligand density on the surface of GNPs can be controlled. With the same antigen concentration, the degree of aggregation of nanoparticles increased with the antibody concentration. Therefore, antibody/antigen ligand density on GNPs can be easily controlled by the antibody/antigen concentration. Unreacted activated sites of polyCBAA can be converted back to nonfouling carboxylate anions groups via hydrolysis, ensuring the ultra-low fouling properties of post-functionalized surfaces in undiluted blood plasma and serum (as shown in FIG. 6C).

In summary, a functionalizable and stable surface platform for nanoparticles has been demonstrated. Results show that polyCBAA coated GNPs have superior performance in undiluted blood serum over GNPs with other conventional coatings including PEG, although their performance in 10% blood serum is comparable. This indicates that 10% serum commonly used to evaluate the stability of nanoparticles is not sufficient. Undiluted blood serum is recommended to screen nanoparticles before in vivo experiments. This new criterion will allow one to screen NPs effectively before in vivo experiments and save unnecessary in vivo experiments. Furthermore, bio-recognition elements such as anti-ALCAM can be easily conjugated to polyCBAA via NHS/EDC method. There are many more functional groups available for ligand immobilization onto polyCBAA. Ligand immobilization density can be varied by adjusting antibody/antigen concentrations. The uniqueness of polyCBAA (i.e., ultra low fouling and multiple functionalities) makes this zwitterionic biopolymer useful for nanoparticle coatings for in vivo targeting drug delivery and diagnostics.

Zwitterionic Polymer Coated Iron Oxide (Magnetic) Particles

Magnetic nanoparticles (MNPs) have many attractive properties, often combining low toxicity with excellent magnetic properties. Recently, "theranostics", which incorporate both therapy and diagnosis, are attracting significant attention and may revolutionize current medical treatments. To achieve this goal, MNPs can work as multifunctional carriers to selectively accumulate at the target site, cure disease by certain mechanisms (either hyperthermia or drug release) and be detected using non-invasive diagnosis modality such as magnetic resonance imaging (MRI). Multifunctional MNPs can typically be formed from magnetic cores and surface coating. Magnetic cores are iron oxide nanoparticles which are detectable by MRI and can be manipulated by a magnetic field, while an ideal surface coating can carry a therapeutic reagent, prevent MNPs from being cleared from the blood circulation, and provide functional groups for conjugation of targeting ligands. Thus, the surface coating plays a key role in achieving multifunctional MNPs.

As described above, surfaces coated with zwitterionic polymers can be prepared via atom transfer radical polymerization (ATRP) to achieved surface coatings with excellent ultra low fouling properties. This process provides surfaces in which the polymer is grafted from the surface (referred to as the "graft-from-surface" method). However, ATRP reactions require surface-grafted initiators, catalysts, and oxygen-free conditions which limit its practical application. The present invention provides an alternative method, in which the polymer is grafted to the surface (referred to as the "graft-to-surface" method). In this method, polymers carrying adhesive moieties with strong surface affinity are synthesized and then grafted onto the surface through their adhesive moieties.

The invention provides a convenient method to coat particles (e.g., MNPs) with the dual-functional pCBMA polymer via two DOPA groups. Results show that representative zwitterionic polymer coated particles of the invention, pCBMA-MNPs, presented high saturation magnetization and long-term stability in bio-relevant media such as 100% human blood serum. Moreover, pCBMA-MNPs can be easily conjugated to a RGD peptide for their enhanced ability to enter targeted cells.

Preparation and Physical Properties of pCBMA-DOPA$_2$-MNPs.

Figure 14:
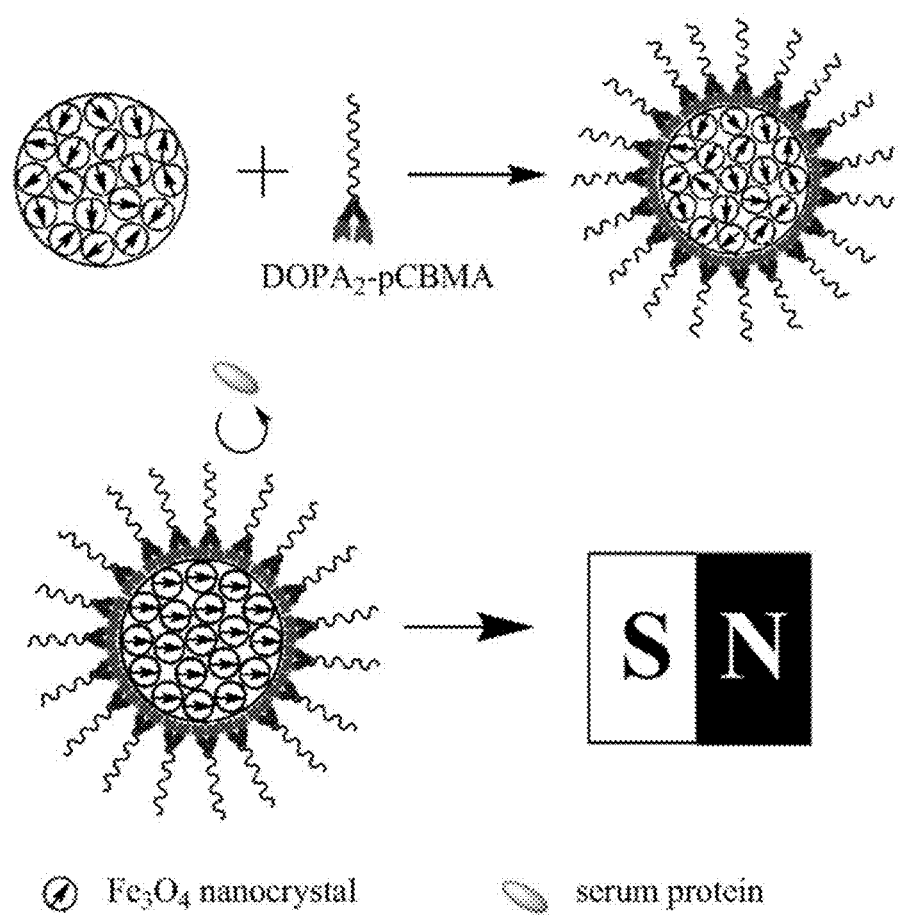
FIG. 14 is a schematic illustration of preparation of representative zwitterionic polymer coated magnetic nanoparticles of the invention, pCBMA-DOPA$_2$-MNPs, and their magnetization in the presence of a permanent magnet.
Figure 15:
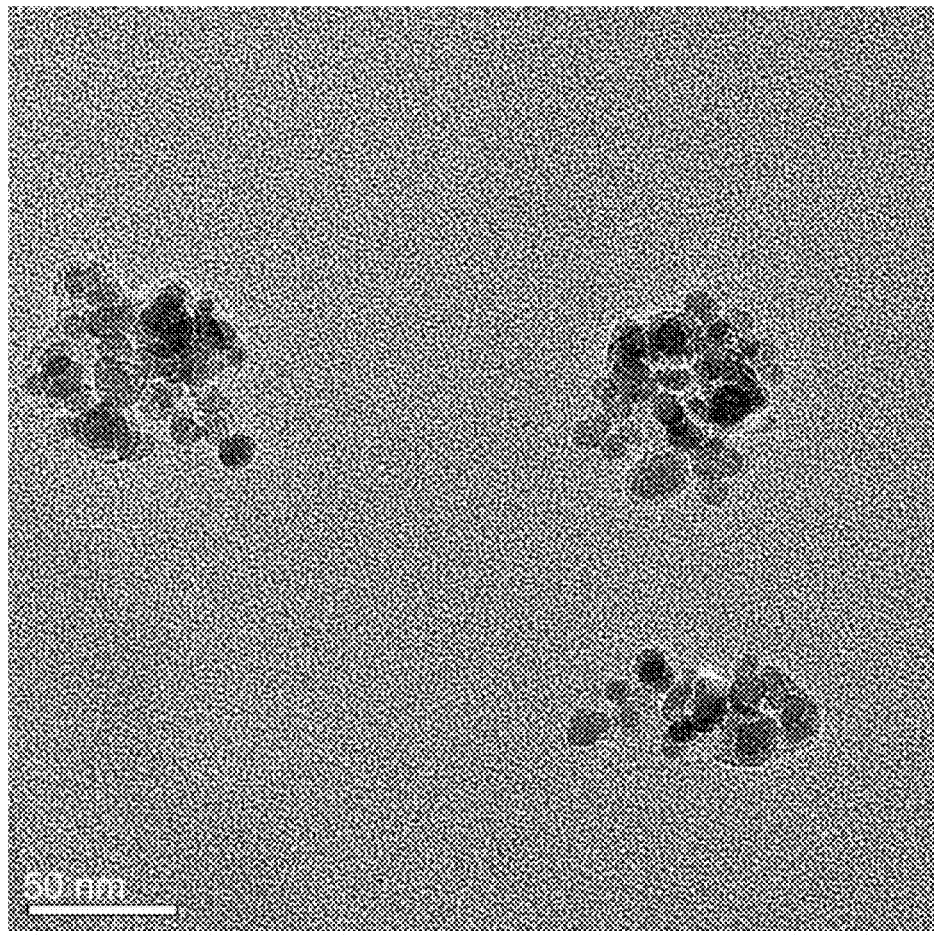
FIG. 15 is a TEM image of representative zwitterionic polymer coated magnetic nanoparticles of the invention, pCBMA-DOPA$_2$-MNPs, scale bar=50 nm
Figure 16:
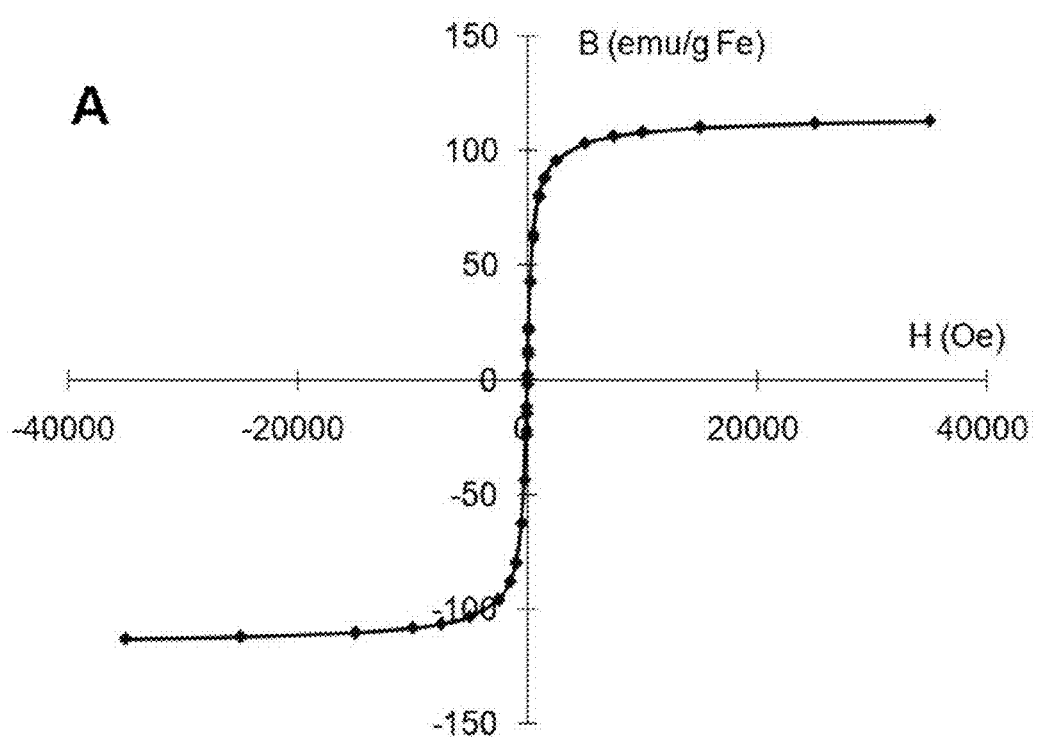
FIG. 16 illustrates magnetic properties of representative zwitterionic polymer coated magnetic nanoparticles of the invention, pCBMA-DOPA$_2$-MNPs: hysteresis loop of the MNPs measured by a SQUID magnetometer (most MNPs were collected by the magnetic about 1 min under a permanent magnet).

Co-precipitation and thermal decomposition are the two major categories of methods to prepare MNPs. In previous studies, DOPA-conjugated molecules were normally coated onto MNPs prepared by thermal decomposition. In the present invention, pCBMA-DOPA$_2$ was attached onto MNPs prepared by co-precipitation. The composition of the magnetic core and the formation of pCBMA-DOPA$_2$-MNPs are illustrated in FIG. 14. The TEM image (FIG. 15) confirms the structure of pCBMA-DOPA$_2$-MNPs. Each magnetic core is formed by a number of Fe$_3$O$_4$ nanocrystals with a single crystal size of about 15 nm. The hydrodynamic size of the magnetic cores is about 70 nm, as measured by DLS. With a DOPA$_2$-pCBMA coating, the hydrodynamic size of the nanoparticles increased to about 130 nm. Multicrystal cores are preferred for magnetic targeting, since it has been reported that without inter-particle aggregation, the small Fe$_3$O$_4$ nanocrystals have very poor mobility under a normal magnetic gradient. Negligible hysteresis in the magnetization curve in FIG. 16 reveals that at room temperature pCBMA-DOPA$_2$-MNPs possess superparamagnetic property, indicating that the nanoparticles present no coercivity (Hc) or remnant magnetization (Mr) in the absence of an external magnetic field. The SQUID magnetometer test also proves that our product has a saturation magnetization (Ms) of 110.2 emu/g Fe, which is 1.6 times higher than that of the commercial product, Feridex®. Ms is mainly determined by the Fe$_3$O$_4$ nanocrystal size, and the strong Ms of the particle of the invention is due to the size of nanocrystals (about 15 nm) is much larger than that of Feridex® (about 4.8 nm), but still in the range of superparamagnetic size (<25 nm). The multi-crystal cores with larger crystal sizes render pCBMA-DOPA$_2$-MNPs highly responsive to a magnetic field. Most nanoparticles were attracted to the permanent magnet side about 1 min.

Figure 17:
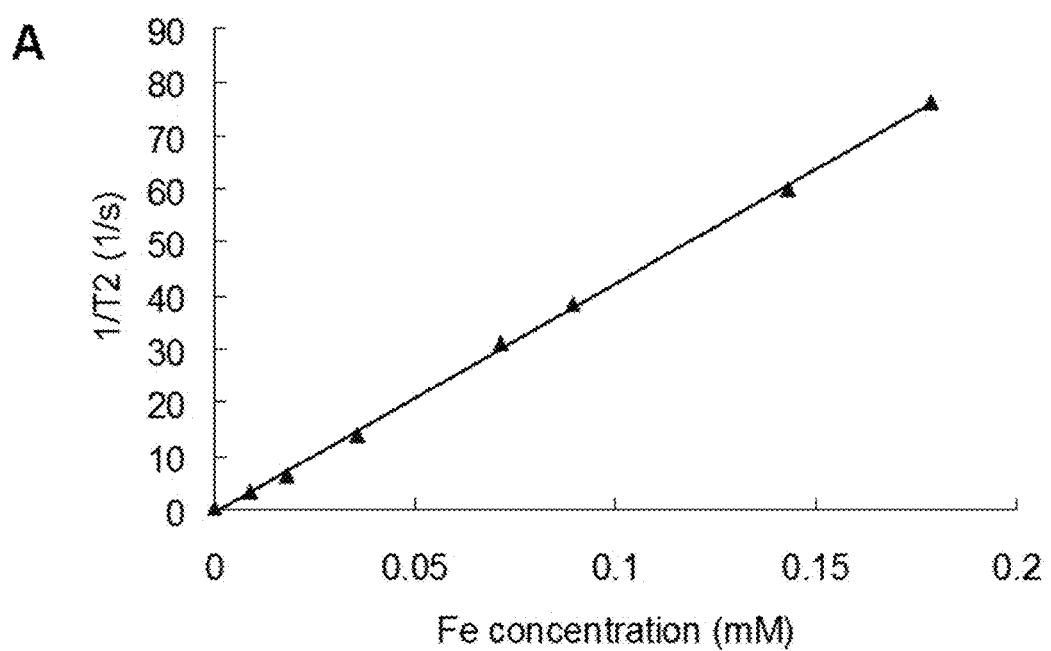
FIG. 17 illustrates R2 relaxivity of representative zwitterionic polymer coated magnetic nanoparticles of the invention, pCBMA-DOPA$_2$-MNPs, as a function of Fe concentration.

To ascertain the ability of pCBMA-DOPA$_2$-MNPs to enhance magnetic resonance imaging, the R$_2$ transverse relaxivity was measured by a clinical 3T MRI instrument. The quantitative results in FIG. 17 show that the R$_2$ relaxivity is 428 mM$^{-1}$ s$^{-1}$, which is about two times higher than that of Feridex® at a 3T magnetic field. The high relaxivity is also due to the strong Ms of pCBMA-DOPA$_2$-MNPs. These results reveal the ability of pCBMA-DOPA$_2$-MNPs to be used as a T$_2$-weighted MR contrast agent.

Stability Studies.

Figure 18:
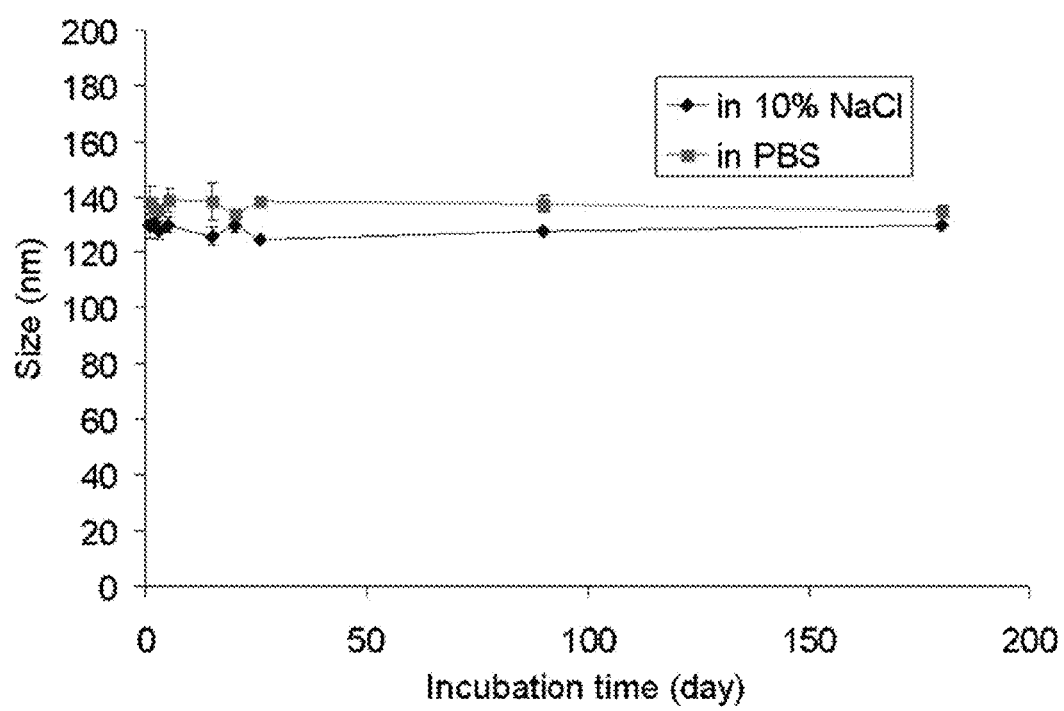
FIG. 18 compares stability of representative zwitterionic polymer coated magnetic nanoparticles of the invention, pCBMA-DOPA$_2$-MNPs, in 10% NaCl and PBS solution by DLS (n=3).

Uncoated MNPs can achieve long-term stability in DI water due to their surface charge. However, when mixed in solutions of higher ionic strengths such as PBS or 10% NaCl solution, they aggregate immediately and their hydrodynamic size increases to several thousand nanometers because their surface electronic double layer was significantly compressed by the ionic environment. With the DOPA$_2$-pCBMA coating, MNPs are stable in PBS or high ionic strength solutions such as 10% NaCl for at least 6 months without any size change monitored by DLS, as shown in FIG. 18. This result also verifies the stable formation of the pCBMA-coated MNPs.

Figure 19:
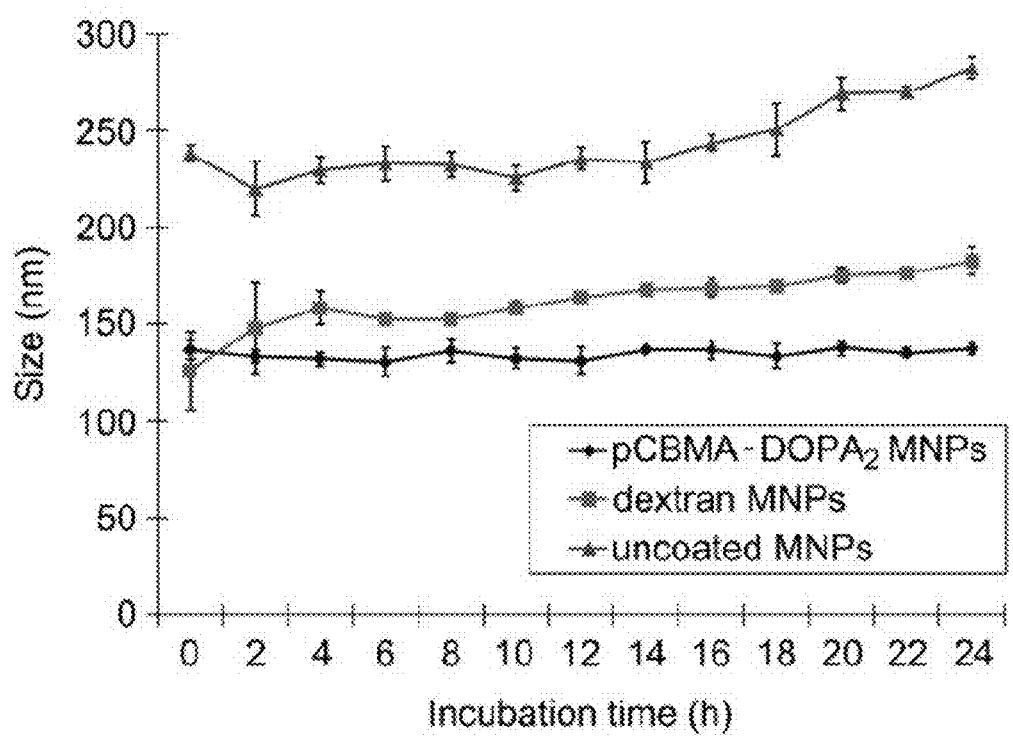
FIG. 19 compares stability of uncoated MNPs, dextran-coated MNPs and representative zwitterionic polymer coated magnetic nanoparticles of the invention, pCBMA-DOPA$_2$-MNPs, in 100% human blood serum, continuously measured by DLS at 37° C. (n=3).

To evaluate the stability of pCBMA-DOPA$_2$-MNPs in blood, the particles were suspended in 100% human blood serum at 37° C. Dextran-coated MNPs and uncoated MNPs were used as controls. Results are shown in FIG. 19. The size of uncoated MNPs increased to about 250 nm as soon as they entered the simulated blood environment. However, their size did not continue increasing to several thousand nanometers as they did in PBS and 10% NaCl solutions. This phenomenon is likely due to the formation of relatively stable particles coated with serum proteins with a size of about 250 nm. Dextran-coated MNPs showed notable size increase soon after they entered the 100% human blood serum. The size increase could be due to proteins adsorption from blood serum because the anti-fouling ability of dextran is limited. In contrast, no obvious size change could be observed for the pCBMA-DOPA$_2$-MNPs sample over the entire time-course of the test, indicating the excellent stability and ultra-lowfouling ability of the nanoparticles.

In Vitro Studies.

Figure 20:
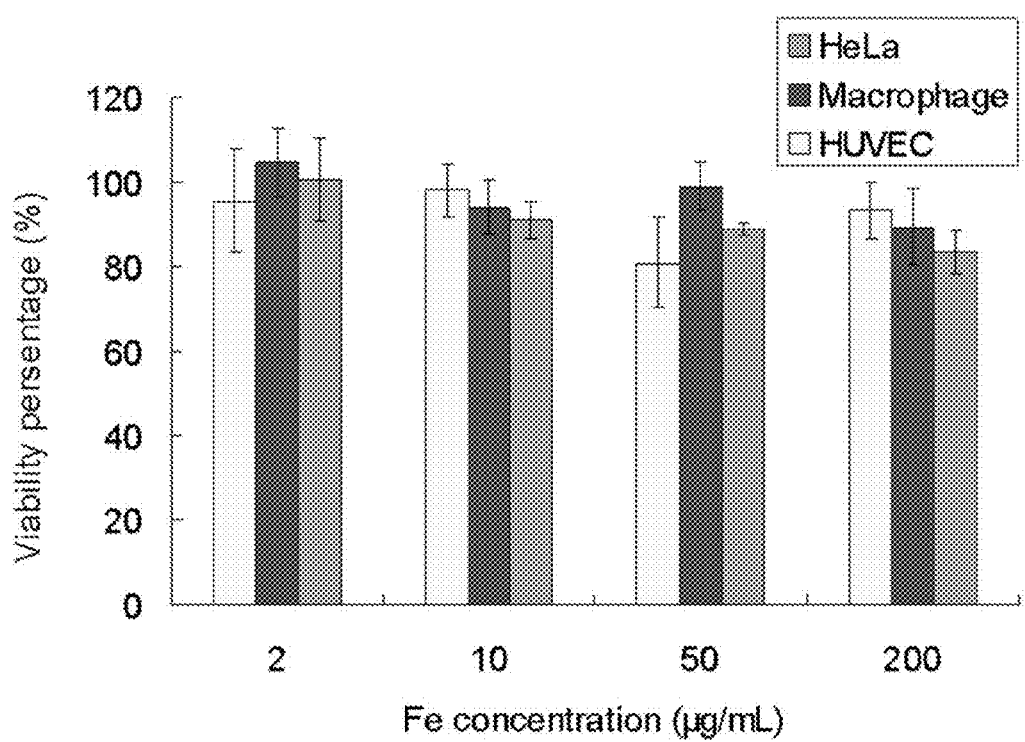
FIG. 20 compares cytotoxicity of representative zwitterionic polymer coated magnetic nanoparticles of the invention, pCBMA-DOPA$_2$-MNPs, to HeLa, macrophage, and HUVEC cells by MTT assay (n=3).
Figure 21:
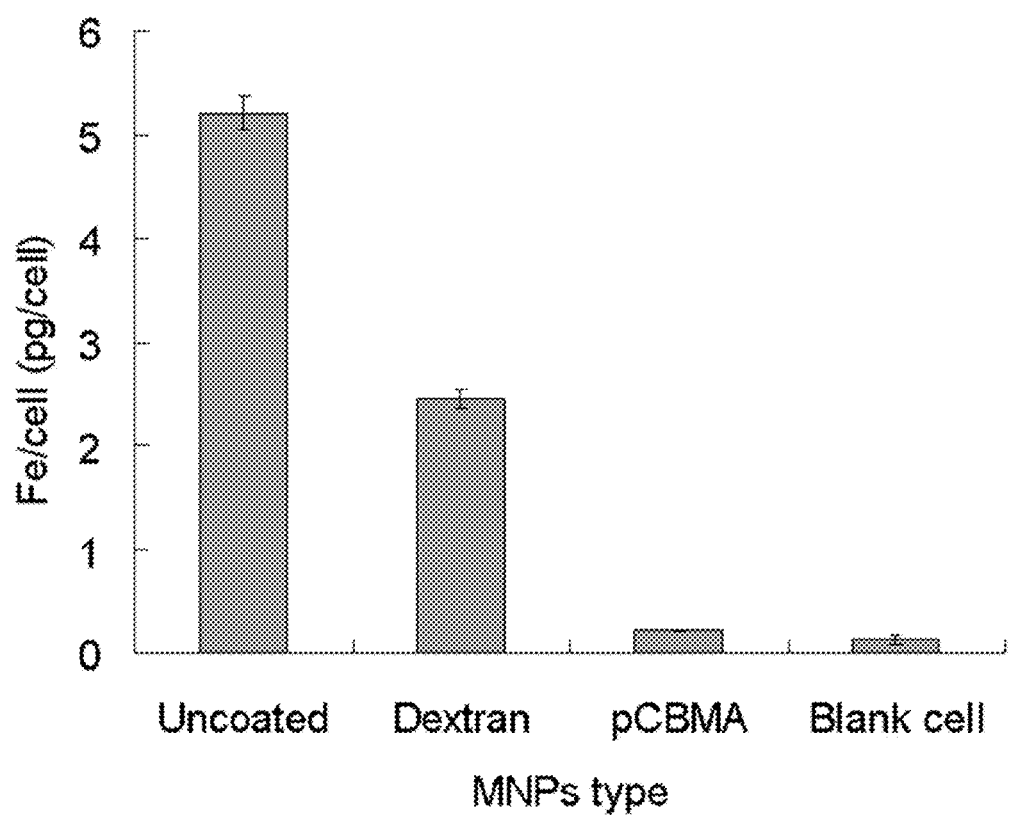
FIG. 21 compares macrophage cell uptake of uncoated MNPs, dextran-coated MNPs, and representative zwitterionic polymer coated magnetic nanoparticles of the invention, pCBMA-DOPA$_2$-MNPs, at the Fe concentration of 10 µg Fe/mL (n=3).

Resistance to macrophage cell uptake is also important to evaluate nanoparticles in vitro, because it can indicate the in vivo response of the innate immune system to the nanoparticles. Before cell uptake studies, the cytotoxicity of pCBMA-DOPA$_2$-MNPs was evaluated by an MTT assay and results are as shown in FIG. 20. No significant cell viability decrease can be observed at the tested concentration range. Mouse macrophage cell line, RAW 264.7 cell, was used in this work. As shown in FIG. 21, uptake of pCBMA-DOPA$_2$-MNPs by macrophage cell is much lower than that of dextran-coated MNPs and uncoated MNPs. This test further shows the advantage of the pCBMA coating.

pCBMA-DOPA$_2$-MNPs achieve a longer circulation half-life time than dextran coated MNPs.

Figure 22:
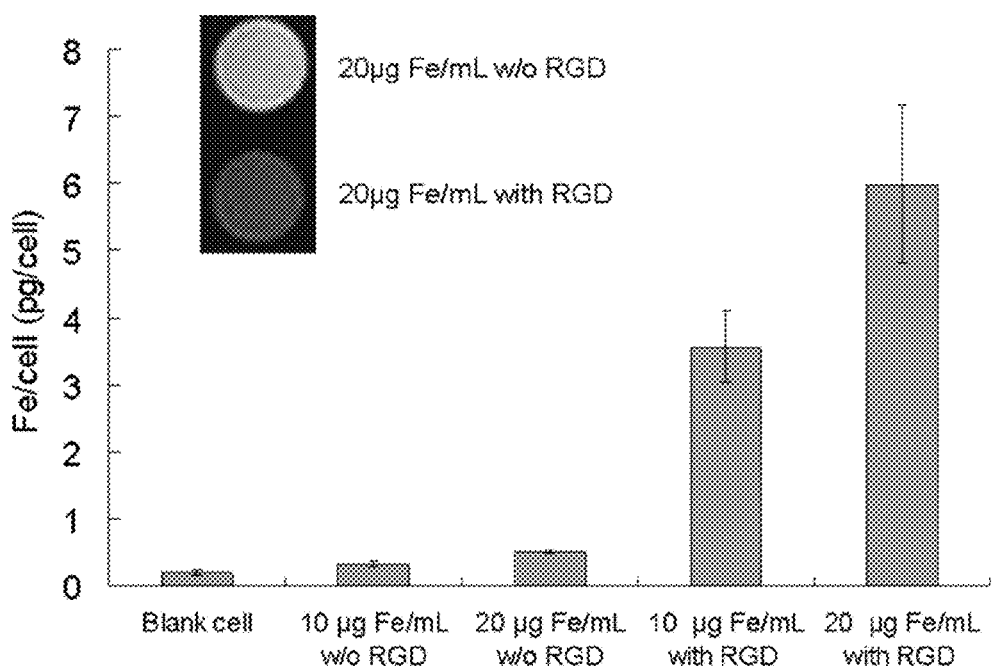
FIG. 22 compares HUVEC cell uptake of representative zwitterionic polymer coated magnetic nanoparticles of the invention, pCBMA-DOPA$_2$-MNPs, with or without RGD peptide at two different Fe concentrations (10 µg Fe/mL and 20 µg Fe/mL, n=3). The insert figure shows T2-weighted MR images of cell samples treated with pCBMA-DOPA$_2$-MNPs with or without RGD peptide at 20 µg Fe/mL.

Another important issue in the development of multifunctional MNPs is that the nanoparticles should be functionalizable. The abundant carboxyl groups in pCBMA can be efficiently and easily conjugated to biomolecules by conventional EDC/NHS chemistry. Furthermore, activated but unreacted NHS groups will be hydrolyzed back to carboxyl groups as a part of non-fouling zwitterionic groups, ensuring that the excellent nonfouling properties of the coating is maintained in post-functionalized surfaces. A RGD peptide, Cyclo[Arg-Gly-Asp-$_D$-Tyr-Lys], was used as a targeting ligand and conjugated to pCBMA-DOPA$_2$-MNPs. HUVEC cells were used to test the targeting efficiency of the MNPs by means of measuring intracellular iron concentrations. As shown in FIG. 22, at both Fe concentrations (10 μg Fe/mL and 20 μg Fe/mL) tested, non-functionalized pCBMA-DOPA$_2$-MNPs have a very low uptake level, similar to macrophage cell studies. In contrast, RGD-pCBMA-DOPA$_2$-MNPs show much higher uptake levels. T$_2$-weighted MR images visually confirmed the uptake of MNPs, as shown by the insert figure in FIG. 22, the cell sample treated with functionalized MNPs at 20 μg Fe/mL shows much higher contrast compared with the nonfunctionlized one. These results demonstrate the successful conjugation of RGD with the nanoparticles and the notable active targeting efficacy of pCBMA-DOPA$_2$-MNPs after loaded with a targeting ligand.

In summary, the invention provides a convenient method to efficiently coat MNPs with the zwitterionic pCBMA with adhesive 3,4-dihydroxyphenyl-L-alanine linkages. The superior stability of pCBMA-coated MNPs in ionic solutions and undiluted human blood serum, along with their ultra-low macrophage cell uptake suggest that pCBMA-DOPA$_2$-MNPs could achieve long blood circulation half-life in vivo. In addition, these nanoparticles possess high mobility in the presence of an external magnetic field due to their multi-crystal cores. Importantly, the pCBMA coating can be easily functionalized by target ligands via simple NHS/EDC chemistry. These features enable them to take advantages of both passive targeting (by a magnetic field) and active targeting (by targeting ligands). Thus, multifunctional pCBMA-DOPA$_2$-MNPs hold great promise as a MRI detectable, high efficient targeting delivery carrier.

Zwitterionic Nanogels

Hydrogels have been broadly used as implantable tissue scaffolds, surface coatings for implantable sensors, wound dressings, and drug delivery vectors due to their high water content, biocompatibility, and low cytotoxicity. Recently, there is an increased interest in developing hydrogel particles at the nanometer scale (i.e., nanogels) as drug delivery carriers due to their high drug-loading capacity, excellent biocompatibility, and responsiveness to environmental factors such as temperature and pH.

One of the major challenges of current nanoparticle drug delivery carriers is limited blood circulation time after intravenous (IV) systemic administration and quick uptake by the liver and spleen due to nonspecific protein adsorption onto the particles from blood. The stability of nanoparticles in blood is critical to the success of drug delivery or nanoparticle-based diagnostics. In order to achieve a prolonged blood circulation time, nanoparticles are modified with neutral and hydrophilic materials to reduce nonspecific protein adsorption from blood. Although many materials have been developed to resist non-specific protein adsorption, very few materials can achieve ultra-low fouling level, which is defined as less than 5 ng/cm$^2$ adsorbed fibrinogen.

In another aspect, the invention provides zwitterionic nanogels. The nanogels are useful as delivery vehicles for therapeutic and diagnostic agents.

In one embodiment, the zwitterionic nanogels are cross-linked nanogels prepared by copolymerization of zwitterionic monomers and a polymerizable crosslinking agent. The crosslinking agent can be a conventional crosslinking agent, a zwitterionic crosslinking agent, or a degradable conventional or zwitterionic crosslinking agent.

In one embodiment, representative zwitterionic nanogels of the invention have formula (VI):

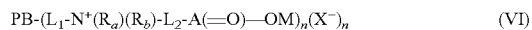

PB-(L$_1$-N$^+$(R$_a$)(R$_b$)-L$_2$-A(=O)—OM)$_n$(X$^-$)$_n$      (VI)

and, in another embodiment, representative zwitterionic nanogels of the invention have formula (VII):

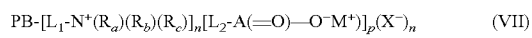

PB-[L$_1$-N$^+$(R$_a$)(R$_b$)(R$_c$)]$_n$[L$_2$-A(=O)—O$^-$M$^+$)]$_p$(X$^-$)$_n$      (VII)

wherein PB, L$_1$, R$_a$, R$_b$, R$_c$, L$_2$, A(=O)O$^-$, M$^+$, X$^-$, n, and p are as described above. For the nanogels of the invention, PB is the polymer backbone and includes crosslinks for those hydrogels that are crosslinked.

The nanogels of the invention are effective in delivering cargo. In certain embodiments, the nanogel includes one or more therapeutic agents. In certain embodiments, the nanogel includes one or more diagnostic agents. In certain embodiments, the nanogel includes one or more therapeutic agents and one or more diagnostic agents.

Therapeutic Agents.

Representative therapeutic agents that can be incorporated into and advantageously delivered by the nanogels of the invention include small molecules, nucleic acids, proteins (including multimeric proteins, protein complexes, peptides), lipids, carbohydrates, metals, radioactive elements, and/or combinations thereof.

In some embodiments, the therapeutic agent is a small molecule and/or organic compound with pharmaceutical activity. In some embodiments, the therapeutic agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitor of DNA, RNA, or protein synthesis.

In certain embodiments, a small molecule agent can be any drug. In some embodiments, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21

C.F.R. §§500 through 589, incorporated herein by reference. All listed drugs are considered acceptable for use in accordance with the present invention.

A more complete listing of classes and specific drugs suitable for use in the present invention may be found in Pharmaceutical Drugs: Syntheses, Patents, Applications by Axel Kleemann and Jurgen Engel, Thieme Medical Publishing, 1999 and the Merck Index: An Encyclopedia of Chemicals, Drugs and Biologicals, Ed. by Budavari et al, CRC Press, 1996, both of which are incorporated herein by reference.

In certain embodiments of the invention, the therapeutic agent is a nucleic acid (e.g., DNA, RNA, derivatives thereof). In some embodiments, the nucleic acid agent is a functional RNA. In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi-inducing entities (e.g., short interfering RNAs (siRNAs), short hairpin RNAs (shRNAs), and microRNAs), ribozymes, tRNAs, rRNAs, RNAs useful for triple helix formation.

In some embodiments, the nucleic acid agent is a vector. As used herein, the term "vector" refers to a nucleic acid molecule (typically, but not necessarily, a DNA molecule) which can transport another nucleic acid to which it has been linked. A vector can achieve extra-chromosomal replication and/or expression of nucleic acids to which they are linked in a host cell. In some embodiments, a vector can achieve integration into the genome of the host cell.

In some embodiments, vectors are used to direct protein and/or RNA expression. In some embodiments, the protein and/or RNA to be expressed is not normally expressed by the cell. In some embodiments, the protein and/or RNA to be expressed is normally expressed by the cell, but at lower levels than it is expressed when the vector has not been delivered to the cell. In some embodiments, a vector directs expression of any of the functional RNAs described herein, such as RNAi-inducing entities, ribozymes.

In some embodiments, the therapeutic agent may be a protein or peptide. The terms "protein," "polypeptide," and "peptide" can be used interchangeably. In certain embodiments, peptides range from about 5 to about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to about 25, about 5 to about 20, about 5 to about 15, or about 5 to about 10 amino acids in size.

Polypeptides may contain L-amino acids, D-amino acids, or both and may contain any of a variety of amino acid modifications or analogs known in the art. Useful modifications include, e.g., terminal acetylation, amidation. In some embodiments, polypeptides may comprise natural amino acids, unnatural amino acids, synthetic amino acids, and combinations thereof, as described herein.

In some embodiments, the therapeutic agent may be a hormone, erythropoietin, insulin, cytokine, antigen for vaccination, growth factor. In some embodiments, the therapeutic agent may be an antibody and/or characteristic portion thereof. In some embodiments, antibodies may include, but are not limited to, polyclonal, monoclonal, chimeric (i.e., "humanized"), or single chain (recombinant) antibodies. In some embodiments, antibodies may have reduced effector functions and/or bispecific molecules. In some embodiments, antibodies may include Fab fragments and/or fragments produced by a Fab expression library (e.g. Fab, Fab', F(ab')2, scFv, Fv, dsFv diabody, and Fd fragments).

In some embodiments, the therapeutic agent is a carbohydrate. In certain embodiments, the carbohydrate is a carbohydrate that is associated with a protein (e.g. glycoprotein, proteoglycan). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

In some embodiments, the therapeutic agent is a lipid. In certain embodiments, the lipid is a lipid that is associated with a protein (e.g., lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g., vitamin E), phospholipids, sphingolipids, and lipoproteins.

In some embodiments, the lipid may comprise one or more fatty acid groups or salts thereof. In some embodiments, the fatty acid group may comprise digestible, long chain (e.g., C8-C50), substituted or unsubstituted hydrocarbons. In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

Diagnostic Agents.

Representative diagnostic agents that can be incorporated into and advantageously delivered by the nanogels of the invention include commercially available imaging agents used in positron emissions tomography (PET), computer assisted tomography (CAT), single photon emission computerized tomography, x-ray, fluoroscopy, and magnetic resonance imaging (MRI); anti-emetics; and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, a diagnostic and/or therapeutic agent may be a radionuclide. Among the radionuclides used, gamma-emitters, positron-emitters, and X-ray emitters are suitable for diagnostic and/or therapeutic purposes, while beta emitters and alpha-emitters may also be used for therapy. Suitable radionuclides for use in the invention include, but are not limited to, 123I, 125I, 130I, 131I, 133I, 135I, 47Sc, 72As, 72Se, 90Y, 88Y, 97Ru, 100Pd, 101mRh, 119Sb, 128Ba, 197Hg, 211At, 212Bi, 212Pb, 109Pd, 111In, 67Ga, 68Ga, 67Cu, 75Br, 77Br, 99mTc, 14C, 13N, 15O, 32P, 33P, and 18F.

In some embodiments, a diagnostic agent may be a fluorescent, luminescent, or magnetic moiety. Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein. Luminescent proteins include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9th edition, 2002; and The Handbook—A Guide to Fluorescent Probes and Labeling Technologies, Invitrogen, 10th edition, available at the Invitrogen web site).

The preparation and characterization of representative zwitterionic nanogels are described in Example 4.

The preparation and characterization of representative degradable zwitterionic nanogels are described in Example 5.

pCBMA nanogels were synthesized by inverse miniemulsion free radical polymerization. Because the potential application of pCBMA nanogels as carriers involves temperature-sensitive biologically active compounds such as such as protein, DNA or RNA, polymerization was initiated by using a low-temperature free radical imitator V-70 at 40° C. The size of nanoparticles can greatly influence their blood circulation time. It is reported that nanoparticles smaller than 200 nm have less chance to be cleared by Kupffer cells and splenic filtration. Furthermore, it is also reported that small particles (<200 nm) can more effectively extravasate into tumors. In the present invention, the size of nanogels was maintained below 200 nm by adjusting the ratio and the concentration of the two surfactants (Tween 80 and Span 80). The hydrodynamic size and polydispersity of pCBMA nanogels (Table 3) were analyzed by dynamic light scattering in DI water and PBS (pH 7.4). The sizes of pCBMA nanogels with 1.5%, 3% and 5% MBAA (molar concentration) were 103.63 nm, 117.47 nm, and 99.30 nm, respectively. The size distribution of nanogels with 1.5% MBAA is the narrowest among these nanogels.

TABLE 3

Sizes of pCBMA nanogels with or without encapsulated FITC-dextran in DI water.

| Sample | Diameter (nm) in DI water (polydispersity index) |
|---|---|
| 1.5% MBAA | 103.63 (0.12) |
| 1.5% MBAA + Dextran | 100.29 (0.16) |
| 3% MBAA | 117.47 (0.25) |
| 3% MBAA + Dextran | 109.47 (0.15) |
| 5% MBAA | 99.30 (0.20) |
| 5% MBAA + Dextran | 93.58 (0.21) |

Figure 23:
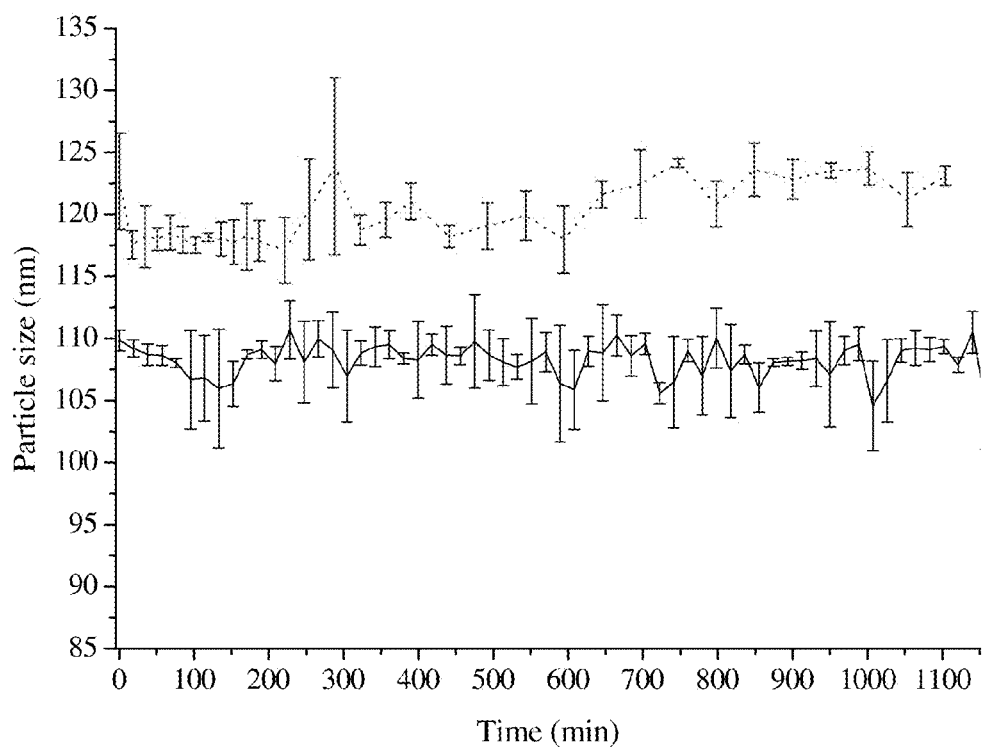
FIG. 23 compares the stability of representative zwitterionic nanogels of the invention, pCBMA nanogels with 3% MBAA (dot line) and 1.5% MBAA (black solid line), in 100% fetal bovine serum at 37° C., as a function of time.

The stability of zwitterionic nanogels in the complex medium was investigated (FIG. 23) by measuring the size change of nanogels as a function of time in 100% fetal bovine serum (FBS). Both nanogels with 1.5% and 3% MBAA retained their original sizes after an 18-hour incubation in 100% FBS. The major challenge for intravenous administration of nanogels is that the adsorption of blood proteins on the nanogels can destabilize the nanogel and lead to fast clearance by liver, spleen, and macrophage cells before the nanogel can reach its intended target. Neutral and hydrophilic materials have been coated on nanoparticles to reduce nonspecific protein adsorption.

Figure 24:
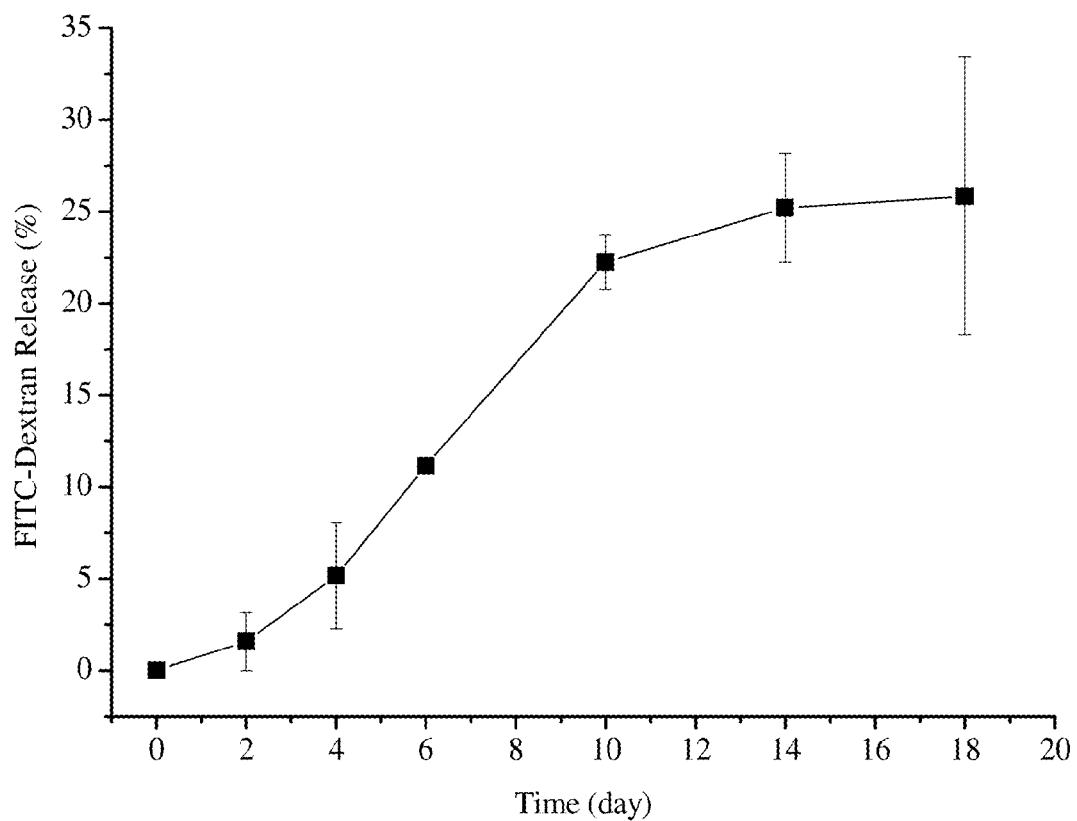
FIG. 24 illustrates in vitro FITC-dextran release from representative zwitterionic nanogels of the invention, pCBMA nanogels with 1.5% MBAA. FITC-dextran release was measured by a fluorescence spectrophotometer. The results are averaged from three replicates.

FITC-dextran was encapsulated in pCBMA nanogels as a model drug. FIG. 24 shows a controlled release of FITC-dextran from pCBMA nanogel as a function of time. 25% of FITC-dextran initially encapsulated in pCBMA hydrogel was released after 18 days. Due to their strong hydration and excellent biocompatibility, hydrogels have been extensively studied as controlled release drug delivery vectors. Macromolecules can be released from the matrix through diffusion or environmental stimuli such as the change in pH or temperature. Environmental stimuli can lead to faster release due to the decomposition of the matrix or the increased pore size of the matrix. In order to investigate the intrinsic capacity and property of novel zwitterionic pCBMA as the drug delivery carrier, the release rate of the encapsulated FITC-dextran is simply controlled by diffusion, which is determined by the molecular weight of the encapsulated drug and the pore size of the nanogels. FITC-dextran with a molecular weight of 10 kD and 1.5% crosslinker was used. The release rate can be adjusted by controlling the ratio between MBAA and CBMA monomers in aqueous stock solutions, depending on the size and hydrophilicity of a drug used for a specific application.

Figure 25:
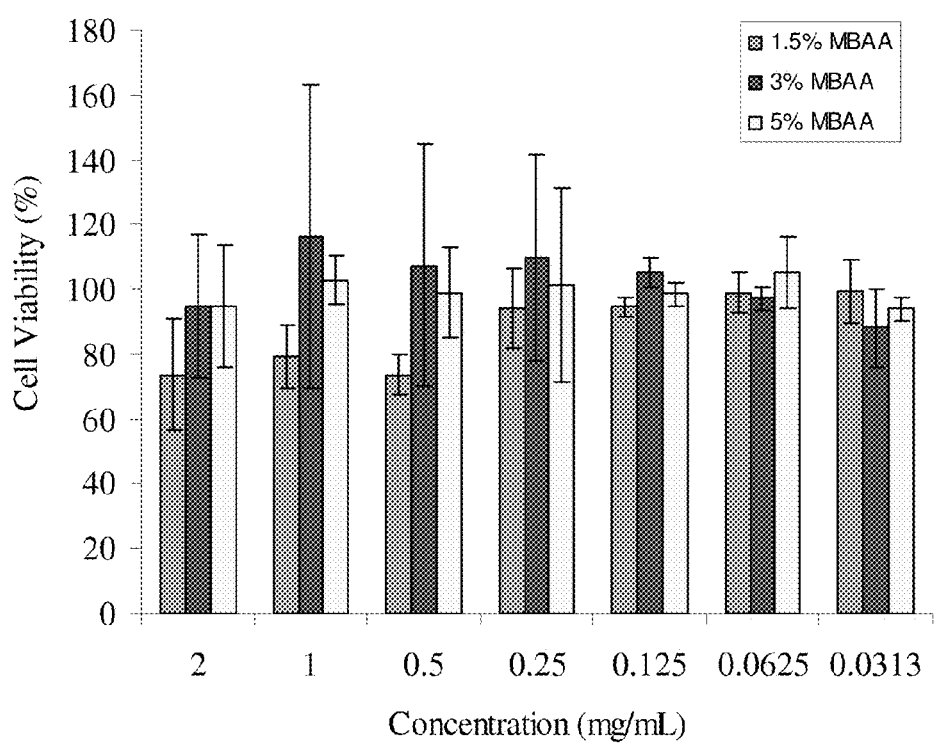
FIG. 25 compares cytotoxicity of representative zwitterionic nanogels of the invention, pCBMA nanogels with 1.5, 3, and 5% MBAA, as a function of concentration on HUVECs determined by MTT assay.

The cytotoxicity of nanogels was assessed by measuring the viability of primary HUVECs as a function of the concentration of pCBMA nanogels. The effect of the concentration of the crosslinker, MBAA, was also investigated. Results in FIG. 25 show that pCBMA nanogels with 1.5% MBAA as the crosslinker have minimal cytotoxicity even at high concentrations (2 mg/mL).

Figure 26A:
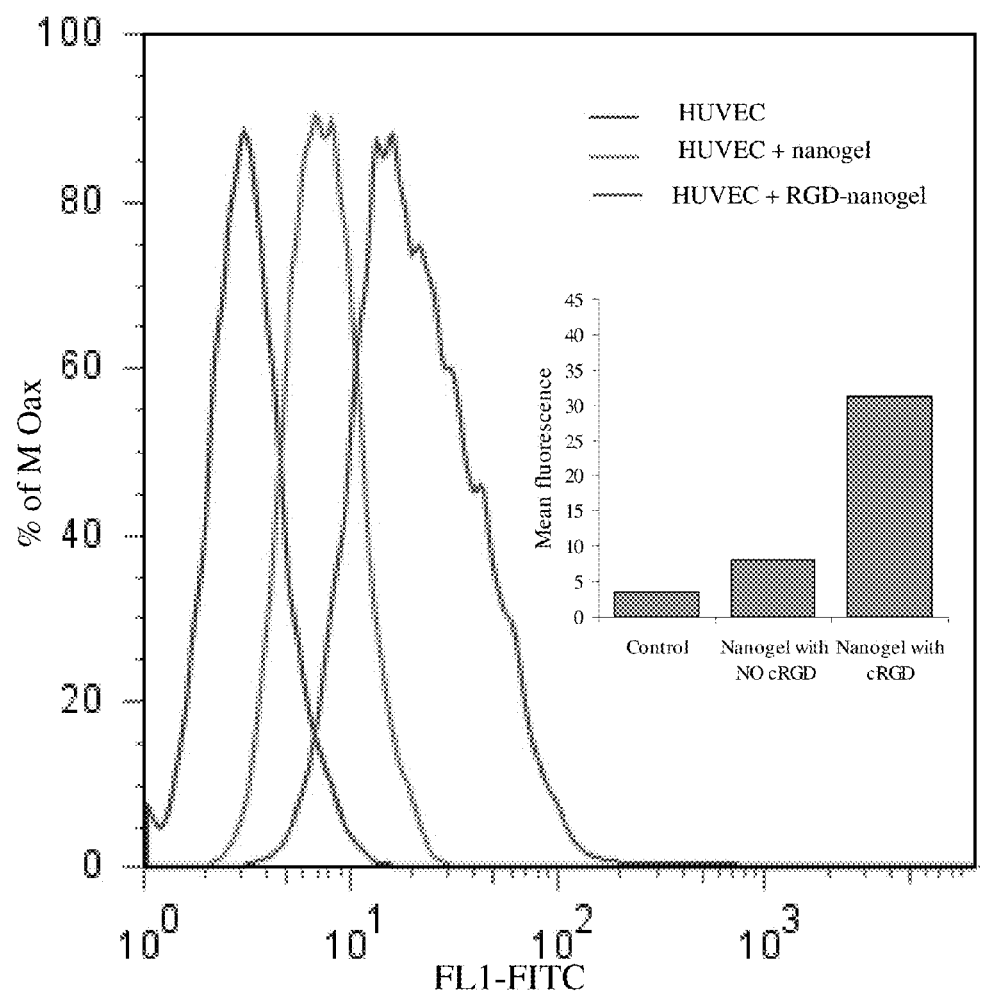
FIGS. 26A and 26B compare flow cytometric analyses of the uptake of representative zwitterionic nanogels of the invention, pCBMA nanogels: (5% MBAA) red (no pCBMA nanogels) green (pCBMA nanogels), and blue (pCBMA nanogels conjugated with RGD), at the concentration of 0.2 mg/mL (26A) and 1 mg/mL (26B).
Figure 26B:
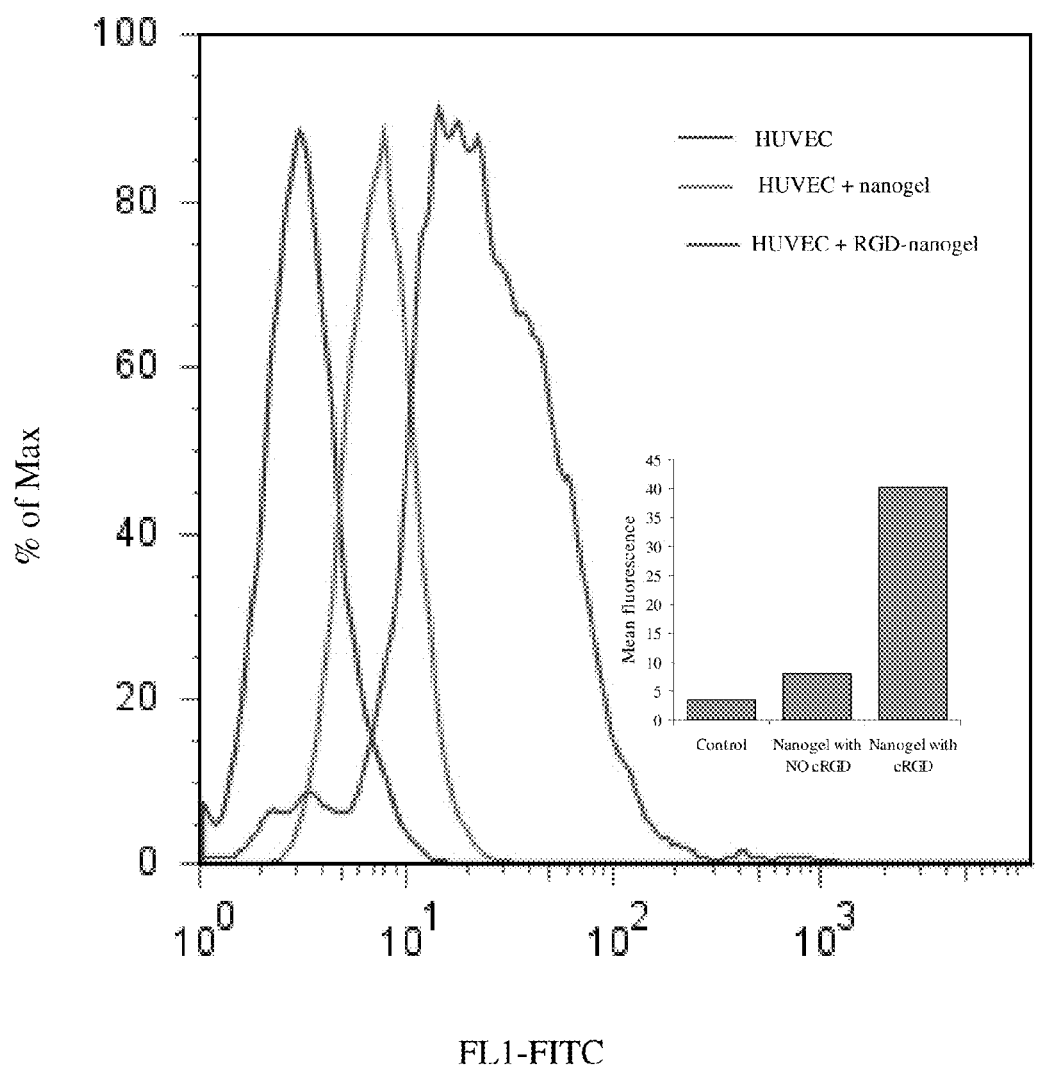

Cyclo-RGD as a targeting ligand was conjugated to FITC-dextran-containing-pCBMA nanogels using EDC/Sulfo-NHS chemistry in water. The cellular uptake of FITC-labeled nanogels was quantified with a flow cytometer. pCBMA nanogels conjugated with cyclo-RGD showed a higher uptake by HUVECs than pCBMA nanogels without cRGD (FIGS. 26A and B). pCBMA nanogels at a concentration of 1 mg/mL lead to a higher uptake of pCBMA nanogels than at a concentration of 0.2 mg/mL. The ratio of mean fluorescent intensities between cells containing cyclo-RGD-conjugated nanogels and cells containing bare pCBMA nanogels is 4.99 and 3.87 for the nanogels at the concentration of 1 mg/mL and 0.2 mg/mL, respectively. For conventional coatings on nanoparticles, mixed functional and nonfouling groups, such as the hydroxyl terminated-poly(ethylene glycol) (PEG) and carboxylate-terminated PEG, are commonly used. Due to the limitation of conjugation efficiency, unreacted functional groups such as carboxylate group and amine groups will cause nonspecific protein adsorption onto the nanoparticle surfaces in these traditional systems. However, pCBMA does not have such a problem since one pCBMA can do both jobs of nonfouling and functionalization in one material. Any unreacted functional groups in pCBMA can be hydrolyzed back into nonfouling zwitterionic groups. Thus, the density of targeting agents on pCBMA nanogels can be controlled simply by adjusting the concentration of the targeting agent during ligand conjugation.

In summary, multifunctional nanogels based on pCBMA were synthesized by an inverse microemulsion free radical polymerization method. pCBMA nanogels exhibited excellent biophysical stability in 100% fetal bovine serum and had minimal cytotoxicity. Controlled release of FITC-dextran encapsulated within pCBMA nanogels was demonstrated. The release rate depends on the particular hydrogels and drugs used and can be readily controlled. Furthermore, each side-chain of the pCBMA nanogels contains a carboxylate group for ligand immobilization. Results obtained from flow cytometry indicated that nanogels conjugated with cyclo-RGD-ligands dramatically increased the uptake of nanogels by human umbilical vein endothelium cells. These functionalizable zwitterionic nanogels are of great potentials as targeted drug delivery vectors due to their ultra stability and multiple functionalities all in one chemically-uniform particle.

Multifunctional nanoparticles have been extensively studied in the field of targeting drug delivery due to their great potential to work as an intelligent carrier for both therapy and imaging, however, a successful and sophisticated multifunctional nanoparticle-based drug delivery system should have the following properties: first, it should have high therapeutic drug loading and could release its payload at the target cite; second, it should have long in vivo circulation half-life and can target to specific site after administrated to reduce side effects to other healthy tissue; third, it should load imaging reagent for non-invasive imaging to monitor the targeting and therapeutic efficiency; fourth, after these NPs complete their missions, they should be either digested or downgraded to small fragments that can be removed from the body (e.g., via renal clearance) to avoid possible toxicity and side-effects.

Multifunctional pCBMA nanogels encapsulating monodisperse $Fe_3O_4$ magnetic NPs (MNPs) as MRI contrast reagent and fluorescence labeled dextran as a model drug were synthesized by using a reducing sensitive crosslinker. Results show that, the nanogels were degraded after entering reducing environment (similar to intracellular environment), resulting in the spontaneously release of monodisperse $Fe_3O_4$ NPs and dextran. The final degraded parts could be either digested by the body or removed from body by renal filtration.

Figure 28:
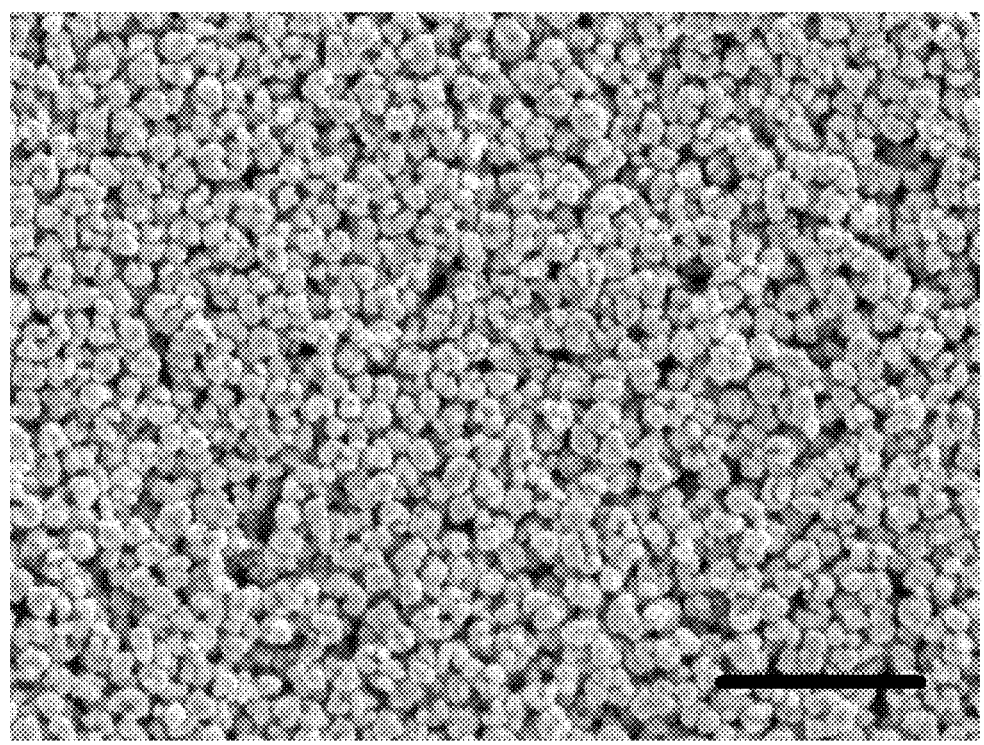
FIG. 28 is an SEM image of representative zwitterionic nanogels of the invention degradable, pCBMA nanogels (scale bar=1 µm).
Figure 29:
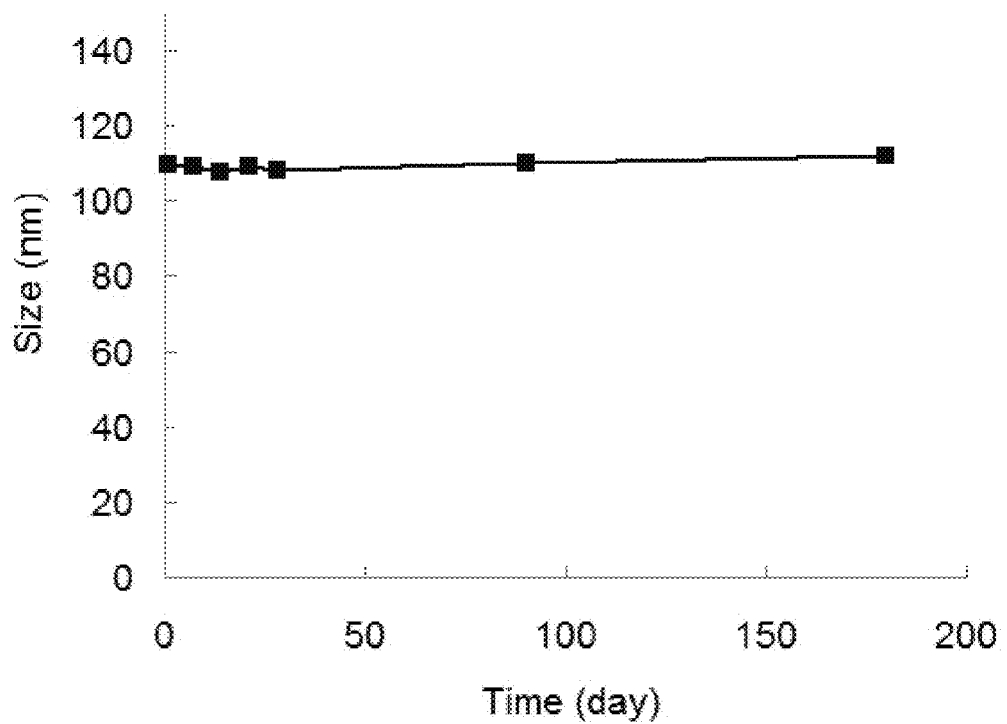
FIG. 29 illustrates the stability of representative zwitterionic nanogels of the invention in PBS.

SEM image shows the morphology of the nanogels, as presented in FIG. 28. In PBS solution, the nanogels possess a hydrodynamic size of about 110 nm. FIG. 29 shows the long term stability of the nanogels in PBS (for at least 6 months), this result is expected because it has been shown that if the NPs were well coated with pCBMA polymer, they can stay in saline solutions (PBS or NaCl) for very long time without any size change.

Figure 30:
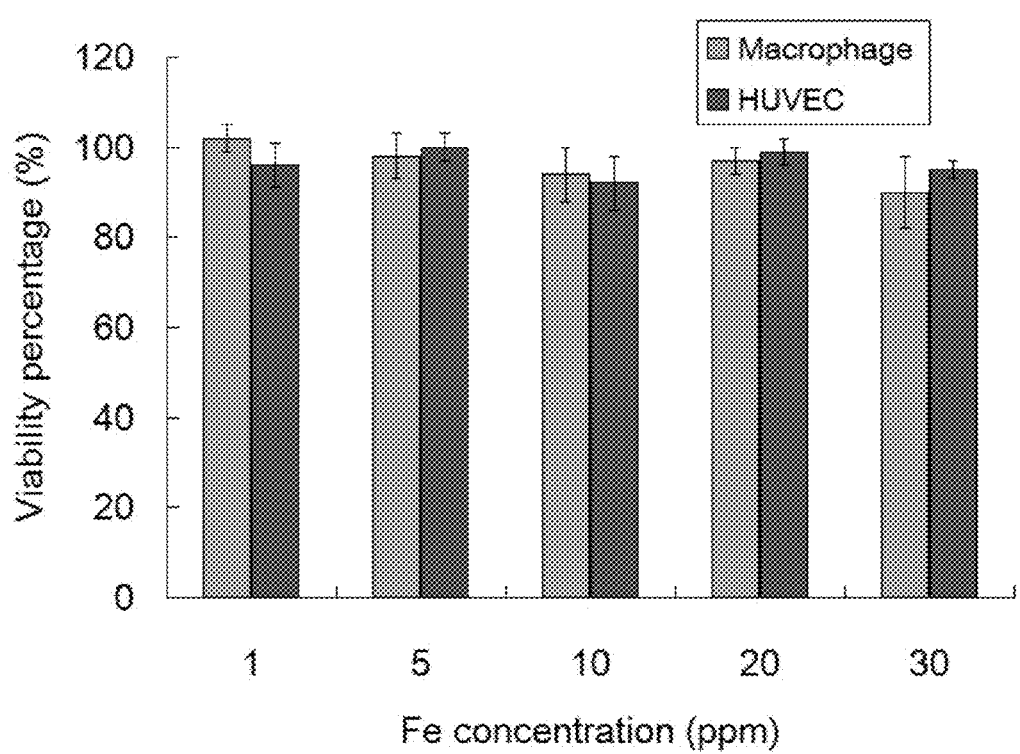
FIG. 30 illustrates the results of a cytotoxicity test of representative zwitterionic nanogels of the invention as a function of Fe concentration on macrophage cells and HUVEC cells.
Figure 31:
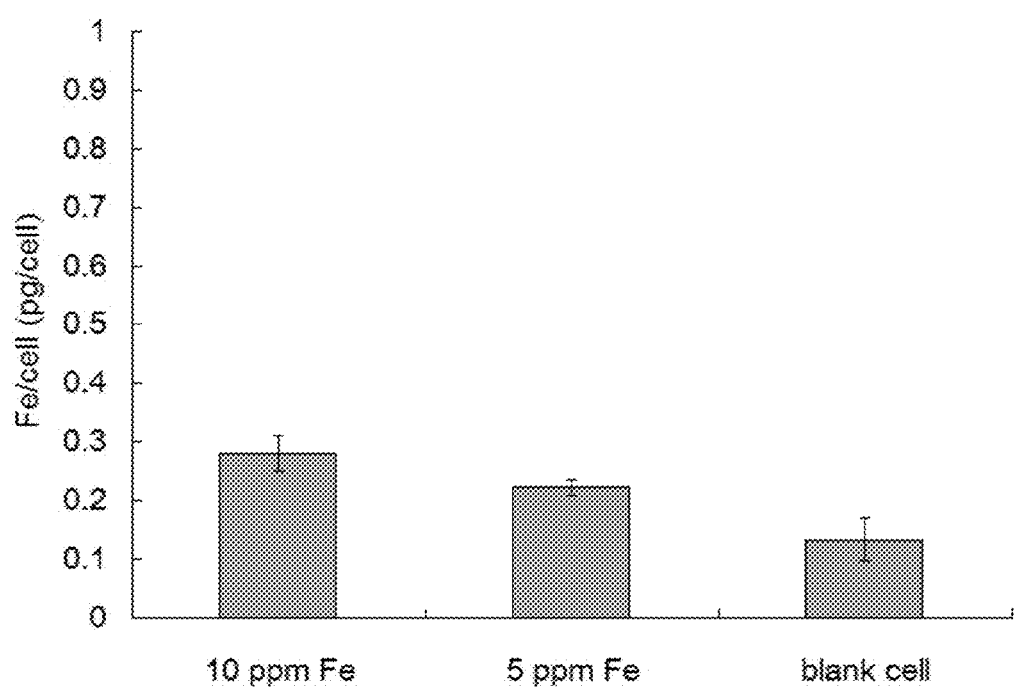
FIG. 31 illustrates the results of a macrophage uptake test of representative zwitterionic nanogels of the invention as a function of Fe concentration.

FIG. 30 shows the cytotoxicity of the nanogels on macrophage cells, in all the concentration tested, the nanogels didn't present obvious cytotoxicity to the cells. Macrophage cell uptake test is an important method to evaluate the response of the innate immune system to nanoparticles. FIG. 31 shows that, at two different Fe concentration levels (5 ppm and 10 ppm), the nanogels present very low cell uptake amount, indicating the nanogels could possibly have long circulation half-life after in vivo administration to the body.

Figure 32:
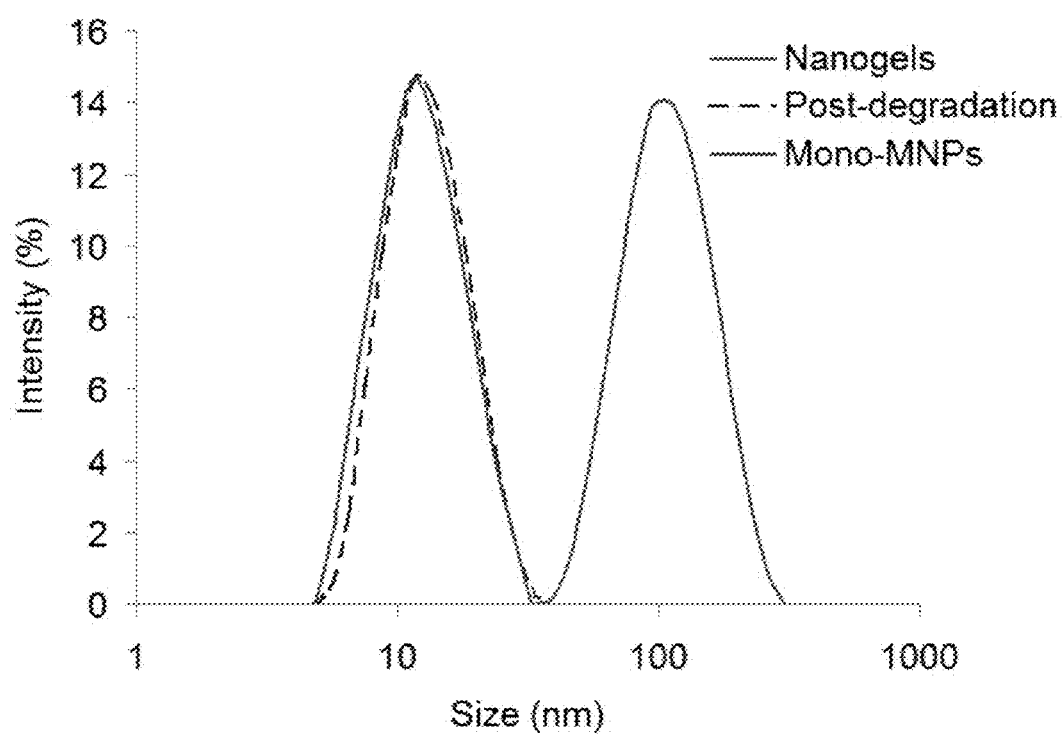
FIG. 32 illustrates the results of a degradation test (DLS) of representative zwitterionic nanogels of the invention.

Degradation of the nanogels was firstly tested by DLS, as shown in FIG. 32, after mixed with PBS solution containing 10 mM DDT at 37° C. and incubated for 24 hours, the nanogels (about 110 nm) were degraded to small pieces with a hydrodynamic size of about 12 nm, which is almost the same as the water soluble monodisperse MNPs. This result indicates the degraded solution are composed of the original water soluble monodisperse MNPs and pCBMA polymer chains.

Figure 33:
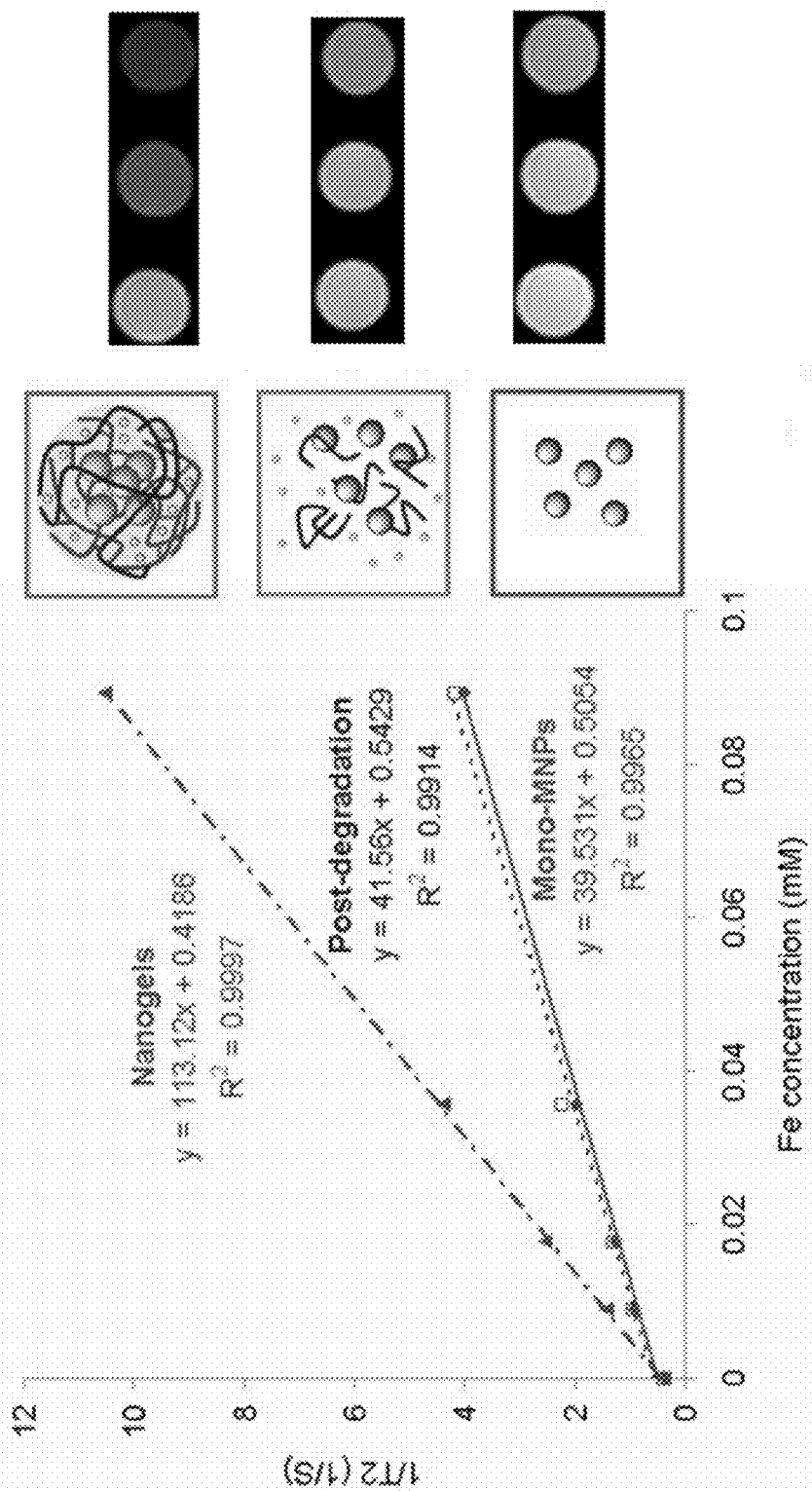
FIG. 33 illustrates the results of a degradation test (MRI) of representative zwitterionic nanogels of the invention.

Degradation of the nanogels was further evaluated by MRI test. FIG. 33 shows the T2 tests and MR images of different samples. The original monodisperse MNPs have a transverse relaxivity (R2 relaxivity, reciprocal of the proton spin-spin relaxation time) of 39.531 $mM^{-1}$ $s^{-1}$, while the MNPs loaded nanogels have a R2 relaxivity of 113.12 $mM^{-1}$ $s^{-1}$, this phenomenon is due to the encapsulating of several monodisperse MNPs could enhance the R2 relaxivity. R2 relaxivity of degraded samples decreased to 41.56 $mM^{-1}$ $s^{-1}$, indication the completely disassemble of the encapsulated monodisperse MNPs. MR images in FIG. 33 visually present the different contrast of the three samples, showing the different MR contrast ability of the samples, which is consist with the T2 tests.

Figure 34:
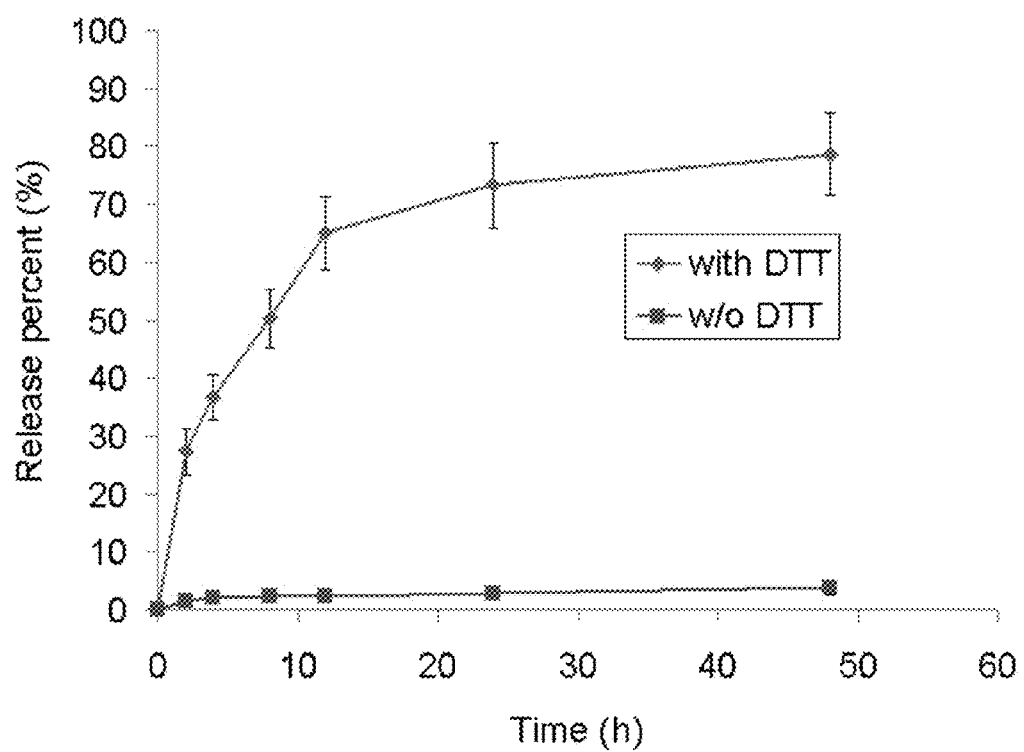
FIG. 34 compares the release of FITC-dextran from representative zwitterionic nanogels of the invention with and without 10 mM DTT at 37° C.
Figure 35:
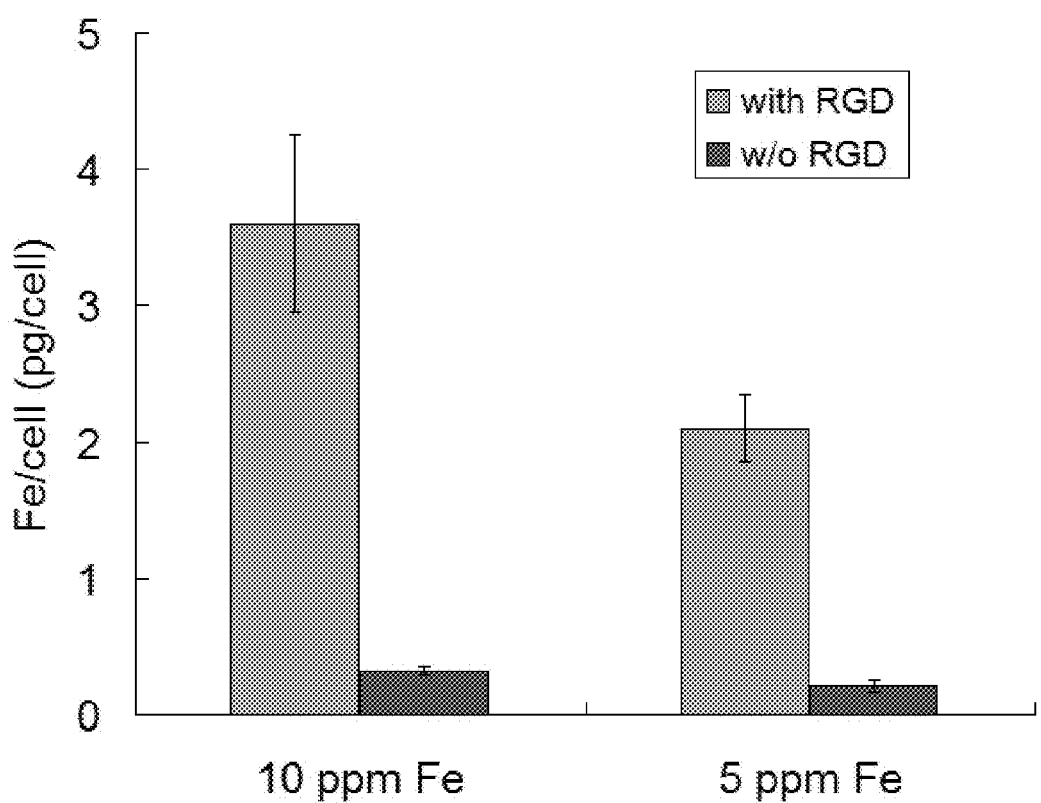
FIG. 35 compares the HUVEC cell uptake of representative zwitterionic nanogels of the invention, with or without RGD peptide at two different Fe concentrations (5 µg Fe/mL and 10 µg Fe/mL, n=3).

The release of encapsulated FITC-dextran is shown in FIG. 34, result shows the significant difference between the samples with or without the reducing reagent (DTT). The nanogels incubated with DTT shows an efficient release of FITC-dextran, about 80% of the payload with release over a period of 48 hours. In contrast, nanogels incubate without DTT could only release their payload by physical diffusion, which is much less efficient, only about 3% was released during the same 48 hours.

These results elucidated the nanogels presented in this work hold great promise to serve as intelligent targeting drug delivery carriers: the ultra-low fouling pCBMA polymer chains could efficiently stabilize the particles and resist the clearance of the particles after systemic administration, meanwhile, the pCBMA polymer chains could be easily functionalized with targeting ligands to enhance the accumulation of the nanogels. Before the nanogels arrive at the target site and internalized into the target cells, the loaded therapeutic reagents has a very slow release profile, while after the nanogels enter the intracellular environment which is much more reducing, the disulfide crosslinkers will be cleaved, resulting in the fast release of the therapeutic payload, also the loaded imaging reagent (nanoparticles, such as MNPs). A further benefit of this design is, not like some other non-degradable nano-carriers that accumulate in the body after injection, the nanogels of the invention can be removed from the body either by degradation of the MNPs or by the renal filtration of the degraded pCBMA polymer chains.

The following examples are provided for the purpose of illustrating, not limiting, the invention.

EXAMPLES

Materials

Tetraethoxysilane (TEOS), copper (I) bromide (99.999%), bromoisobutyryl bromide (BIBB, 98%), 3-(trimethoxysilyl)propylamine (TMOSPA, 97%), β-propiolactone (90%), tetrahydrofuran (THF, HPLC grade) and 2,2'-bipyridine (BPY 99%) were purchased from Sigma-Aldrich (Milwaukee, Wis.) and used as received. N-[3-(dimethylamino)propyl]acrylamide (DMAPA, 98%) was purchased from TCI (America, Oreg.). Human monoclonal antibodies against activated leukocyte cell molecule (anti-ALCAM) were purchased from R&D Systems (Minneapolis, Minn.). Bovine serum albumin (BSA) and lysozyme (Lyz) were purchased from Sigma-Aldrich (Milwaukee, Wis.). Phosphate buffered saline (PBS: 0.01M phosphate, 0.138 M sodium chloride, 0.0027 M potassium chloride, pH 7.4) was purchased from Sigma Chemical Co. and used at 0.15M. THF for reactions and washings were dried by sodium before use. Chicken egg white lysozyme were purchased from Sigma-Aldrich (Milwaukee, Wis.). Pooled human blood serum was purchased from BioChemed Services (Winchester, Va.). Human polyclonal antibodies against activated leukocyte cell molecule (anti-ALCAM) and human recombinant ALCAM/Fc chimera were purchased from R&D Systems (Minneapolis, Minn.). $PEG_{5000}$-thiol was purchased from Nektar (Huntsville, Ala.). β-propiolactone (85-90%), copper(I) bromide (99.999%), methanol (99.9%), bromoisobutyryl bromide (98%), 11-mercapto-1-undecanol (97%), sodium citrate (98%), $HAuCl_4$ (99.999%), N,N-dimethylformamide (DMF, 99%), oligo(ethylene glycol) methyl methacrylate (OEGMA) (95%), N-hydroxysuccinimide (NHS) and N-ethyl-N'-(3-diethylaminopropyl) carbodiimide hydrochloride (EDC) were purchased from Sigma-Aldrich (Milwaukee, Wis.). Ethanol (absolute 200 proof) was purchased from AAPER Alcohol and Chemical Co. Water used in these experiments was purified using a Millipore water purification system with a minimum resistivity of 18.0 MΩ·cm. The ATRP initiator, ω-mercaptoundecyl bromoisobutyrate, was synthesized through the reaction of bromoisobutyryl bromide and 11-mercapto-1-undecanol as described in Jones D M, Brown A A, Huck W T S. Langmuir 2002; 18(4): 1265-1269. $FeCl_2$ $4H_2O$ (>99%), $FeCl_3$ $6H_2O$ (>99%), $NH_3H_2O$ ($NH_3$ content: 28-30%), dextran (M.W. 10,000) from Leuconostoc mesenteroides, 3,4-dihydroxyphenyl-L-alanine, 2-bromoisobutyric acid, and dicyclohexyl carbodiimide (DCC) were purchased from Sigma-Aldrich. Tetrabutylammonium fluoride (TBAF, 1 M solution in THF containing ca 5% water), 1,3-diamino-2-hydropropane, diisopropylethylamine (DIEA), and tert-butyl chlorodimethylsilane (TBDMS, 98%) were purchased from Acros Organics. Hexane was purchased from J. T. Baker. 2-(Dimethylamino)ethyl methacrylate (DMAEMA), N,N-methylene-bis-acrylamide (MBAA), sodium salicylate, acetonitrile, ethyl ether, SPAN 80, TWEEN 80 and fluorescein isothiocyanate-dextran (FITC-dextran) (MW 10,000 and MW 20,000) were purchased from Sigma-Aldrich Chemical Co. (MO, USA). N-hydroxysulfosuccinimide (Sulfo-NHS) was purchased from Acros Organics (USA). Cyclo[Arg-Gly-Asp-D-Tyr-Lys] (cRGD) was purchased from Peptides International (KY, USA). 2,2'-Azobis(4-methoxy-2,4-dimethyl valeronitrile) (V-70) was purchased from Wako Pure Chemical Industries (VA, USA). Oleic acid (90%), dithiothreitol (DTT, 99%), and cetyltrimethylammonium bromide (CTAB, 95%) were purchased from Sigma-Aldrich; L-Cystine (98%), sodium oleate (95%) were purchased from TCI America. The disulfide crosslinker, L-cystine bisacrylamide (BACy), was synthesized according to a reported method.

Example 1

Preparation and Characterization of Representative Zwitterionic Coated Particles: Silica Nanoparticles In this example, the preparation and characterization of representative zwitterionic polymer coated particles, silica nanoparticles, are described.

Synthesis of a CBAA Monomer.

A CBAA monomer, (3-Acryloylamino-propyl)-(2-carboxyethyl)dimethyl-ammonium was synthesized as described in Vaisocherova, H. Yang, W. Zhang, Z. Cao, Z. Cheng, G. Piliarik, M. Homola, J. Jiang, S. Anal. Chem. 2008, 80, 7894-7901. Typically, 1.54 g of DMAPA was reacted with 0.99 g of β-propiolactone in 50 mL of anhydrous acetone at 0° C. for 2 h under nitrogen protection. The product (white precipitate) was washed with anhydrous ether three times, dried in vacuum, and stored as 4° C. Yield: 81%. $^1$H NMR (Bruker 500 MHZ. DMSO-$d_6$): 8.61 (t, 1H, N—H), 6.28 (t, 1H, CHH═CH), 6.13 (t, 1H, CHH═CH), 5.61 (t, 1H, CHH═CH), 3.44 (t, 2H, N—$CH_2$—$CH_2$—COO), 3.21 (m, 4H, NH—$CH_2$—$CH_2$—$CH_2$), 2.97 (s, 6H, N—$(CH_3)_2$), 2.25 (t, 2H, $CH_2$-000), 1.87 (t, 2H, NH—$CH_2$—$CH_2$—$CH_2$).

Synthesis of a Surface Initiator.

The ATRP initiator, 2-bromo-2-methyl-N-3-[(trimethoxysilyl)propyl]propanamide (BrTMOS) was synthesized as described in Zhang, Z. Chao, T. Chen, S. Jiang, S. Langmuir 2006, 22, 10072-10077. Typically, TMOSPA (1.76 g, 10 mmol) was mixed with triethylamine (1.01 g, 10 mmol) in 50 mL of dried THF. BIBB (3.45 g, 15 mmol) was added dropwise into the solution for 30 min with stirring. The reaction was kept for 12 h under nitrogen protection with stirring. The precipitate was filtered off using a frit funnel. The product was redissolved with $CH_2Cl_2$ (20 mL) and washed with 0.01 N HCl (2×20 mL) and cold water (2×20 mL). The organic phase was dried with anhydrous $CaCl_2$. After the removal of the solvent, the final product was colorless oil with a yield of 90.5%. $^1$H NMR (300 MHz, $CDCl_3$): δ 6.91 (s, 1H, NH), 3.49 (s, 9H, $SiOCH_3$), 3.24 (t, 2H, $CH_2$N), 1.94 (s, 6H, $CH_3$), 1.68 (m, 2H, $CH_2$), 0.67 (t, 2H, $SiCH_2$). $^{13}$C NMR (600 MHZ, $CDCl_3$): δ 171.98, 62.57, 50.29, 42.62, 32.44, 22.52, 7.64.

Preparation and Modification of Silica Particles (SiP).

The colloid silica particles of 66 nm in diameter were synthesized according to the well-known Stober method as described in Stober, W. Fink, A. J. Colloid. Interf. Sci. 1968, 26, 62-69. A 52 mL portion of absolute ethanol, 2.3 mL of ammonia, and 0.9 mL of water were introduced in a 100-mL, three-neck, and round-bottom flask equipped with a refrigerating system and heated to 50° C. under stirring. Then, 1.95 mL of TEOS was added into the solution and stirred at 50° C. for 24 h.

Colloid silica was coated with silane according to the Philipse and Vrij method as described in Philipse, A. P. Vrij, A. J. Colloid. Interf. Sci. 1989, 128, 121-136. A mixture of silica sol and BrTMOS was stirred for 30 min at room temperature, solvents were slowly distilled off during a period of 2 h, and the mixture was diluted with toluene. The dispersion of modified silica was purified from free silane and water or ammonia by centrifugation and redispersion in absolute ethanol. The final product was stored in absolute ethanol for further use.

Surface-Initiated ATRP on SiP.

Prior to polymerization, the initiator-coated SiP in ethanol was solvent-exchanged to methanol/water (vol/vol=3/1). The predetermined amounts of Cu(I)Br (30 mg), CBAA (120 mg) and BPY (66 mg) were added into a glass tube. The mixture was immediately degassed by three freeze-pump-thaw cycles. The degassed SiP solutions were added to the mixture to start reaction. The polymerization was carried out overnight at room temperature.

The rest of the reaction mixture was diluted by methanol and centrifuged to collect polymer-grafted SiP. This cycle of centrifugation and redispersion in methanol was repeated two times. The samples were then washed with water for three times to obtain polymer-grafted SiPs free of unbounded polymer. The products were stored in PBS for further use.

Nanoparticle Characterization.

The hydrodynamic diameters of the nanoparticles were measured by Malvern Zeta Sizer Nano-90 dynamic light scattering (DLS) instrument. Transmission electron microscope (TEM) measurements were taken on a Tecnai G2 F20 (200 kV). The samples were prepared by placing a drop of colloidal solutions on a 400-mesh carbon-coated copper grid and air-drying the grid at 25° C.

Resistance to Nonspecific Protein Adsorption.

Particle stability in protein solution was assessed by Malvern Zeta Sizer Nano-90 dynamic light scattering (DLS) instrument. Experiments were done by re-suspending 0.1 mg modified nanoparticles with 10 mg/mL protein in phosphate buffer solution (pH 7.4). Then, the size change of the nanoparticles during the incubation was tracked by DLS.

Example 2

Preparation and Characterization of Representative Zwitterionic Coated Particles: Gold Nanoparticles In this example, the preparation and characterization of representative zwitterionic polymer coated particles, gold nanoparticles, are described.

Synthesis of CBAA Monomer.

(3-Acryloylamino-propyl)-(2-carboxy-ethyl)-dimethylammonium (CBAA) was prepared as described in Example 1.

Preparation of Bare Gold Nanoparticles (GNPs).

GNPs with an average diameter of 18.5 nm were prepared by reduction of $HAuCl_4$ with citric sodium as described in Storhoff J J, Elghanian R, Mucic R C, Mirkin C A, Letsinger R L. J. Am. Chem. Soc. 1998; 120(9): 1959-1964. An aqueous solution (1.75 ml) of 1% (w/v) sodium citrate was added quickly to a boiling aqueous solution (100 ml) of 0.01% (w/v) $HAuCl_4$ under stirring, resulting in a change in solution color from pale yellow to deep red. After the color change, the solution was refluxed for an additional 15 min, allowed to cool to room temperature, and subsequently filtered through a Micron Separations Inc. 0.45 μm nylon filter. A typical solution of 18.5 nm diameter gold particles exhibited a characteristic surface plasmon band centered at 523.2 nm.

Preparation of CBAA Coated GNPs (pCBAA-GNPs).

As shown in FIG. 6, prior to the reaction, bare GNPs (8.5 ml) was mixed with the initiator (10 μl, 100 mM) in DMF (1.5 ml) and stirred for 24 h at room temperature. The initiator-functionalized GNPs were then purified with methanol three times by centrifugation (8000 r.p.m., 15 min) to obtain 1.5 ml solution A. 600 mg CBAA monomer, 28.533 mg copper(I) bromide and were dissolved in 3 ml degas sed methanol and 1.5 ml water under nitrogen atmosphere to obtain solution B. Solution A was deoxygenated by bubbling nitrogen before mixed with solution B. The final mixture was stirred (100 r.p.m.) at room temperature for 90 min or 3 h to control the coating thickness. After the polymerization, pCBAA-GNPs were washed several times by centrifuging/redispersing in water.

Preparation of $PEG_{5000}$ Coated Gold Nanoparticles (PEG-GNPs).

$PEG_{5000}$-thiol was added in excess and reacted with the gold nanoparticles (GNPs) for 30 min at room temperature. The modified particles were centrifuged at 5000×g for 5 min to remove unreacted PEG modifiers and resuspended in the appropriate solvent.

Preparation of OEGMA Coated Gold Nanoparticles (OEGMA-GNPs).

According to the same procedure as pCBAA-GNPs, the initiator-functionalized GNPs were purified with Milli-Q water three times by centrifugation to obtain 1 ml solution A. 47.7 mg copper(I) bromide and 104 mg 2,2-bipyridine were dissolved in 4 ml degassed methanol under nitrogen atmosphere to obtain solution B. Solution A was deoxygenated by bubbling nitrogen before directly mixed with solution B. 2 g macromonomer OEGMA was added and the final mixture was stirred at room temperature for 90 min. After the polymerization, OEGMA-GNPs were washed several times by centrifuging/redispersing in Milli-Q water.

PolyCBAA Functionalization Method.

The carboxyl groups on small pCBAA-GNPs were first activated by 0.05 M NHS and 0.2 M EDC (pH of final NHS/EDC solution was about 5.5). After centrifuging at 8000 r.p.m. for 15 min, the pCBAA-GNPs were dispersed in the polyclonal anti-ALCAM (R&D Systems, Minneapolis, Minn.) solution in 10 mM sodium borate buffer (pH 8.5-9.0). After all noncovalently bound ligands were removed by centrifugation at 8000 r.p.m. for 15 min, the pCBAA-GNPs were re-suspended in PBS containing ALCAM (R&D Systems, Minneapolis, Minn.) of different concentrations. The antigen-induced aggregation of GNPs was observed by spectrometer from 400-800 nm.

Example 3

Preparation and Characterization of Representative Zwitterionic Coated Particles: Magnetic Iron Oxide Gold Nanoparticles In this example, the preparation and characterization of representative zwitterionic polymer coated particles, magnetic iron oxide nanoparticles, are described.

Synthesis of $DOPA_2(TBDMS)_4$—Br Initiator.

Figure 13:
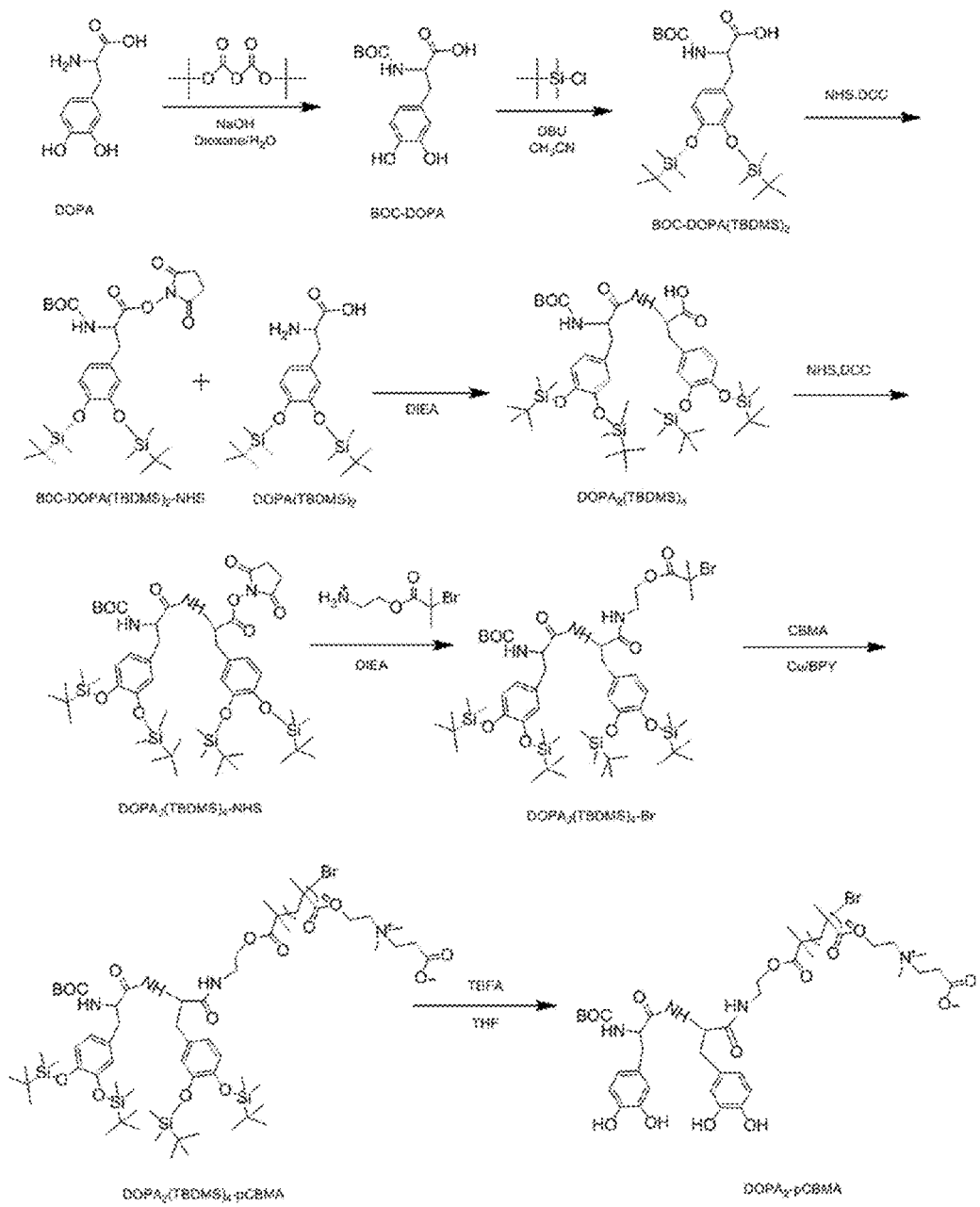
FIG. 13 is a schematic illustration of the preparation of a useful initiator (DOPA$_2$(TBDMS)$_4$—Br) and the preparation of a useful zwitterionic material (DOPA$_2$-pCBMA) for coating particles to provide zwitterionic polymer coated particles of the invention.

FIG. 13 illustrates the synthesis of $DOPA_2(TBDMS)_4$—Br initiator. $DOPA_2(TBDMS)_4$—NHS and 2-aminoethyl 2-bromoisobutyrate were synthesized as described in Dalsin J L, Lin L J, Tosatti S, Voros J, Textor M, Messersmith P B. Langmuir 2005; 21(2):640-646; Sever M J, Wilker J J. Tetrahedron 2001 July:57(29):6139-6146; Lu C W, Hung Y, Hsiao J K, Yao M, Chung T H, Lin Y S, et al. Nano Lett 2007 January:7(1):149-154. To prepare the initiator, $DOPA_2(TBDMS)_4$—NHS (1032 mg, 1.00 mM) was dissolved in mL dry N,N-dimethylformamide (DMF), and the trifluoroacetic acid salt of 2-aminoethyl-2-bromoisobutyrate (339 mg, 1.00 mM) was added under nitrogen. The mixture was stirred on an ice bath before DIEA (385 μL, 2.2 mM) was added via a syringe. After 1 h, the mixture was warmed to room temperature and stirred overnight, and then 40 mL 5% aqueous HCl was added. The mixture was extracted with 30 mL ethyl acetate, and the organic phase was washed with 30 mL DI water, dried, and concentrated in vacuo. The crude product was purified on a silica gel column with chloroform and 1% methanol as an eluent. The product, 2-bromoisobutyric acid $DOPA_2(TBDMS)_4$-amino ethyl ester was obtained as a white foam, (1.03 g, 91%). $^1$H NMR($CDCl_3$) δ: 6.60-6.82 (m, 6H), 6.38-6.44 (m, 2H), 4.64-4.67 (m, 2H), 4.12-4.19 (m, 2H), 4.09-4.11 (m, 1H), 3.14-3.60 (m, 3H), 2.66-3.04 (m, 3H), 1.95 (d, 6H), 1.31 (s, 9H), 1.0 (m, 36H) 0.2 (m, 24H).

Synthesis of $DOPA_2$-pCBMA.

$DOPA_2(TBDMS)_4$—Br initiator (52 mg, 0.05 mM), BPY (44 mg, 0.29 mM), CuBr (13.6 mg, 0.094 mM), and $CuBr_2$ (1.03 mg, 0.005 mM) were placed in a 50 mL flask and degassed three times. 1 mL degassed DMF was then added to dissolve the reactants. Then, 1.0 g CBMA, dissolved in degassed H₂O/DMF (2 mL/7 mL), was added into the flask while stirring to start the reaction. Polymerization was conducted at room temperature for 10 h. The resultant was purified by dialysis for three days against pure water. The purified polymer was lyophilized to white powder.

Both DOPA groups of the DOPA$_2$-pCBMA polymer were protected by TBDMS groups. Before the polymer was coated onto MNPs, the TBDMS groups were removed with TBAF in THF and reacted for 12 h. The deprotected polymer was purified by THF three times and dried under vacuum at room temperature. The molecular weight and molecular weight distribution of the polymer were measured with gel permeation chromatography (GPC). The number average molecular weight (Mn) was 80.8 kDa (using PEG standards) and the polydispersity index (PDI) was 1.22.

Preparation of Uncoated, Dextran Coated, and DOPA$_2$-pCBMA Coated MNPs.

Water-soluble uncoated MNPs (Fe$_3$O$_4$) were prepared by a co-precipitation method. Briefly, FeCl$_2$ 4H$_2$O and FeCl$_3$ 6H$_2$O were precipitated by adding NH$_3$H$_2$O under the protection of nitrogen gas. The resultant was washed 5 times by DI water and collected with a permanent magnet. During this procedure, any small particles with poor mobility to the magnet were removed. The homogenous colloid was filtered by a 0.2 μm membrane and stored for further use. Similar to the preparation of uncoated NPs, dextran-coated MNPs were prepared by adding NH$_3$H$_2$O to precipitate FeCl$_2$ 4H$_2$O and FeCl$_3$ 6H$_2$O at the presence of dextran. To prepare DOPA$_2$-pCBMA coated MNPs, 20 mg unprotected DOPA$_2$-pCBMA polymer was dissolved in 5 mL DI water and stirred for 1 h before 5 mg uncoated MNPs were added. The mixture was stirred for another 2 h and then washed three times with DI water.

Characterization of MNPs.

The morphology of pCBMA-DOPA$_2$-MNPs was characterized by transmission electron microscope (TEM, Tecnai G2 F20, FEI). Magnetic properties were measured by a superconducting quantum interference device (SQUID) (MPMS-5S, Quantum Design). The hydrodynamic size of the particles was analyzed with a dynamic light scattering (DLS) particle sizer (Nano Z S, Zetasizer Nano, Malvern, Pa.). The concentration of all MNP samples was determined by inductively coupled plasma atomic emission spectroscopy (ICP-AES, Elan DRC-e, PerkinElmer).

Stability Studies.

To evaluate the stability of various MNPs, uncoated, dextran-coated and DOPA$_2$-pCBMA coated MNPs were mixed in PBS, 10% NaCl, or 100% human blood serum. The particle size was continuously monitored by DLS. Tests in serum were conducted at 37° C. to mimics physiological conditions.

Cytotoxicity Assay.

The cell viability of HeLa, macrophage, and HUVEC cells was tested by a typical MTT method using a Vybrant® MTT Cell Proliferation Assay Kit (Molecular Probes). Cells were seeded in 96-well cell culture plates in 200 μL medium with serum under 5% CO² at 37° C. to allow 80-90% confluence. On the day of the test, cells were washed with PBS and incubated with 200 μL fresh medium containing nanoparticles at various concentrations. After 24 h, cells were washed with PBS and incubated with 100 μL medium and 50 μl of 12 mM MTT stock solution for another 4 h. Then, the medium was removed and 150 μL DMSO was added and incubated for 10 min. The absorbance at 570 nm was read with a 96-well plate reader (SpectraMax M5, Molecular Devices).

Macrophage Cell Uptake.

RAW 264.7 cells were cultured in DMEM medium with 10% FBS and 1% antibiotics in a 6-well plate. Prior to the test, cells were washed with PBS three times, and then various types of nanoparticles in culture media (concentration 10 mg Fe/mL) were added. After 4 h incubation at 37° C., 5% CO$_2$, cells were washed three times with PBS and lysed with 1 mL of 50 mM NaOH solution. Intracellular iron content was determined by the ICP-MS method.

Functionalization of pCBMA-DOPA$_2$-MNPs.

5 mg pCBMA-DOPA$_2$-MNPs were dispersed in 2 mL DI water. 3 mg EDC and 0.5 mg NHS were then added successively. The mixture was stirred for 0.5 h and then washed two times by DI water. After that, the nanoparticles were re-dispersed in 2 mL DI water, and 0.05 mg of RGD peptide Cyclo[Arg-Gly-Asp-$_D$-Tyr-Lys] was added. The mixture was stirred for another 3 h at room temperature. The final product was washed three times with DI water.

Magnetic Resonance Imaging.

All MRI studies were conducted on a 3 T whole body scanner (Philips Achieva R2.6.1, Best, Netherlands). An eight-channel receive-only head coil was used for signal acquisition because of its high signal-to-noise ratio (SNR). The spin-spin (T$_2$) transverse relaxation time was acquired by a multi-echo turbo spin echo (TSE) sequence. PCBMA-DOPA$_2$-MNPs at various concentrations were scanned using the following parameters: TR 3000 ms, TE 7-224 ms in steps of 7 ms, field of view (FOV) 140×120 mm$^2$, matrix size 188×160, slice thickness 10 mm, number of signal average 1, acquisition bandwidth 250 Hz/pixel, and total scan time is 5'21".

T$_2$ maps were generated from the multi-echo TSE images using a custom-programmed algorithm coded in MATLAB (Mathworks, Natick, Mass.). The T$_2$ relaxation time of each sample was measured using a custom-made image processing software CASCADE. Images were loaded into the software and then a region of interest (ROI) of no smaller than 2 cm$^2$ was carefully delineated within the boundary of the samples of interest. The average T$_2$ relaxation time of the sample was then measured automatically by CASCADE.

HUVEC Cell Targeting.

HUVEC cells were cultured in Medium 200 supplemented with low serum growth supplement in a 6-well plate. First, cells were washed by PBS for three times. Then, pCBMA-DOPA$_2$-MNPs with or without RGD peptide in fresh culture media (concentration 10 or 20 mg Fe/mL) were added. After 4 h incubation, cells were washed three times with PBS and lysed with 1 mL of 50 mM NaOH solution. Intracellular iron content was determined by the ICP-MS method. MRI images of different cell samples were also taken by the 3T MRI instrument using the similar T$_2$-weighted sequence as described above.

Example 4

Preparation and Characterization of Representative Zwitterionic Nanogels

In this example, the preparation and characterization of representative zwitterionic nanogels are described.

Inverse Microemulsion Polymerization of pCBMA Nanogels.

In a typical reaction, pCBMA nanogels were prepared via inverse microemulsion polymerization. The continuous phase solution contains 40 ml hexane, 1.4 g of TWEEN 80, 1.6 g of SPAN 80, and 8 mg of V-70. The solution was kept on ice. Aqueous monomer stock solutions were prepared by dissolving 229 mg (1 mmole) of CBMA, 4.6 mg (0.03 mmole) of MBAA in 0.5 mL of DI water. Then aqueous stock solution was added into a 100 mL flask containing 40 mL of continuous phase solution followed by vigorous shaking and a 2-minute sonication. The flasks were purged with nitrogen at 4° C. for 30 minutes to remove dissolved oxygen. During polymerization, the reaction was kept at 40° C. with stirring, and the reaction was protected under nitrogen for 4 h. For the synthesis of pCBMA nanogels containing FITC-Dextran, the conditions are the same as those for pCBMA nanogels without Dextran except that 10 mg of FITC-dextran was added to the aqueous stock solution.

Purification of Nanogels.

10 mL of the reaction solution was mixed with 30 mL of THF and stirred for 5 hours to remove surfactants. The mixture was centrifuged for 40 minutes at 4400 rpm. The supernatant was discarded, and the precipitate was washed twice with 30 ml of THF. The final precipitate was resuspended in 4 mL of DI water for 4 hours, and the aqueous solution was placed into a 100 kD molecular weight cutoff Amicon Ultra centrifugal filter devices (Millipore, Mass., USA) to remove the liquid. pCBMA nanogels were resuspended in 4 mL of DI water. The wash was repeated 10 times at room temperature. Then, the aqueous solution containing nanogels was filtered through a sterile 0.45 μm PTFE syringe filter and stored at 4° C. for further characterization. The concentration of nanogels was measured by weighing the material before and after lyophilization. The yield for nanogels containing no dextran with 1.5%, 3% and 5% crosslinker (molar concentration) is 36.2, 51.3, and 40.0%, respectively.

Hydrodynamic Diameter and Polydispersity of pCBMA Nanogels.

The hydrodynamic diameter and polydispersity of pCBMA nanogels were analyzed by a dynamic light scattering (DLS) Zetasizer Nano Z S, Malvern, UK) at the wavelength of 633 nm. The scattering angle of 173° was used and the temperature was 25° C. The values of dispersant refractive index and viscosity of water were taken as 1.330 and 0.8872 cP, respectively.

Release of Encapsulated Dextran from pCBMA Nanogels.

The release of encapsulated FITC-dextran from pCBMA nanogels with 1.5% crosslinker was determined. 40 mg of the purified pCBMA nanogels with FITC-dextran were resuspended in 20 mL of DI water. At time zero, 1 mL of solution was taken from pCBMA nanogel solution, and its total fluorescent density was measured. At different time points, 1 mL of solution was placed into a 100 kD molecular weight cutoff Amicon Ultra centrifugal filter devices (Millipore, Mass., USA), and centrifuged at a speed of 4400 rpm for 90 minutes to collect flow-through for FITC fluorescent detection. The fluorescent density at 515 nm of the filtrate was measured at 25° C. with a fluorescence spectrophotometer (F-4500 Fluorescence Spectrophotometer, Hitachi, Japan) with an excitation wavelength of 495 nm and a cut-off wavelength of 500 nm. The percentage of the released FITC-dextran was defined as the ratio of the fluorescent density of flow-through at different time points to the total fluorescent density at time zero.

Functionalization of pCBMA Nanogels.

50 mg pCBMA nanogels with 5% MBAA were resuspended in 2 mL of DI water. 153 mg of EDC and 23 mg of Sulfo-NHS were added to pCBMA nanogel solution and the solution was incubated at 25° C. for 30 minutes to activate the carboxylate group of pCBMA nanogel. Then, 1.3 mg of cRGD was added to the activated pCBMA nanogel solution and the pH value of the solution was adjusted to 8.5-9.0. The reaction was incubated at 25° C. for 3 hours. The reaction solution was placed into a 100 kD molecular weight cutoff Amicon Ultra centrifugal filter device (Millipore, Mass., USA) to remove reactants. The nanogels were resuspended in 10 ml of DI water and again passed through a 100 kD molecular weight cutoff Amicon Ultra centrifugal filter device. The wash was repeated 10 times at room temperature.

Nanogel Cytotoxicity Assay.

Cell viability was assessed using a Vybrant MTT Cell Proliferation Assay Proliferation Assay Kit (Invitrogen, USA). Human umbilical cord vascular endothelial cells (HUVEC) were seeded in 96-well tissue culture plates at a density of 7000 cells/well and cultured in 100 μL of Medium 200 supplemented with low serum growth supplement (Invitrogen, USA). Cells were incubated in 100 μL of Medium 200 with nanogels at various concentrations for 4 h. Then, the medium was removed, and 50 μL of DMSO was added and incubated for 10 min. The absorbance at 570 nm was read with a 96-well plate reader (SpectraMax M5, Molecular Devices, USA). Cell viability was expressed as the percentage of absorbance of treated cells relative to the absorbance of cells which were not incubated with pCBMA nanogels. Each measurement had 5 replicate wells.

Flow Cytometry.

HUVEC cells were seeded in 24-well tissue culture plates at a density of 10,000 cells/well and cultured in 500 μL of Medium 200 supplemented with low serum growth supplement (Invitrogen, USA). Then, cells were incubated with 500 μL of Medium 200 with 10 mg/mL or 2 mg/ml of solutions of pCBMA nanogels (5% MBAA) conjugated with or without cRGD for 4 h. After the medium was replaced with 500 μL of free Medium 200, HUVEC cells were incubated for 12 hours. Then, the medium was removed and the cells were washed three times with PBS. After detachment by trypsin, HUVEC cells were resuspended in PBS with 1% fetal bovine serum. The cellular uptake of pCBMA nanogels was analyzed by flow cytometry (FACScan, BD, USA).

Example 5

Preparation and Characterization of Representative Degradable Zwitterionic Nanogels In this example, the preparation and characterization of representative degradable zwitterionic nanogels are described.

Synthesis of Monodisperse MNPs.

Monodisperse MNPs (9 nm) were synthesized by the thermal decomposition method. Iron-oleate complex was firstly synthesized by reacting 5.4 g iron chloride and 18.25 g sodium oleate in a mixture solvent composed of 40 ml ethanol, 30 ml distilled water and 70 ml hexane at 70° C. for 4 h. The product was washed 3 times with DI water, the hexane was then evaporated off. After that, 18 g iron-oleate complex and 2.85 g oleic acid were dissolved in 100 g 1-octadecene, the solution was stirred vigorously and gradually heated to 320° C., and then kept at this temperature for 20 min. After the mixture cooled to room temperature, pure ethanol was used to precipitate the NPs, the final MNPs were dispersed in hexane.

To prepare water soluble monodisperse MNPs, 1 mL NPs hexane solution (10 mg/mL) was mixed with 10 mL water and 0.5 g CTAB. The mixture was sonicated and stirred vigorously for 30 min, the hexane solvent was then evaporated from the mixture. The resulting water soluble NPs were washed 3 times by DI water using a 100 kD molecular-weight-cutoff Amicon Ultra centrifugal filter device (Millipore) and filtered by a 0.2 μm syringe filter.

Synthesis of Nanogels.

Figure 27:
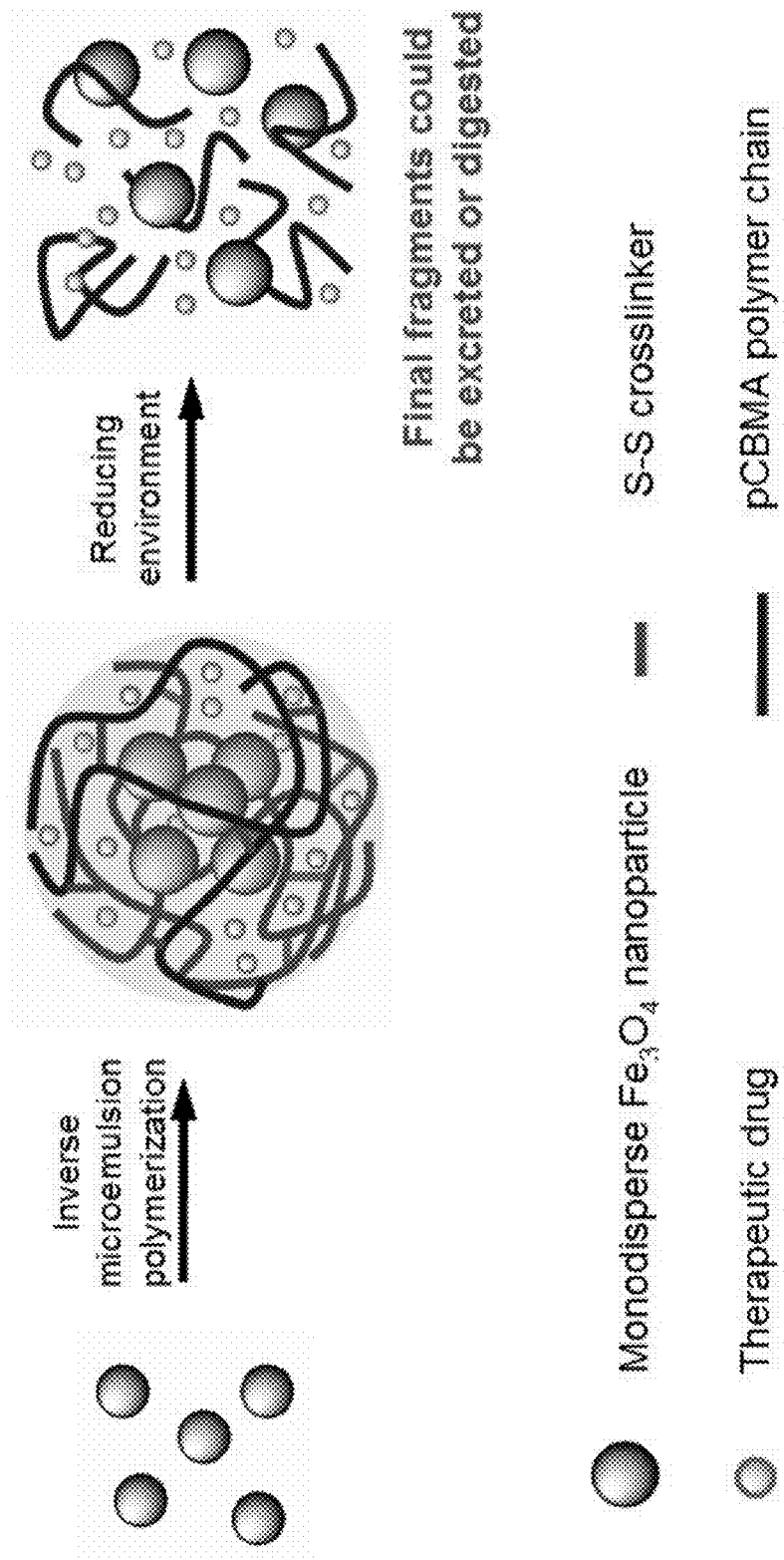
FIG. 27 is an illustration of the formation and degradation of a representative zwitterionic nanogel of the invention, a degradable pCBMA nanogel.

PCBMA nanogels loaded with MNPs were prepared by inverse microemulsion polymerization as illustrated in FIG. 27. Briefly, 0.7 g Tween 80, 0.8 g Span 80 and 4 mg V-70 were dissolved in 20 mL of hexane and kept in ice bath. 10 mg monodisperse MNPs, 10 mg FITC-dextran, 115 mg CBMA and 5 mg disulfide crosslinker were dissolve in 0.5 mL of DI water. The two stock solutions were mixed in a 100 mL flask with vigorous stirring, then strong sonication was applied to form the microemulsion. The flask was purged with nitrogen at 4° C. for 30 min to remove dissolved oxygen. During polymerization, the reaction was kept at 40° C. with stirring and was protected under nitrogen for 4 h. After the reaction, the product was washed by tetrahydrofuran (THF) for 3 times to remove the surfactants, then the product was dispersed in DI water and remaining impurities were removed by using a 100 kD molecular-weight-cutoff Amicon Ultra centrifugal filter. The final nanogels loaded with MNPs were collected by using a permanent magnet.

Nanogel Characterization.

The morphology of nanogels was characterized by scanning electron microscope (SEM, Sirion, FEI). The hydrodynamic size of all the particles was analyzed with a dynamic light scattering (DLS) particle sizer (Nano Z S, Zetasizer Nano, Malvern). The Fe concentration nanogel samples was determined by inductively coupled plasma atomic emission spectroscopy (ICP-AES, Elan DRC-e, PerkinElmer).

Cytotoxicity Assay.

The cell viability of macrophage cells and HUVEC cells was tested by a typical MTT method using a Vybrant® MTT Cell Proliferation Assay Kit (Molecular Probes). Cells were seeded in 96-well cell culture plates in 200 mL medium with serum under 5% $CO_2$ at 37° C. to allow 80-90% confluence. On the day of the test, cells were washed with PBS and incubated with 200 mL fresh medium containing nanogels at various concentrations. After 24 h, cells were washed with PBS and incubated with 100 mL medium and 50 mL of 12 mM MTT stock solution for another 4 h. Then, the medium was removed and 150 mL DMSO was added and incubated for 10 min. The absorbance at 570 nm was read with a 96-well plate reader (SpectraMax M5, Molecular Devices).

Macrophage Uptake Test

RAW264.7 cells were cultured in DMEM medium with 10% FBS and 1% antibiotics in a 6-well plate. Prior to the test, cells were washed with PBS three times, and MNPs loaded nanogels at Fe concentration of 5 ppm or 10 ppm in culture media were added. After 4 h incubation at 37° C., 5% $CO_2$, cells were washed three times with PBS and lysed with 1 mL of 50 mM NaOH solution. Intracellular iron content was determined by the ICP-AES method.

Functionalization of Nanogels and HUVEC Cells Targeting 5 mg nanogels were dispersed in 5 mL DI water. 6 mg EDC and 1 mg NHS were then added successively. The mixture was stirred for 0.5 h and then washed two times by DI water. After that, the nanoparticles were re-dispersed in 2 mL DI water, and 0.1 mg of RGD peptide Cyclo[Arg-Gly-Asp-D-Tyr-Lys] was added. The mixture was stirred for another 3 h at room temperature. The final product was washed three times with DI water.

HUVEC cells were cultured in Medium 200 supplemented with low serum growth supplement in a 6-well plate. First, cells were washed by PBS for three times. Then, nanogels with or without RGD peptide in fresh culture media (concentration 5 or 10 mg Fe/mL) were added. After 4 h incubation, cells were washed three times with PBS and lysed with 1 mL of 50 mM NaOH solution. Intracellular iron content was determined by the ICP-MS method.

Degradation Test by DLS.

0.1 mg of MNPs and FITC-dextran loaded nanogels was dispersed in 5 mL PBS solution containing 10 mM DTT, the hydrodynamic size was monitored by DLS at 37° C. Nanogels dispersed in PBS without DTT served as the control.

Degradation Test by MRI.

All MRI studies were conducted on a 3 T whole body scanner (Philips Achieva R2.6.1, Best, Netherlands). An eight-channel receive-only head coil was used for signal acquisition because of its high signal-to-noise ratio (SNR). The spin-spin (T2) transverse relaxation time was acquired by a multi-echo turbo spin echo (TSE) sequence.

Monodisperse MNPs, nanogels and degraded nanogels at various Fe concentrations were scanned using the following parameters: TR 3000 ms, TE 7-224 ms in steps of 7 ms, field of view (FOV) 140×120 $mm^2$, matrix size 188×160, slice thickness 10 mm, number of signal average 1, acquisition band width 250 Hz/pixel, and total scan time is 5'21".

T2 maps were generated from the multi-echo TSE images using a custom-programmed algorithm coded in MATLAB (Mathworks, Natick, Mass.). The T2 relaxation time of each sample was measured using image processing software CASCADE. Images were loaded into the software and then a region of interest (ROI) of no smaller than 2 $cm^2$ was carefully delineated within the boundary of the samples of interest. The average T2 relaxation time of the sample was then measured automatically by CASCADE.

Release Test.

Two PBS stock solutions (10 mL, with or without 10 mM DTT) both containing 5 mg nanogels loaded with MNPs and FITC-dextran were incubated at 37° C. At different time points, 0.5 mL solution from each sample solution was collected and the released FITC-dextran was obtained by using a 100 kD molecular-weight-cutoff Amicon Ultra centrifugal filter. The fluorescence intensity of was determined by a fluorescence spectrophotometer (F-4500 fluorescence spectrophotometer, Hitachi).

Example 6

Zwitterionic Poly(Carboxybetaine) Hydrogels for Gold Nanoparticles

In this example, the use of a representative zwitterionic crosslinked hydrogel of the invention, CBMA/CBMAX (CBMAX is carboxybetaine dimethacrylate), in a glucose biosensor is described.

Synthesis of Initiator-Modified Gold Nanoparticles (GNPs).

5 mM aqueous solution of either $HAuCl_4$ (30 mL) was added to a 4 mM solution of tetraoctylammonium bromide (TOAB) in toluene (80 mL) under stirring for 10 min. Aqueous solution $NaBH_4$ (0.4 M, 25 mL) was then added dropwise to this solution while vigorously stirring. The dark orange solution turned red within a minute, and the stirring was continued for 3 h to make sure the reaction was complete. Then the two phases were separated, and the organic phase was subsequently washed with 0.1 M $H_2SO_4$, 0.1 M NaOH, and water (three times each). Then, initiator, 274.2 mg of 11-mercaptoundecyl 2-bromoisobutyrate (Br$(CH_3)_2$COO$(CH_2)_{11}$SH) (0.808 mmol, dissolved in 1 mL toluene) were added to the solution in a dropwise fashion within 15 min. The reaction was allowed to proceed for overnight. Methanol (60 mL) was added to the system to precipitate the Au-NPs. The precipitate was collected and re-dispersed in toluene and precipitated again into ethanol. This precipitation and re-dispersion cycle was repeated twice before the pure Au-NPs (i.e. free of reaction byproducts) were obtained. The NPs were well dispersed in acetone without aggregation and the average diameter of the Au-NPs was about 5 nm.

Preparation of CBMA Coated GNPs Via ATRP (CA-GNPs).

300 mg CBMA monomer, 61.707 mg 2,2-bipyridine, and 28.533 mg copper(I) bromide were dissolved in 3 ml degassed acetone and 0.5 ml methanol under nitrogen atmosphere. 1 mL initiator-modified GNPs solution was deoxygenated by bubbling nitrogen before mixed with above solution. The final mixture was stirred (100 rpm) at room temperature for 2 h. After the polymerization, CA-GNPs were washed several times by centrifuging/redispersing in water. The average diameter of the CA-NPs was 69.8 nm in water.

Preparation of OEGMA Coated GNPs Via ATRP (OA-GNPs).

47.7 mg copper(I) bromide, 7.43 mg copper(II) bromide, and 104 mg 2,2-bipyridine were dissolved in 4 ml degassed acetone under nitrogen. 1 mL initiator-modified GNPs solution was deoxygenated by bubbling nitrogen before directly mixed with the above solution. 2 g macromonomer OEGMA was added and the final mixture was stirred at room temperature for 6 h. After the polymerization, OA-GNPs were washed several times by centrifuging/redispersing in Milli-Q water. The average diameter of the OA-NPs was 72.4 nm in water.

Preparation of OEGMA Coated GNPs Via ATRP with Addition of EGDMA Crosslinker (OC-GNPs).

47.7 mg copper(I) bromide, 7.43 mg copper(II) bromide, and 104 mg 2,2-bipyridine were dissolved in 4 ml degassed acetone under nitrogen. 1 mL initiator-modified GNPs solution was deoxygenated by bubbling nitrogen before directly mixed with the above solution. 2 g macromonomer OEGMA and 126.4 µL EGDMA was added and the final mixture was stirred at 50° C. for 6 h. After the polymerization, OC-GNPs were washed several times by centrifuging/redispersing in Milli-Q water. The average diameter of the OC-NPs was 71.9 nm in water.

Preparation of CBMA Coated GNPs Via ATRP with Addition of CBMAX Crosslinker (CC-GNPs).

300 mg CBMA monomer, 3.0 mg CBMAX, 61.7 mg 2,2-bipyridine, 4.4 mg copper(II) bromide and 28.533 mg copper(I) bromide were dissolved in 3 ml degassed acetone and 0.5 ml methanol under nitrogen atmosphere. 1 mL initiator-modified GNPs solution was deoxygenated by bubbling nitrogen before directly mixed with the above solution. The final mixture was stirred at 50° C. for 6 h. After the polymerization, CCE-GNPs were washed several times by centrifuging/redispersing in Milli-Q water. The average diameter of the CC-NPs was 80 nm in water.

Stability Test of Polymer-Coated GNPs.

Figure 36:
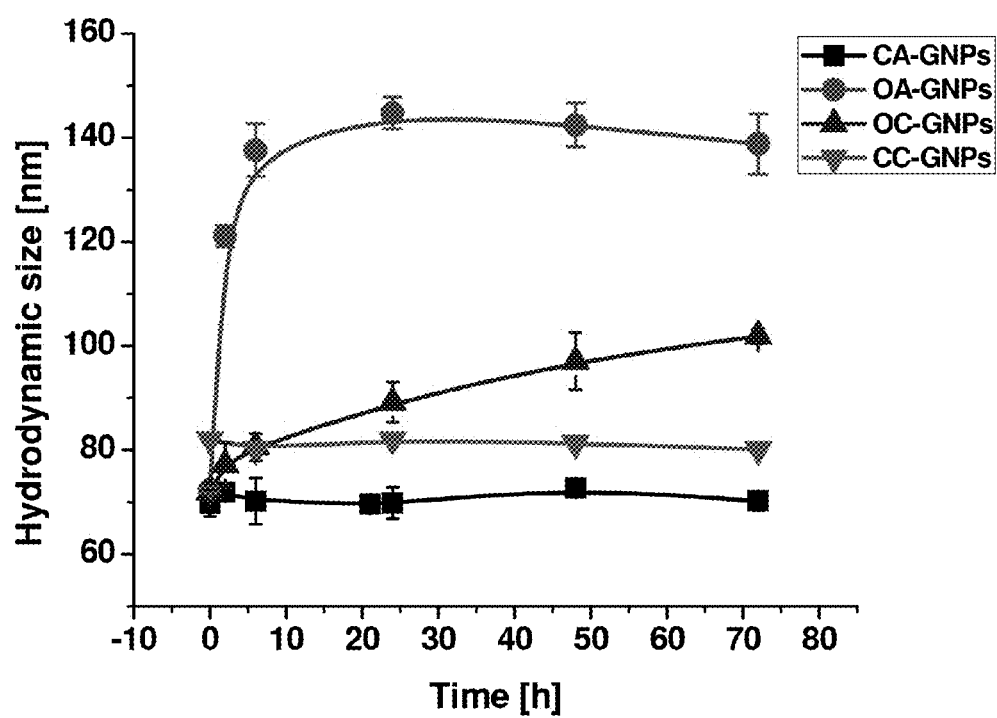
FIG. 36 compares hydrodynamic size as a function of time for polymer coated gold nanoparticles of the invention in 100% human blood serum.

The stability of polymer-coated GNPs was further evaluated in 100% human blood serum at 37° C. Due to high protein concentrations, these nanoparticles were separated from human blood serum proteins by centrifugation and re-dispersed in PBS buffer. The average diameter of the nanoparticles was then evaluated by DLS at 37° C. All the solutions were mixed with 100% human blood serum at 37° C. before the next test at different incubating time. As shown in FIG. 36, OA-GNPs showed a size increase of about 50 nm in a very short period of time. At the end of 72 h, the diameter increased to about 140 nm, indicating significant protein adsorption and particulate aggregation. Although OC-GNPs were not stable in such extreme situation, the addition of EGDMA helped to enhance the stability. The diameter increments were 6 nm and 30 nm after an incubation period of 6 h and 72 h, respectively. Precipitates could be observed in the above solutions. However, three kinds of GNPs with the protection of polyCBAA coating (CA-GNPs, CCE-GNPs, and CCC-GNPs), the interactions between proteins and nanoparticles did not cause any agglomeration and the particle sizes after their separation from human blood serum proteins was almost the same as those without serum (70 nm, 50 nm and 105.9 nm), indicating their excellent stability.

Figure 37:
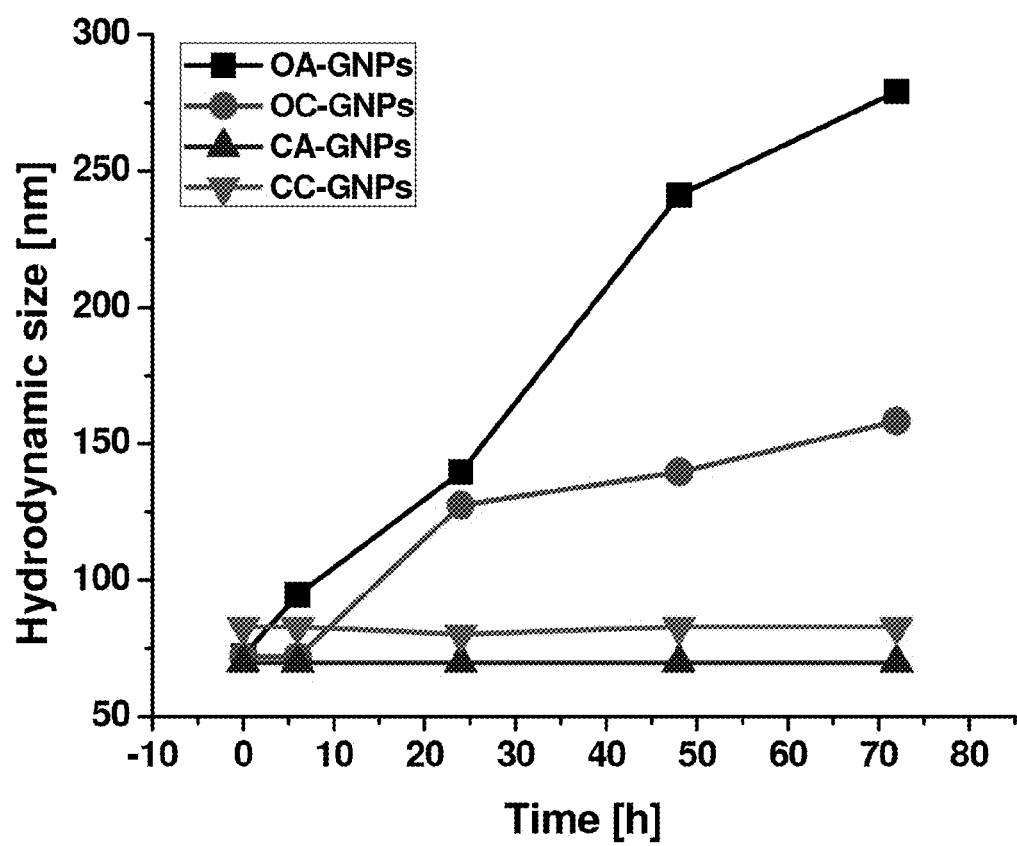
FIG. 37 compares hydrodynamic size as a function of time for polymer coated gold nanoparticles of the invention in 100% human blood serum.

Next, polymer-coated nanoparticles were mixed with human blood serum at a very high concentration and incubated at 37° C. The average diameter of the nanoparticles was then evaluated by DLS at 37° C. As shown in FIG. 37, the OA-GNPs showed an increase of about 20 nm in size after 6 h. This value increased to 200 nm after 72 h, which was attributed to the interactions of nanoparticles with proteins in the incubation serum medium. Again, the addition of EGDMA increased the stability. The diameter increment was 70 nm after an incubation period of 72 h. However, with polyCBMA coating, there is no agglomeration and all three samples showed good stability without obvious size increase during the test period of 72 h.

While illustrative embodiments have been illustrated and described, it will be appreciated that various changes can be made therein without departing from the spirit and scope of the invention.

The embodiments of the invention in which an exclusive property or privilege is claimed are defined as follows:

1. A surface having a layer of sulfobetaine polymers coupled thereto, wherein the density of the sulfobetaine polymers in the layer provides a surface having a fibrinogen adsorption of less than about 30 ng/cm$^2$ in a fibrinogen binding assay when the surface is incubated at 37° C. for 90 minutes with a 1.0 mg/mL fibrinogen solution (0.15 M phosphate buffered saline at pH 7.4).

2. The surface of claim 1, wherein the sulfobetaine polymers are prepared from one or more monomers selected from the group consisting of a sulfobetaine acrylate, a sulfobetaine acrylamide, a sulfobetaine methacrylate, and mixtures thereof.

3. The surface of claim 1, wherein the layer of sulfobetaine polymers comprises an interpenetrating sulfobetaine polymer network.

4. The surface of claim 3, wherein the interpenetrating sulfobetaine polymer network further comprises one or more polymers selected from the group consisting of a polyurethane, a silicone, a polyester, a polyethylene, and a polyamide.

5. The surface of claim 1, wherein the layer of sulfobetaine polymers comprises a sulfobetaine copolymer.

6. The surface of claim 1, wherein the layer comprises sulfobetaine polymers covalently attached to a substrate surface.

7. The surface of claim 1 on all or part of a particle.

8. The surface of claim 1, wherein the fibrinogen adsorption is less than 10 ng/cm$^2$.

9. The surface of claim 1, wherein the fibrinogen adsorption is less than 5 ng/cm$^2$.

10. The surface of claim 1, wherein the fibrinogen adsorption is less than 0.3 ng/cm$^2$.

11. The surface of claim 1, wherein the sulfobetaine polymers are prepared from one or more monomers selected from the group consisting of a sulfobetaine vinyl compound, a sulfobetaine epoxide, and mixtures thereof.

12. A substrate comprising a surface having a layer of sulfobetaine polymers grafted from the surface, wherein the density of the sulfobetaine polymers in the layer provides a surface having a fibrinogen adsorption of less than about 30 $ng/cm^2$ in a fibrinogen binding assay when the surface is incubated at 37° C. for 90 minutes with a 1.0 mg/mL fibrinogen solution (0.15 M phosphate buffered saline at pH 7.4).

13. The substrate of claim 12, wherein the sulfobetaine polymers are prepared from one or more monomers selected from the group consisting of a sulfobetaine acrylate, a sulfobetaine acrylamide, a sulfobetaine methacrylate, and mixtures thereof.

14. The substrate of claim 12, wherein the layer of sulfobetaine polymers comprises a sulfobetaine copolymer.

15. The substrate of claim 12, wherein the fibrinogen adsorption is less than 10 $ng/cm^2$.

16. The substrate of claim 12, wherein the fibrinogen adsorption is less than 5 $ng/cm^2$.

17. The substrate of claim 12, wherein the fibrinogen adsorption is less than 0.3 $ng/cm^2$.

18. The substrate of claim 12 on or forming all or part of a particle.

19. The substrate of claim 12, wherein the sulfobetaine polymers are prepared from one or more monomers selected from the group consisting of a sulfobetaine vinyl compound, a sulfobetaine epoxide, and mixtures thereof.

\* \* \* \* \*